(12) United States Patent
Frankel et al.

(10) Patent No.: US 12,070,318 B2
(45) Date of Patent: Aug. 27, 2024

(54) SYSTEMS AND METHODS FOR ELECTROENCEPHALOGRAM MONITORING

(71) Applicant: Epitel, Inc., Salt Lake City, UT (US)

(72) Inventors: Mitchell A. Frankel, Salt Lake City, UT (US); Robert Lingstuyl, Salt Lake City, UT (US); Michael K. Elwood, Farmington, UT (US)

(73) Assignee: Epitel, Inc., Salt Lake City, UT (US)

( * ) Notice: Subject to any disclaimer, the term of this patent is extended or adjusted under 35 U.S.C. 154(b) by 0 days.

(21) Appl. No.: 18/067,608

(22) Filed: Dec. 16, 2022

(65) Prior Publication Data

US 2024/0130660 A1 Apr. 25, 2024

Related U.S. Application Data

(60) Provisional application No. 63/380,132, filed on Oct. 19, 2022.

(51) Int. Cl.
*A61B 5/369* (2021.01)
*A61B 5/00* (2006.01)

(52) U.S. Cl.
CPC .......... *A61B 5/369* (2021.01); *A61B 5/0022* (2013.01); *A61B 5/0024* (2013.01)

(58) Field of Classification Search
CPC ...... A61B 5/369; A61B 5/0022; A61B 5/0024
See application file for complete search history.

(56) References Cited

U.S. PATENT DOCUMENTS

| | | |
|---|---|---|
| 4,936,306 A | 6/1990 | Doty |
| 5,309,923 A | 5/1994 | Leuchter et al. |
| 5,483,967 A | 1/1996 | Ohtake |
| 5,755,230 A | 5/1998 | Schmidt et al. |
| 6,117,077 A | 9/2000 | Del Mar et al. |
| 6,416,471 B1 | 7/2002 | Kumar et al. |

(Continued)

FOREIGN PATENT DOCUMENTS

| | | |
|---|---|---|
| EP | 2782499 B1 | 3/2021 |
| JP | 2010527709 A | 8/2010 |

(Continued)

OTHER PUBLICATIONS

Frankel et al., Wearable Reduced-Channel EEG System for Remote Seizure Monitoring. Front Neurol. Oct. 18, 2021;12: Article 728484 in 13 pages.

(Continued)

*Primary Examiner* — Navin Natnithithadha
(74) *Attorney, Agent, or Firm* — Knobbe, Martens, Olson & Bear, LLP

(57) ABSTRACT

Provided herein are systems, kits, and methods for monitoring brain activity. In some implementations, a system includes a plurality of wearable sensors having a housing with an extended, rounded shape are removably attached to the scalp of a patient and monitor electroencephalogram (EEG) signals. Approaches for instructing a user to position and active that wearable sensors are disclosed. Approaches for facilitating collection, synchronization, and processing of EEG signals are disclosed. Approaches for handing off control of the wearable sensors between portable computing devices are disclosed.

20 Claims, 28 Drawing Sheets

(56) References Cited

U.S. PATENT DOCUMENTS

| | | |
|---|---|---|
| 6,473,639 B1 | 10/2002 | Fischell et al. |
| 6,496,724 B1 | 12/2002 | Levendowski |
| 6,735,467 B2 | 5/2004 | Wilson |
| 7,848,794 B2 | 12/2010 | Genger et al. |
| 7,885,706 B2 | 2/2011 | Ludvig et al. |
| 7,970,450 B2 | 6/2011 | Kroecker et al. |
| 8,204,583 B2 | 6/2012 | Sackellares et al. |
| 8,538,512 B1 | 9/2013 | Bibian et al. |
| 8,562,523 B2 | 10/2013 | Osario |
| 8,594,763 B1 | 11/2013 | Bibian et al. |
| 8,626,261 B2 | 1/2014 | Ko et al. |
| 8,628,462 B2 | 1/2014 | Berka et al. |
| 8,666,484 B2 | 3/2014 | Nierenberg |
| 8,688,209 B2 | 4/2014 | Verbitskiy |
| 8,786,624 B2 | 7/2014 | Echauz et al. |
| 8,805,527 B2 | 8/2014 | Mumford et al. |
| 8,818,481 B2 | 8/2014 | Bly et al. |
| 8,849,390 B2 | 9/2014 | Echauz et al. |
| 8,868,172 B2 | 10/2014 | Leyde et al. |
| 8,870,764 B2 | 10/2014 | Rubin |
| 9,186,083 B2 | 11/2015 | Osvath |
| 9,241,649 B2 | 1/2016 | Kumar et al. |
| 9,439,599 B2 | 9/2016 | Thompson et al. |
| 9,459,089 B2 | 10/2016 | Ganton et al. |
| 10,206,591 B2 | 2/2019 | Osario et al. |
| 10,285,646 B1 | 5/2019 | Grant et al. |
| 10,342,451 B2 | 7/2019 | Girouard et al. |
| 10,448,839 B2 | 10/2019 | Shivkumar |
| 10,463,270 B2 | 11/2019 | Leyde |
| 10,571,541 B2 | 2/2020 | Grodzki |
| 10,736,525 B2 | 8/2020 | Cardenas et al. |
| 10,743,809 B1 | 8/2020 | Kamousi |
| 10,929,753 B1 | 2/2021 | Nierenberg et al. |
| 10,980,469 B2 | 4/2021 | Girouard et al. |
| 10,986,465 B2 | 4/2021 | Patel et al. |
| 11,020,035 B2 | 6/2021 | Dudek et al. |
| 11,026,628 B1 | 6/2021 | Bruinsma et al. |
| 11,160,505 B2 | 11/2021 | Gunasekar et al. |
| 11,633,139 B2 | 4/2023 | Dudek et al. |
| 11,633,144 B2 | 4/2023 | Elwood et al. |
| 11,638,551 B2 | 5/2023 | Elwood et al. |
| 11,779,262 B2 | 10/2023 | Elwood et al. |
| 11,786,167 B2 | 10/2023 | Elwood et al. |
| 11,857,330 B1 | 1/2024 | Frankel et al. |
| 2002/0013565 A1 | 1/2002 | Cinelli et al. |
| 2002/0035338 A1 | 3/2002 | Dear et al. |
| 2002/0103512 A1 | 8/2002 | Echauz et al. |
| 2002/0109621 A1 | 8/2002 | Khair et al. |
| 2002/0188216 A1 | 12/2002 | Kayyali et al. |
| 2003/0074033 A1 | 4/2003 | Pless et al. |
| 2003/0135128 A1 | 7/2003 | Suffin et al. |
| 2003/0195429 A1 | 10/2003 | Wilson |
| 2004/0068199 A1 | 4/2004 | Echauz et al. |
| 2004/0079372 A1 | 4/2004 | John et al. |
| 2005/0165323 A1 | 7/2005 | Mongomery et al. |
| 2005/0261559 A1 | 11/2005 | Mumford et al. |
| 2006/0111644 A1 | 5/2006 | Guttag et al. |
| 2007/0032733 A1 | 2/2007 | Burton |
| 2007/0032737 A1 | 2/2007 | Causevic et al. |
| 2007/0100666 A1 | 5/2007 | Stivoric et al. |
| 2007/0249952 A1 | 10/2007 | Rubin et al. |
| 2007/0270678 A1 | 11/2007 | Fadem et al. |
| 2008/0082019 A1 | 4/2008 | Ludving et al. |
| 2008/0082020 A1 | 4/2008 | Collura |
| 2008/0091089 A1 | 4/2008 | Guillory et al. |
| 2008/0091090 A1 | 4/2008 | Guillory et al. |
| 2008/0125669 A1 | 5/2008 | Suffin et al. |
| 2008/0146958 A1 | 6/2008 | Guillory et al. |
| 2008/0208008 A1 | 8/2008 | Turner |
| 2008/0243022 A1 | 10/2008 | Donnett et al. |
| 2008/0275327 A1 | 11/2008 | Faarbaek et al. |
| 2008/0294031 A1 | 11/2008 | Wilson et al. |
| 2008/0319277 A1 | 12/2008 | Bradley |
| 2009/0054737 A1 | 2/2009 | Magar et al. |
| 2009/0124923 A1 | 4/2009 | Sackellares et al. |
| 2009/0137923 A1 | 5/2009 | Suffin et al. |
| 2009/0157662 A1 | 6/2009 | Suffin et al. |
| 2010/0143256 A1 | 6/2010 | Suffin et al. |
| 2010/0145217 A1 | 6/2010 | Otto et al. |
| 2010/0168603 A1 | 7/2010 | Himes et al. |
| 2010/0222686 A1 | 9/2010 | Fisher et al. |
| 2010/0234697 A1 | 9/2010 | Walter et al. |
| 2010/0298735 A1 | 11/2010 | Suffin |
| 2011/0015495 A1 | 1/2011 | Dothie et al. |
| 2011/0098593 A1 | 4/2011 | Low et al. |
| 2011/0218820 A1 | 9/2011 | Himes et al. |
| 2011/0221590 A1 | 9/2011 | Baker et al. |
| 2011/0279963 A1 | 11/2011 | Kumar et al. |
| 2012/0003933 A1 | 1/2012 | Baker et al. |
| 2012/0035451 A1 | 2/2012 | Jaffe et al. |
| 2012/0179062 A1 | 7/2012 | Wilson |
| 2012/0209102 A1 | 8/2012 | Ylotalo et al. |
| 2012/0253163 A1 | 10/2012 | Afanasewicz et al. |
| 2012/0310070 A1 | 12/2012 | Kumar et al. |
| 2012/0330125 A1 | 12/2012 | Wilson et al. |
| 2013/0012830 A1 | 1/2013 | Leininger et al. |
| 2013/0310676 A1 | 11/2013 | Jung |
| 2013/0318546 A1 | 11/2013 | Kothuri et al. |
| 2013/0338473 A1 | 12/2013 | Bohorquez et al. |
| 2014/0012151 A1 | 1/2014 | Nierenberg et al. |
| 2014/0012509 A1* | 1/2014 | Barber ............... G06F 3/013 702/19 |
| 2014/0051044 A1 | 2/2014 | Badower et al. |
| 2014/0121557 A1 | 5/2014 | Gannon et al. |
| 2014/0148872 A1 | 5/2014 | Goldwasser et al. |
| 2014/0206975 A1 | 7/2014 | Lang |
| 2014/0206977 A1 | 7/2014 | Bahney et al. |
| 2014/0210627 A1 | 7/2014 | Nothacker et al. |
| 2014/0247058 A1 | 9/2014 | Mortara |
| 2014/0313052 A1 | 10/2014 | Yarger et al. |
| 2015/0038870 A1 | 2/2015 | Yoo et al. |
| 2015/0088024 A1 | 3/2015 | Sackellares et al. |
| 2015/0134580 A1 | 5/2015 | Wilson |
| 2015/0142082 A1 | 5/2015 | Simon et al. |
| 2015/0150505 A1 | 6/2015 | Kaskoun et al. |
| 2015/0216436 A1 | 8/2015 | Bosl et al. |
| 2015/0289814 A1 | 10/2015 | Magar et al. |
| 2015/0351690 A1 | 12/2015 | Toth et al. |
| 2015/0374255 A1 | 12/2015 | Vasapollo |
| 2016/0000382 A1 | 1/2016 | Jain et al. |
| 2016/0022161 A1 | 1/2016 | Khair |
| 2016/0029958 A1 | 2/2016 | Le et al. |
| 2016/0089049 A1 | 3/2016 | Hung et al. |
| 2016/0256111 A1 | 9/2016 | Cheng et al. |
| 2016/0270679 A1 | 9/2016 | Mahon et al. |
| 2016/0287127 A1 | 10/2016 | Kesinger et al. |
| 2016/0374583 A1 | 12/2016 | Cerruti et al. |
| 2017/0055896 A1 | 3/2017 | Al-Ali et al. |
| 2017/0076217 A1 | 3/2017 | Krumm et al. |
| 2017/0095176 A1 | 4/2017 | Sun et al. |
| 2017/0156622 A1 | 6/2017 | Mahoor et al. |
| 2017/0169128 A1* | 6/2017 | Batchu Krishnaiahsetty ............... H04N 21/8456 |
| 2017/0172414 A1 | 6/2017 | Nierenberg et al. |
| 2017/0215759 A1 | 8/2017 | Dudek et al. |
| 2017/0264792 A1* | 9/2017 | Lee ............... G06F 3/1423 |
| 2017/0296083 A1 | 10/2017 | Cardenas et al. |
| 2018/0085000 A1 | 3/2018 | Weffers-Albu et al. |
| 2018/0110466 A1 | 4/2018 | Ralston |
| 2018/0189678 A1* | 7/2018 | Gupta ............... G05D 1/0088 |
| 2018/0206776 A1 | 7/2018 | Nogueira et al. |
| 2018/0353084 A1 | 12/2018 | Wainright et al. |
| 2019/0059770 A1 | 2/2019 | Gunasekar et al. |
| 2019/0126033 A1 | 5/2019 | Pradeep |
| 2019/0371478 A1 | 12/2019 | Rondoni et al. |
| 2019/0380583 A1 | 12/2019 | Danneels et al. |
| 2020/0163629 A1 | 5/2020 | Dearing et al. |
| 2020/0229706 A1 | 7/2020 | Nishimura et al. |
| 2020/0237248 A1 | 7/2020 | Willis et al. |
| 2020/0315537 A1 | 10/2020 | Magar |
| 2021/0169417 A1 | 6/2021 | Burton |
| 2021/0220064 A1* | 7/2021 | Kottenstette ............ G06F 17/11 |
| 2021/0244335 A1 | 8/2021 | Dudek et al. |
| 2021/0282701 A1 | 9/2021 | Chan et al. |

(56) References Cited

U.S. PATENT DOCUMENTS

| | | |
|---|---|---|
| 2021/0307672 A1 | 10/2021 | Elwood et al. |
| 2021/0353224 A1 | 11/2021 | Etkin et al. |
| 2021/0375480 A1 | 12/2021 | Mahon et al. |
| 2022/0031248 A1 | 2/2022 | Grant et al. |
| 2022/0039720 A1 | 2/2022 | Abercombie, II et al. |
| 2022/0338780 A1 | 10/2022 | Dudek et al. |
| 2022/0338789 A1 | 10/2022 | Elwood et al. |
| 2022/0338790 A1 | 10/2022 | Elwood et al. |
| 2022/0338791 A1 | 10/2022 | Elwood et al. |
| 2022/0338792 A1 | 10/2022 | Elwood et al. |
| 2022/0338793 A1 | 10/2022 | Elwood et al. |
| 2022/0346695 A1 | 11/2022 | Elwood et al. |
| 2022/0346700 A1 | 11/2022 | Elwood et al. |
| 2023/0255541 A1 | 8/2023 | Elwood et al. |
| 2023/0404471 A1 | 12/2023 | Elwood et al. |

FOREIGN PATENT DOCUMENTS

| | | | |
|---|---|---|---|
| WO | WO 2005/109334 A2 | 11/2005 | |
| WO | WO 2010/107928 A2 | 9/2010 | |
| WO | WO 2015/055156 A1 | 4/2015 | |
| WO | WO-2018013569 A1 * | 1/2018 | ........... A61B 5/0022 |
| WO | WO 2018/218174 A1 | 11/2018 | |
| WO | WO 2019/046799 A1 | 3/2019 | |
| WO | WO-2022228668 A1 * | 11/2022 | |

OTHER PUBLICATIONS

Jia et al., Design of a Wireless EEG System for Point-of-Care Applications. Proc IEEE Annu Northeast Bioeng Conf. Apr. 2013; 2013: 78-79.

Saputro et al., Seizure Type Classification on EEG Signal using Support Vector Machine. IOP Conf. Series: J Phys Conf. Series (2019) 1201: 012065 in 8 pages.

Prabhu K.M.M., Window Functions and Their Applications in Signal Processing. ISBN-13:978-1-4665-1583-3; Taylor & Francis; 2014; in 405 pages.

Frankel et al., Electrographic Seizure Monitoring with a Novel, Wireless, Single-Channel EEG Sensor. Clin Neurophys Practice. Jan. 1, 2021;6: 172-178.

Ren K., "What You Need to Know About Periodic Advertising Sync Transfer". Bluetooth Low Energy, Broadcast, Connected Device, Location Services; Feb. 28, 2019; 4 pages.

Vandecasteele et al., "Visual Seizure Annotation and Automated Seizure Detection Using Behind-the-ear electroencephalographic Channels". Epilepsia. Apr. 2020;61(4): 766-775.

* cited by examiner

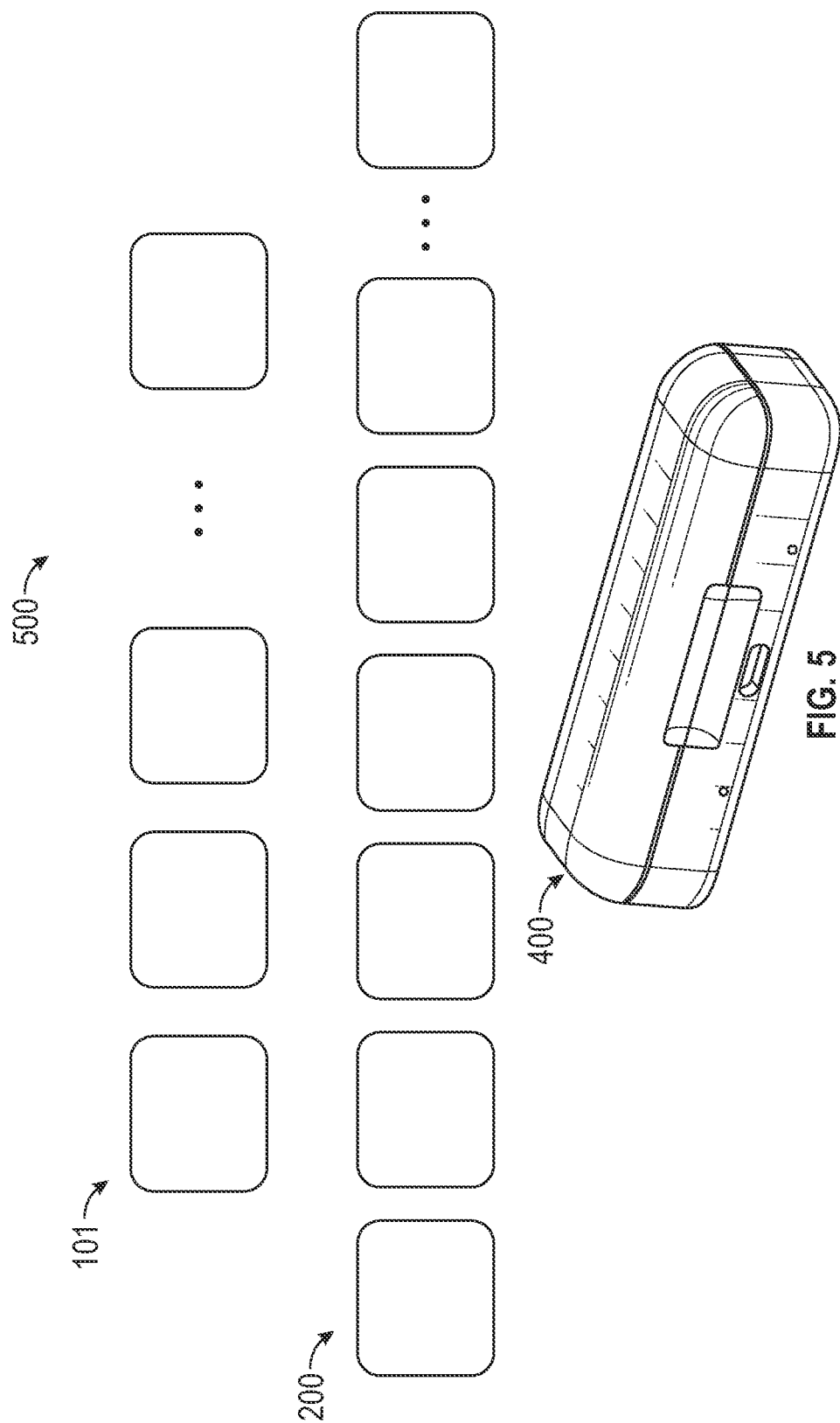

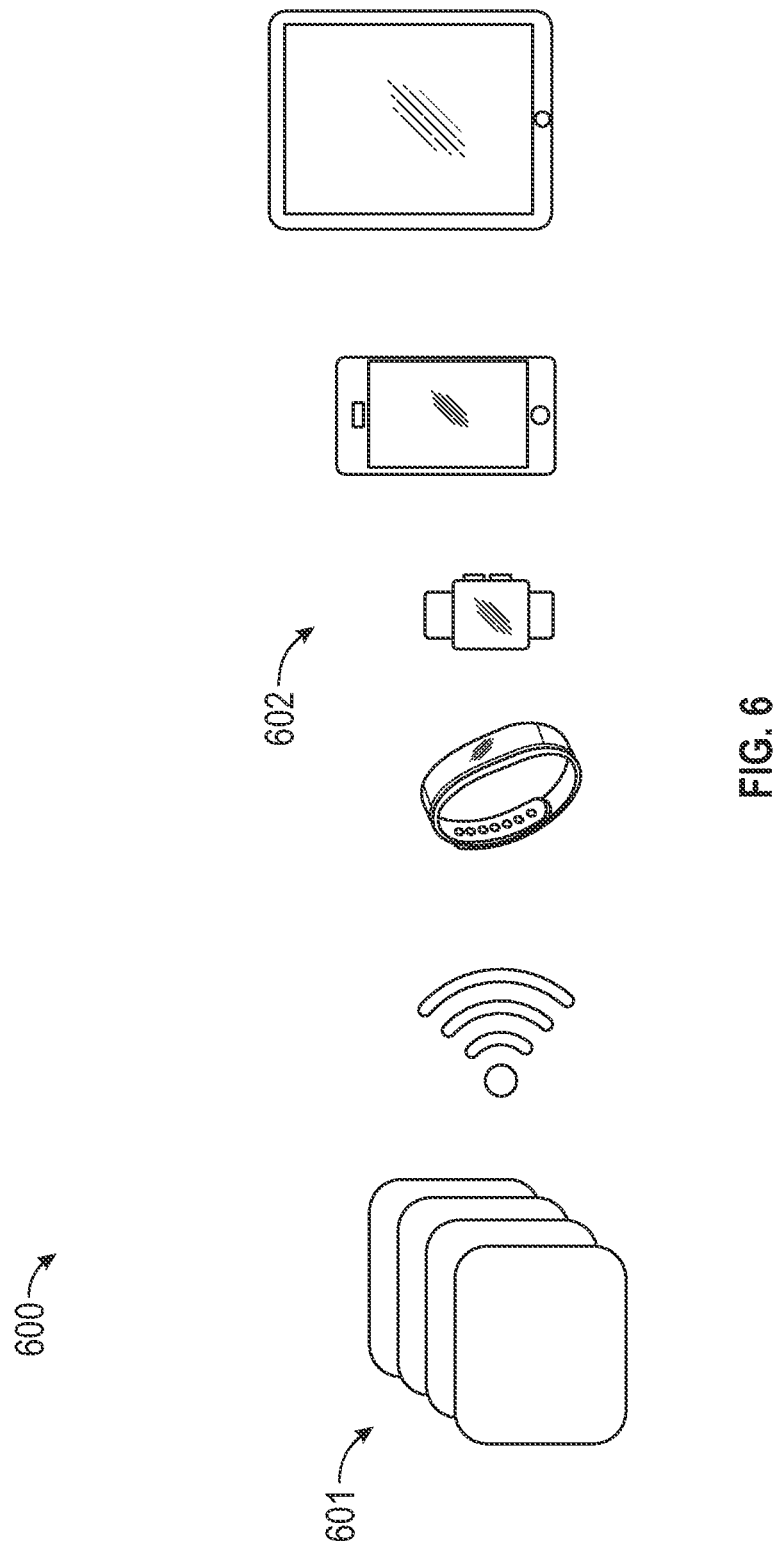

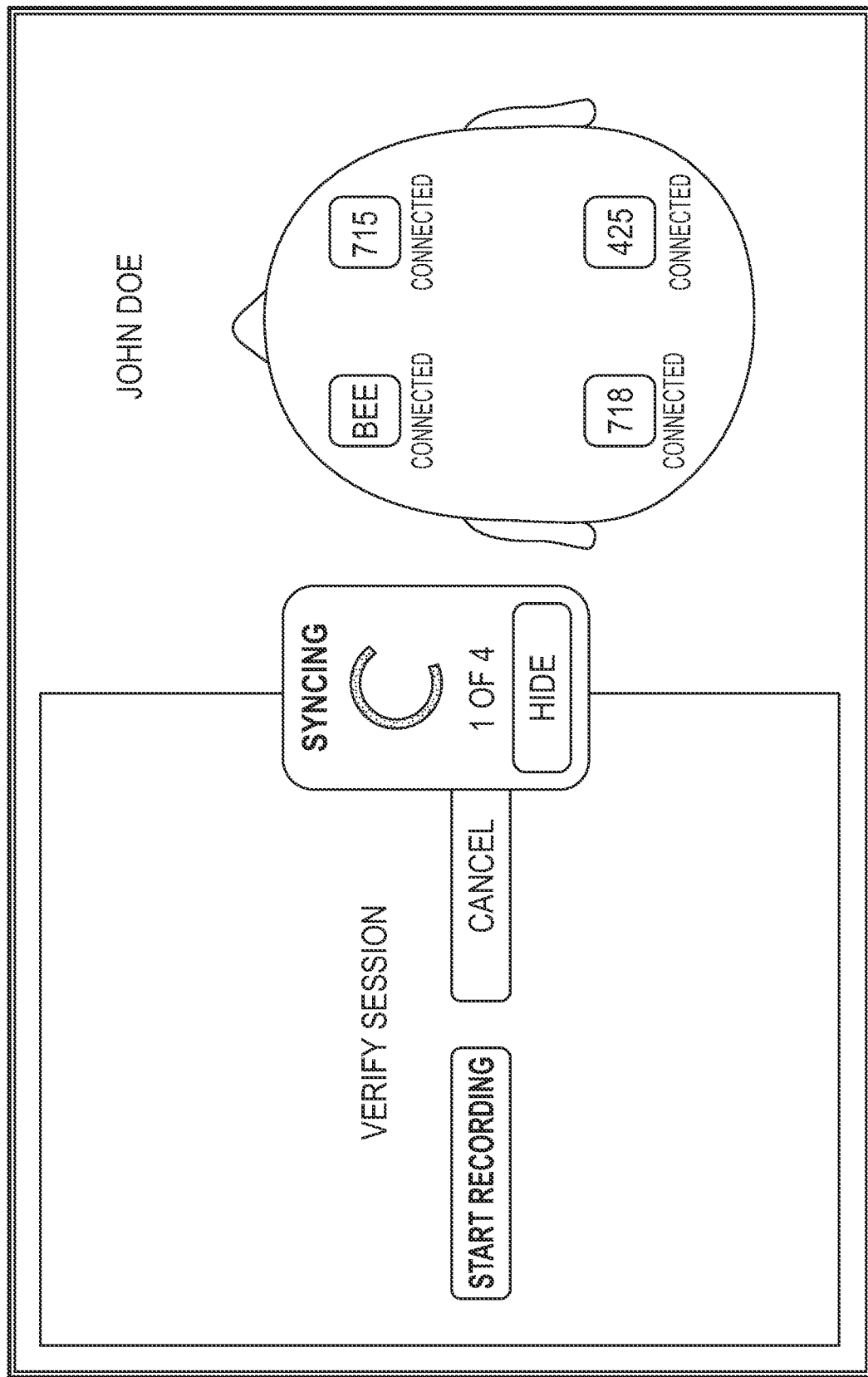

SYSTEMS AND METHODS FOR ELECTROENCEPHALOGRAM MONITORING

CROSS-REFERENCE TO RELATED APPLICATIONS

This application claims priority to U.S. Provisional Patent Application No. 63/380,132 filed on Oct. 19, 2022, which is incorporated by reference in its entirety.

STATEMENT REGARDING FEDERALLY SPONSORED R&D

This invention was made with Government support under Grant Nos. 1U44NS1215621 and 1R43NS100235, awarded by the Department of Health and Human Services. The Government has certain rights in the invention.

TECHNICAL FIELD

This application relates to systems and methods for monitoring brain activity using one or more wireless electroencephalogram sensors.

BACKGROUND

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

There are thousands of hospitals across the United States. Many of these hospitals are community or rural hospitals. These community or rural hospitals conventionally are part of a hospital system or network. An example of one such network includes several community hospitals with one major tertiary hospital. A community or rural hospital outside of any large hospital network would typically contract with a large tertiary hospital for emergent and intensive-care solutions outside of the areas of expertise of the community or rural hospital.

EEG monitoring is conventionally only available in the large tertiary hospitals that support a neurology department with an EEG service. Many hospitals do not offer EEG monitoring. These hospitals make arrangements with larger tertiary hospitals or their partners when such monitoring is required or desirable for patients. This conventionally takes the form of a referral of the patient to the tertiary hospital for expert of specialist services. Often this includes travel or transport of the patient to the tertiary hospital for services. This creates many problems particularly for patients in rural areas. As a result, it is desirable to provide improvements in EEG monitoring systems and methods.

SUMMARY

An EEG can be performed to diagnose epilepsy, verify problems with loss of consciousness or dementia, verify brain activity for a person in a coma, study sleep disorders, monitor brain activity during surgery, and monitor additional physical problems.

Disclosed herein are systems and methods for monitoring brain activity using one or more wireless EEG sensors configured to be removably placed in one or more locations on a scalp of a patient. One or more computing devices can communicate with the EEG sensors and facilitate setting up the EEG sensors, receiving, and processing EEG data collected by the EEG sensors. Advantageously, accurate EEG measurements can be obtained and processed to determine one or more physiological conditions of a patient, such as seizures, epilepsy, or the like. In addition, disclosed systems and method allow non-experts to set-up EEG monitoring so that a much larger patient population can benefit from the monitoring.

BRIEF DESCRIPTION OF THE DRAWINGS

In the following description, various implementations will be described. For purposes of explanation, specific configurations and details are set forth in order to provide a thorough understanding of the implementations. However, it will also be apparent to one skilled in the art that the implementations may be practiced without the specific details. Furthermore, well-known features may be omitted or simplified in order not to obscure the implementation being described.

FIG. 5 illustrates a kit or system for monitoring brain activity.

FIG. 6 is an illustration of an EEG monitoring system.

FIGS. 7B to 7K illustrate example screens associated with sensor activation and sensor placement displayed on a portable computing device.

DETAILED DESCRIPTION

Overview

Certain EEG monitoring systems can include complicated multi-component medical device systems, which require technical skill for set-up and coordination. When such systems are used outside of a large or research hospital with special expertise, set-up and coordination can be difficult and prone to user error. EEG monitoring systems which use multiple sensor components also require time synchronization across individual devices in order to combine sensor data. When the devices are not wired together, achieving time synchronization of sensor across multiple sensor devices can be difficult to achieve. EEG monitoring systems may also be used for long-term use, either at home or in a hospital of any given size or specialty including, for example, small general hospitals in rural areas. Long-term EEG recording requires a high level of complexity in set up and coordination but needs to be seamless and simple for day-to-day use.

EEG monitoring systems and methods have been described in U.S. Pat. No. 11,020,035 and in U.S. Patent Publication No. 2021/0307672, each of which are incorporated by reference in their entirety.

Described herein are improved systems, kits, and methods for EEG monitoring.

Wearable Sensor and EEG Monitoring Kit

Figure 1A:
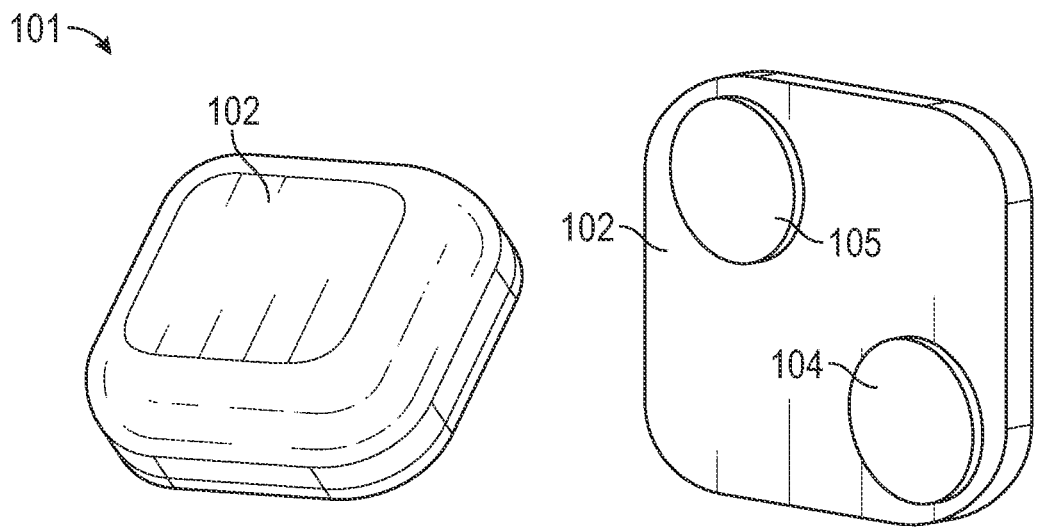
FIG. 1A is a perspective top view and bottom view illustration of an EEG recording wearable sensor.

FIG. 1A is a perspective top view and bottom view illustration of an EEG recording wearable sensor 101, which can be used as a seizure monitoring tool. As shown in FIG. 1A, the wearable sensor 101 is self-contained in a housing 102. The housing 102 may be formed of a plastic, polymer, composite, or the like that is water-resistant, waterproof, or the like.

The housing 102 can contain all of the electronics for recording EEG from at least two electrodes 104, 105. The electrodes 104, 105 are on the bottom, or scalp facing, side shown on the right side of FIG. 1A. Electrodes 104, 105 may be formed of any suitable material. For example, electrodes 104, 105 may comprise gold, silver, silver-silver chloride, carbon, combinations of the foregoing, or the like. One of the electrodes 104, 105 can be a reference electrode and the other can be a measurement (or measuring) electrode. As noted above, the entire wearable sensor 101 may be self-contained in a watertight housing 102. The wearable sensor 101 can be designed to be a self-contained EEG machine that is one-time limited use per user and disposable. The wearable sensor 101 can include more than two electrodes. In some cases, the wearable sensor 101 includes three electrodes. In some implementations, the wearable sensor 101 includes four electrodes. Additional electrodes (such as a third and/or fourth electrode) may be formed of any suitable material, for example gold, silver, silver-silver chloride, carbon, combinations of the foregoing, or the like.

The wearable sensor 101 has two electrodes 104, 105 and can be used alone or in combination with other wearable sensors 101 (such as, three other wearable sensors 101) as a discrete tool to monitor seizures (and in some cases count seizures). It may be desirable, but not necessary, that the user has had a previous diagnosis of a seizure disorder using a traditional wired EEG based on the 10-20 montage. This diagnosis provides clinical guidance as to the most optimal location to place the wearable sensor 101 for recording electrographic seizure activity in an individual user. In some cases, the electrode 104, 105 spacing uses a bipolar derivation to form a single channel of EEG data.

Figure 1B:
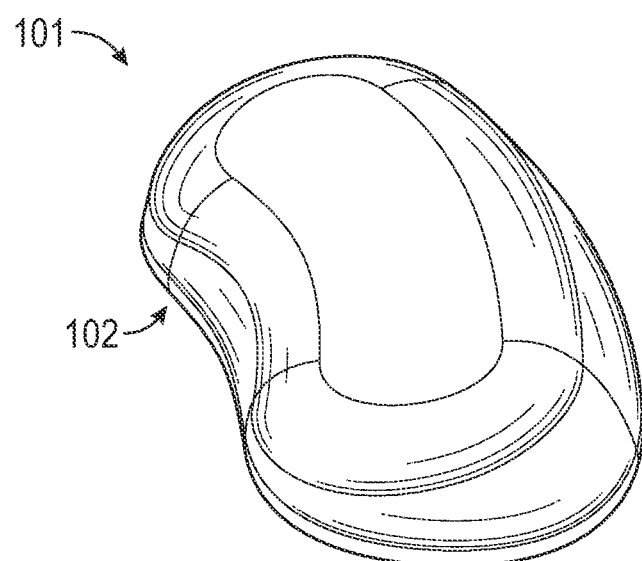
FIGS. 1B to 1D are various views of an EEG recording wearable sensor.

FIG. 1B is a perspective top view illustration of an EEG recording wearable sensor 101 with a housing 102 that has an extended, rounded shape. Such shape can be referred to as a jellybean shape, and may facilitate accurate placement on a patient in a correct orientation as well as promote patient comfort and prolonged wear.

Figure 1C:
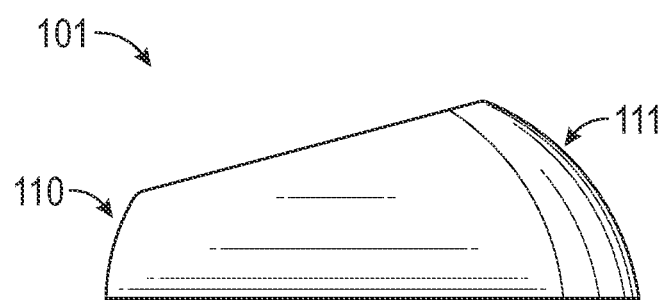
Figure 1D:
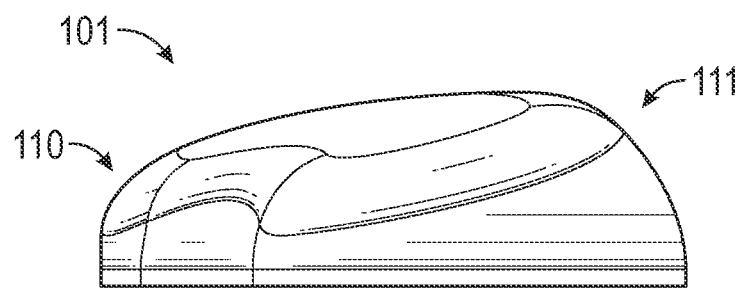

In some cases, the EEG recording wearable sensor 101 is shaped to fit behind the ear. The EEG recording wearable sensor 101 can be shaped to fit along the hairline. The EEG recording wearable sensor 101 can be shaped to fit along a scalp. For example, as shown in FIG. 1B, the EEG recording wearable sensor 101 has an extended rounded shape which is configured to fit around or complement a hairline of a user, such that the extended, rounded shape of the housing 102 facilitates unobtrusive wear of the sensor on the scalp of the user while facilitating collection of the EEG signals. In some implementations, the housing 102 includes a narrow portion configured to curve around the hairline of a user. FIG. 1C provides a cross-sectional view, and FIG. 1D provides a perspective view of the EEG recording wearable sensor 101 of FIG. 1B. FIGS. 1C-1D illustrate that the housing 102 includes a narrow portion 110. The side of the housing 102 with the narrow portion 110 can be positioned closer to the patient's ear (see FIG. 2C), which can facilitate unobtrusive wear and collection of the EEG signals. The narrow portion 110 can be thinner than other parts of the housing 102. The housing 102 can become thicker (or widen) from the end that includes the narrow portion 110 to the opposite end 111. Such varying thickness of the housing 102 can facilitate unobtrusive wear. Thickness of the housing 102 in the widest portion can be about 10.0 mm, 9.5 mm, 9.0 mm, 8.5 mm, 8.0 mm, 7.5 mm, 7.0 mm, 6.5 mm, 6.0 mm, 5.5 mm, 5.0 mm, 4.5 mm, 4.0 mm, or within a range constructed from any of the aforementioned values.

In some implementations, the EEG recording wearable sensor 101 is shaped to mimic the look of hearing aids. The EEG recording wearable sensor 101 can include an antenna. The external design (jellybean shape) of the EEG recording wearable sensor 101 can influence the internal shape, requiring unique design and tuning of the antenna.

In some cases, the EEG recording wearable sensor 101 includes a power source supported by the housing and configured to provide power to the electronic circuitry. In some cases, the EEG recording wearable sensor 101 includes a rechargeable battery. The EEG recording wearable sensor 101 can includes electrode. The EEG recording wearable sensor 101 can include at least two electrodes positioned on an exterior surface of the housing and configured to detect EEG signals indicative of a brain activity of the user when the housing is positioned on a scalp of the user. The electrodes may be disposed within the housing 102 of the EEG recording wearable sensor 101. Unlike traditional wired EEG systems employing the 10-20 montage, the EEG recording wearable sensor 101 can allow a much smaller spacing between the measurement and reference electrodes, which may not only make the housing 102 more compact, but also improve signal quality. The distance between the electrodes can be configured to allow for less noisy EEG signal capture, thus improving signal quality. The distance between the electrodes can be reduced, particularly when compared to traditional wired EEG systems employing the 10-20 montage. The distance between electrodes can be no more than about 25 mm center to center, no more than about 20 mm center to center, no more than about 18 mm center to center, no more than about 15 mm center to center, no more than about 10 mm center to center, or within a range constructed from any of the aforementioned values. The housing 102 can be configured so that the electrodes are disposed at a distance configured to allow better EEG signal capture.

The EEG recording wearable sensor 101 includes an electronic circuitry that may be supported by the housing 102. The electronic circuitry can be configured to process the EEG signals detected by the at least two electrodes. In some implementations, the electronic circuitry is configured to wirelessly communicate processed EEG signal to a remote computing device. The remote computing device can be a portable computing device as described herein.

An extended, rounded shape for an EEG recording wearable sensor 101 may allow an EEG recording wearable sensor 101 to provide: (a) proper electrode pair spacing to allow EEG signal capture; (b) an enclosed housing 102 large enough to contain a full electronics package, including an antenna and a battery that supports frequent communication (such as, Bluetooth or Bluetooth low energy (BLE)); and/or (c) a housing 102 design that complements the curvature around a scalp and/or a hairline and/or behind ears.

In some cases, the surface area of the housing 102 is about 8.5 $cm^2$, 8.0 $cm^2$, 7.5 $cm^2$, 7.0 $cm^2$, 6.5 $cm^2$, 6.0 $cm^2$, 5.5 $cm^2$, 5.0 $cm^2$, 4.5 $cm^2$, or within a range constructed from any of the aforementioned values. The surface area of the jellybean shaped housing 102 illustrated in FIG. 1B can be about 20 $cm^2$, 19.5 $cm^2$, 19.0 $cm^2$, 18.5 $cm^2$, 18.0 $cm^2$, 17.5 $cm^2$, 17.0 $cm^2$, 16.5 $cm^2$, 16.0 $cm^2$, 15.5 $cm^2$, 15.0 $cm^2$, 14.5 $cm^2$, 14.0 $cm^2$, 13.5 $cm^2$, 13.0 $cm^2$, 12.5 $cm^2$, 12.0 $cm^2$, 11.5 $cm^2$, 11.0 $cm^2$, 10.5 $cm^2$, 10.0 $cm^2$, 9.5 $cm^2$, 9.0 $cm^2$, 8.5 $cm^2$, 8.0 $cm^2$, 7.5 $cm^2$, 7.0 $cm^2$, 6.5 $cm^2$, 6.0 $cm^2$, 5.5 $cm^2$, 5.0 $cm^2$, 4.5 $cm^2$ or less, or within a range constructed from any of the aforementioned values. The volume of the jellybean shaped housing 102 illustrated in FIG. 1B can be about 8.0 $cm^3$, 7.5 $cm^3$, 7.0 $cm^3$, 6.5 $cm^3$, 6.0 $cm^3$, 5.0 $cm^3$, 4.5 $cm^3$, 4.0 $cm^3$, 3.5 $cm^3$, 3.0 $cm^3$, 2.5 $cm^3$, 2.0 $cm^3$ or less, or within a range constructed from any of the aforementioned values. The wearable sensor 101 can be placed anywhere on the scalp of a patient to record EEG (such as, behind the ear).

The wearable sensor 101 may be packaged such that removal from the package activates the circuitry. Implementations of the wearable sensor 101 can be placed anywhere on the scalp as placing a conventional wired EEG electrode. The wearable sensor 101 can self-adhere to the scalp either through a conductive adhesive, an adhesive with a conductive, and/or through mechanical means such as intradermal fixation with a memory-shape metal, or the like.

Once attached to the scalp (for instance, with an attachment as described below), some implementations enable the wearable sensor 101 to perform as seizure detection device (alone or in combination with one or more other wearable sensors 101, such as three other wearable sensors 101). The wearable sensor 101 can record EEG continuously, uninterrupted for up to seven days. In some implementations, each EEG recording wearable sensor 101 is configured to detect EEG signals independent of the other sensors. Following a recording session, the wearable sensor 101 may be placed in the mail and returned to a service that reads the EEG to identify epileptiform activity according to ACNS guidelines. In some cases, data may be retrieved from the wearable sensor 101 via an I/O data retrieval port (not shown) and uploaded or otherwise sent to a service for reading the EEG data. The I/O data retrieval port may operate with any suitable I/O protocol, such as USB protocol, Bluetooth protocol, or the like. Epileptiform activity such as seizures and interictal spikes may be identified in a report along with EEG recording attributes and made available to physicians through a user's electronic medical records, or the like.

The wearable sensor 101 may employ capacitive coupling as a means to spot-check signal quality. A handheld, or other device, can be brought near the wearable sensor 101 to capacitively couple with the device as a means to interrogate the EEG or impedance signal in real time.

The wearable sensor 101 may be used to alert to seizures in real time, or near real time. The wearable sensor 101 may continuously transmit to a base station (not shown) that runs seizure detection algorithm(s) in real-time. The base station may sound an alarm if a seizure is detected either at the base station itself, or through communication to other devices (not shown) capable of providing a visual and/or audio and/or tactile alarm. The base station may also keep a record of EEG for later review by an epileptologist. These EEG may also be archived in electronic medical records, or otherwise stored.

The wearable sensor 101 could be used to record ultra-low frequency events from the scalp such as cortical spreading depressions. Amplifier circuitry (not shown) may be appropriate for recording DC signals. Alternatively, the amplifier circuitry may be appropriate for recording both DC and AC signals. The wearable sensor 101 may be used after a suspected stroke event as a means to monitor for the presence or absence of cortical spreading depressions and/or seizures or other epileptiform activity. The wearable sensor 101 may be placed on the scalp of a patient by any type of health care provider such as an emergency medical technician, medical doctor, nurse, or the like.

In some implementations, the wearable sensor 101 may employ capacitive coupling to monitor for cortical spreading depressions in real time. The spreading depressions could be analyzed over time and displayed as a visualization of the EEG. The wearable sensor 101 may store these EEG (e.g., in storage) for later retrieval. These EEG could also be archived in electronic medical records, or the like.

Figure 2A:
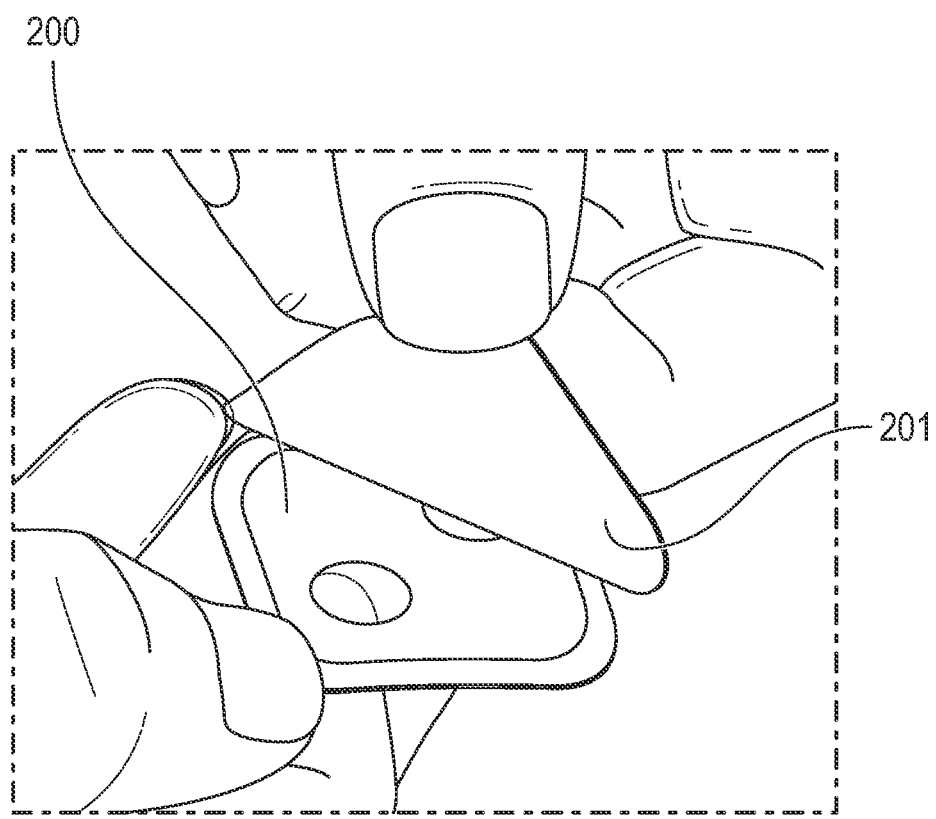
FIG. 2A illustrates an example attachment.
Figure 2B:
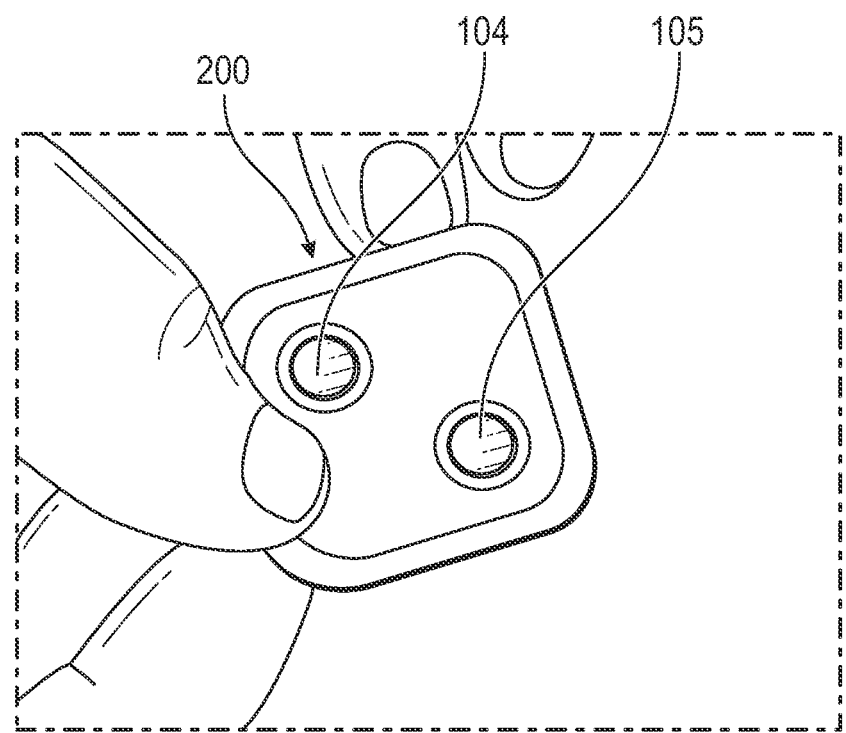
FIG. 2B illustrates an example attachment placed onto the wearable sensor, aligned over the electrodes.

FIG. 2A depicts an attachment 200 being peeled off a backing 201 to reveal an adhesive side. The attachment 200 can be referred to as a sticker or adhesive. The backing 201 may be made of paper, plastic, or any other suitable material. FIG. 2B depicts the attachment 200 placed onto the wearable sensor 101, aligned over the electrodes 104, 105. In some cases, the attachment includes a first side shaped to substantially match the extended, rounded shape and configured to be attached to the exterior surface of the housing 102 of the wearable sensor 101. In some implementations, the attachment includes a second side configured to removably position the wearable sensor 101 on the scalp of a user. A layered attachment 200 may be utilized, which is provided to a user that may remove a layer (the backing 201) to expose an adhesive containing the hydrogel in wells aligned with the positioning of the electrodes (such as electrodes 104, 105). The attachment may then be placed on the sensor, (sensor 101) and thereafter on the user's skin to adhere a sensors such as sensor 101 to the user's skin. Even though the attachment 200 may be illustrated as having rectangular shape, in any of the implementations disclosed herein, the attachment 200 can have a jellybean shape that matches the shape of the housing 102 illustrated in FIG. 1B.

Figure 2C:
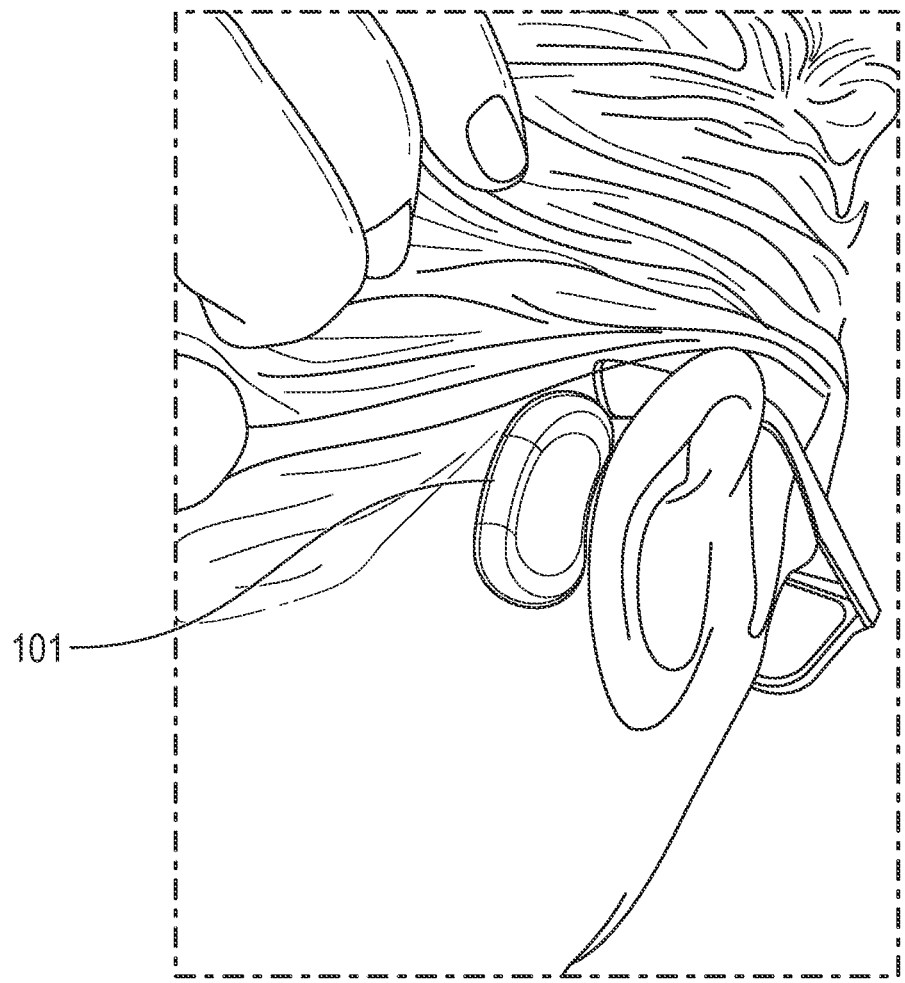
FIG. 2C illustrates an example sensor placed onto a patient's scalp.

FIG. 2C illustrates a sensor 101 placed onto a patient's scalp. The sensor 101 is reversibly attached to the scalp with the attachment 200. The sensor 101 is located at an appropriate place on the user, for example, on the scalp below the hairline, in order to sense and record EEG data. The EEG data may be analyzed on-board, for example, via application of an analysis or machine learning model stored in the sensor 101 or may be analyzed by a local device or remote device or a combination of the foregoing. By way of example, the sensor 101 may communicate using a wired or wireless protocol, for example, secure Bluetooth Low Energy (BLE), to a local device using a personal area network (PAN), such as communicating data to a smartphone or a tablet. Similarly, the sensor 101 may communicate with a remote device using a wide area network (WAN), such as communicating EEG data to a remote server or cloud server over the Internet, with or without communicating via an intermediary device such as a local device.

The hydrogel is conductive and also provides enough adhesion to the scalp for effective recording of EEG for long wear times. Alternatively, the wearable sensor 101 may be adhered with a combination conductive hydrogel with an adhesive construct. After use, the attachment 200 can simply be peeled off the wearable sensor 101 and thrown away. Prior to the next use (for example after a wear period), a new attachment 200 can be applied to the wearable sensor 101.

Consistent EEG signal data from person-to-person is made possible by using a one-piece converted conductive hydrogel and adhesive construct 200. The attachment 200 enables reversable adhesion of the wearable sensor 101 to the scalp. The design of the attachment 200 also reduces both water infiltration and water evaporation from the hydrogel during long wear times. In some cases, the attachment 200 is made by laminating a number of adhesive and non-adhesive layers with wells filled with a hydrogel and sandwiched between release liners. In some implementations, the attachment 200 is further packaged individually in air-tight and water-tight pouches.

Figure 3A:
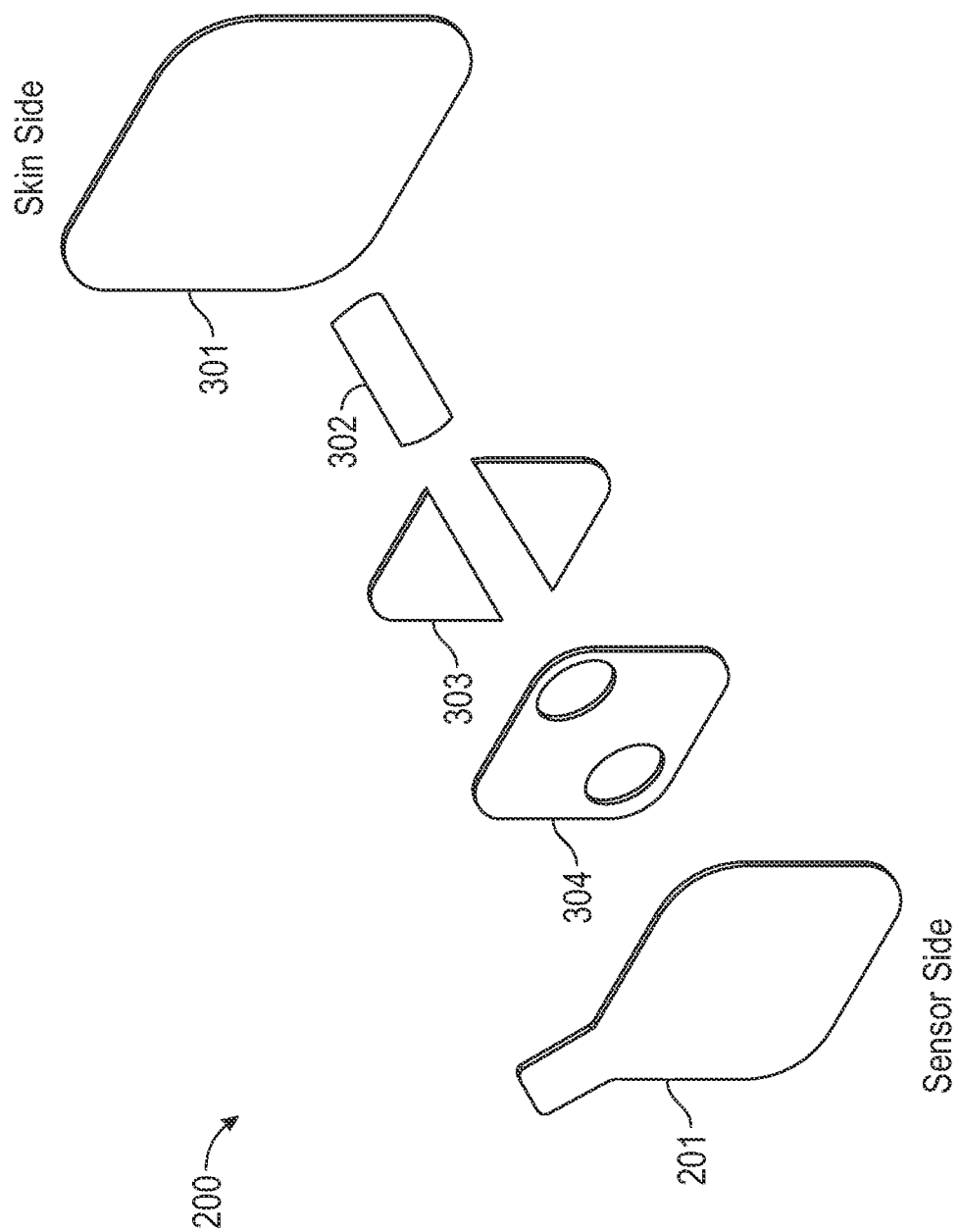
FIGS. 3A to 3C are exploded views of attachments.

FIG. 3A illustrates an exploded view of an attachment 200. In the example of FIG. 3A, attachment 200 includes a clear PET (polyethylene terephthalate) liner 301, a hydrogel 302, a hydrogel 303, a transfer adhesive 304, and a paper backing 201. The attachment 200 may include a first side shaped to substantially match the extended, rounded shape and configured to be attached to the exterior surface of the housing 102 of a wearable sensor 101 (sensor side). In some cases, the first side of the attachment 200 is configured to be attached to a bottom surface of a wearable sensor 101. The attachment 200 may include a second side configured to removably position the wearable sensor 101 on the scalp of the user (skin side). In some implementations, the clear PET liner 301 is configured to be removed before the attachment 200 is placed on the scalp of a user. The hydrogel 302, 303 can facilitate repositioning the wearable sensor 101 on the scalp of the user.

Figure 3B:
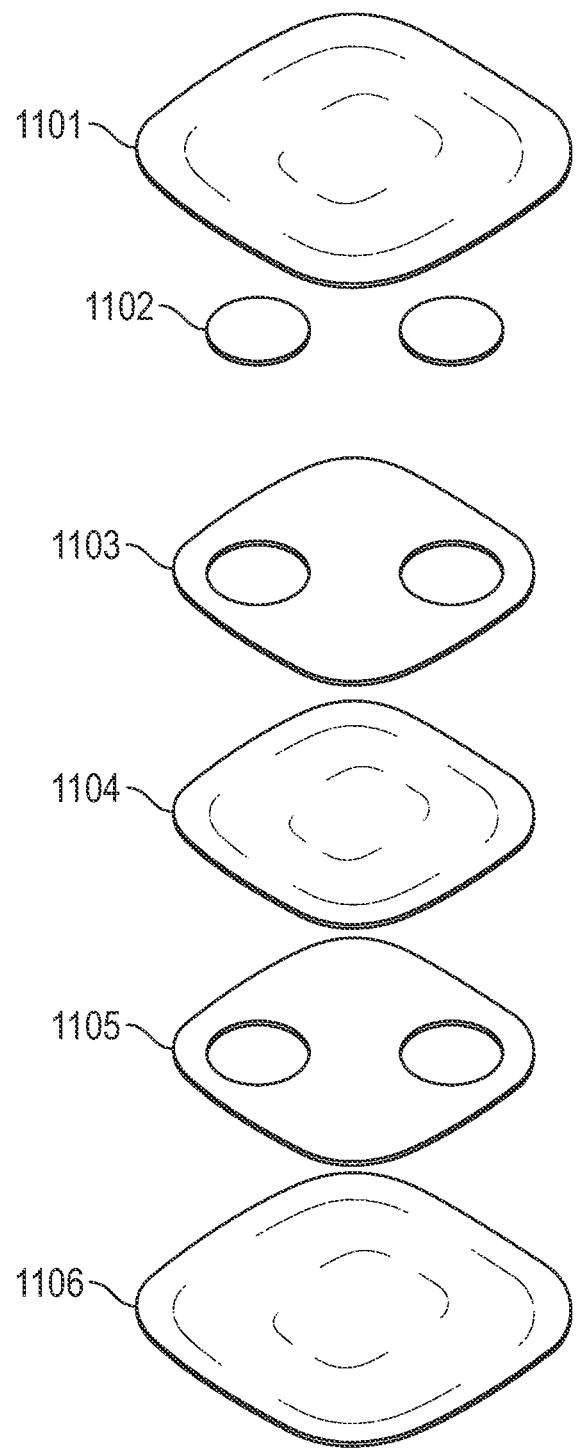

FIG. 3B illustrates an exploded view of an attachment 200. In the example of FIG. 3B, attachment 200 includes layers 1101-1106. The first layer 1101 can include a top liner which may be composed of thermoplastic resin. The thermoplastic resin may be polyethylene terephthalate (PET). In some implementations, second layer 1102 comprises a cured hydrogel. The third layer 1103 can include a transfer adhesive. In some implementations, fourth layer 1104 comprises a non-woven fabric. The non-woven fabric may be scrim-spun lace non-woven polyester. The fifth layer 1105 can include an adhesive. The adhesive may be a thick double-sided adhesive foam. The sixth layer 1106 can include a bottom liner which may be composed of thermoplastic resin. The thermoplastic resin may be PET.

In some cases, two or more of first layer 1101, second layer 1102, third layer 1103, fourth layer 1104, fifth layer 1105, and sixth layer 1106 are laminated to one another such that second layer 1102 is disposed between first layer 1101 and third layer 1103. In some implementations, first layer 1101 is removable. The sixth layer 1106 can be removable.

Third layer 1103 and fifth layer 1105 can form apertures therein. The apertures may align with electrodes of a sensor.

One or more of third layer 1103, fourth layer 1104, and fifth layer 1105 can include a cured hydrogel. The hydrogel can be intermingled with the non-woven fabric of fourth layer 1104. The hydrogel can be transitioned from a liquid or semi-liquid or gel form to a solid or semi-solid form using a crosslinking process. The cross-linking process can be triggered by application of one or more ultraviolet (UV) light and an electron beam.

Provided herein are methods for preparing an attachment 200. In some implementations, the method includes providing two or more layers, at least one of the two or more layers including an aperture. Providing two or more layers can include providing a fabric layer. The fabric can be non-woven. The method can further include stacking the two or more layers. The method can include providing hydrogel to the apertures. Providing hydrogel can include pouring the hydrogel into the apertures. The method can further include fixing the layers. Fixing the hydrogel can include curing the hydrogel via a UV light or an electron beam exposure.

Figure 3C:
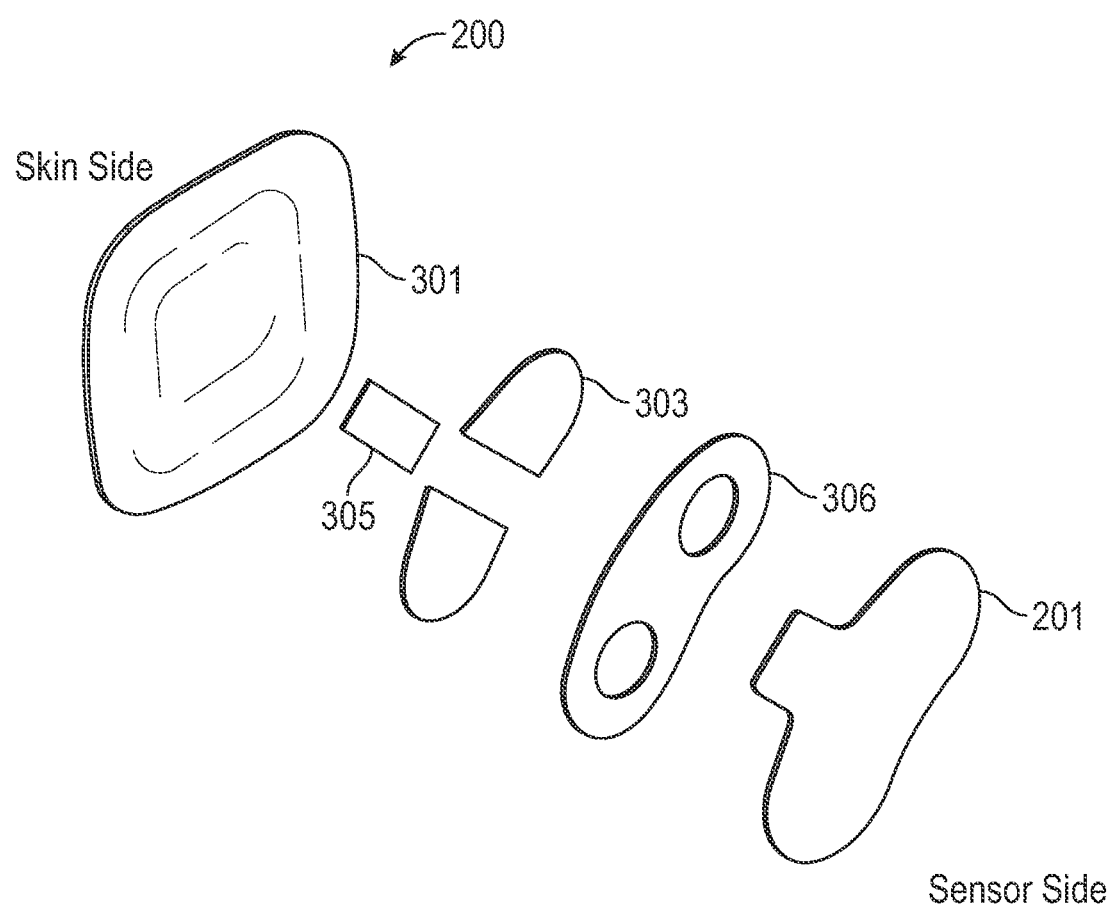

FIG. 3C illustrates an exploded view of an attachment 200. In the example of FIG. 3C, attachment 200 includes a clear PET liner 301, hydrocolloid material 305, a hydrogel 303, a double-coated tape 306, and a paper backing 201. The attachment 200 may include a first side shaped to substantially match the extended, rounded shape and configured to be attached to the exterior surface of the housing 102 of a wearable sensor 101 (sensor side). The first side of the attachment 200 can be configured to be attached to a bottom surface of a wearable sensor 101. The attachment 200 may include a second side configured to removably position the wearable sensor 101 on the scalp of the user (skin side). In some cases, the clear PET liner 301 is configured to be removed before the attachment 200 is placed on the scalp of a user. The hydrocolloid material 305 can facilitate repositioning the wearable sensor 101 on the scalp of the user.

Figure 4:
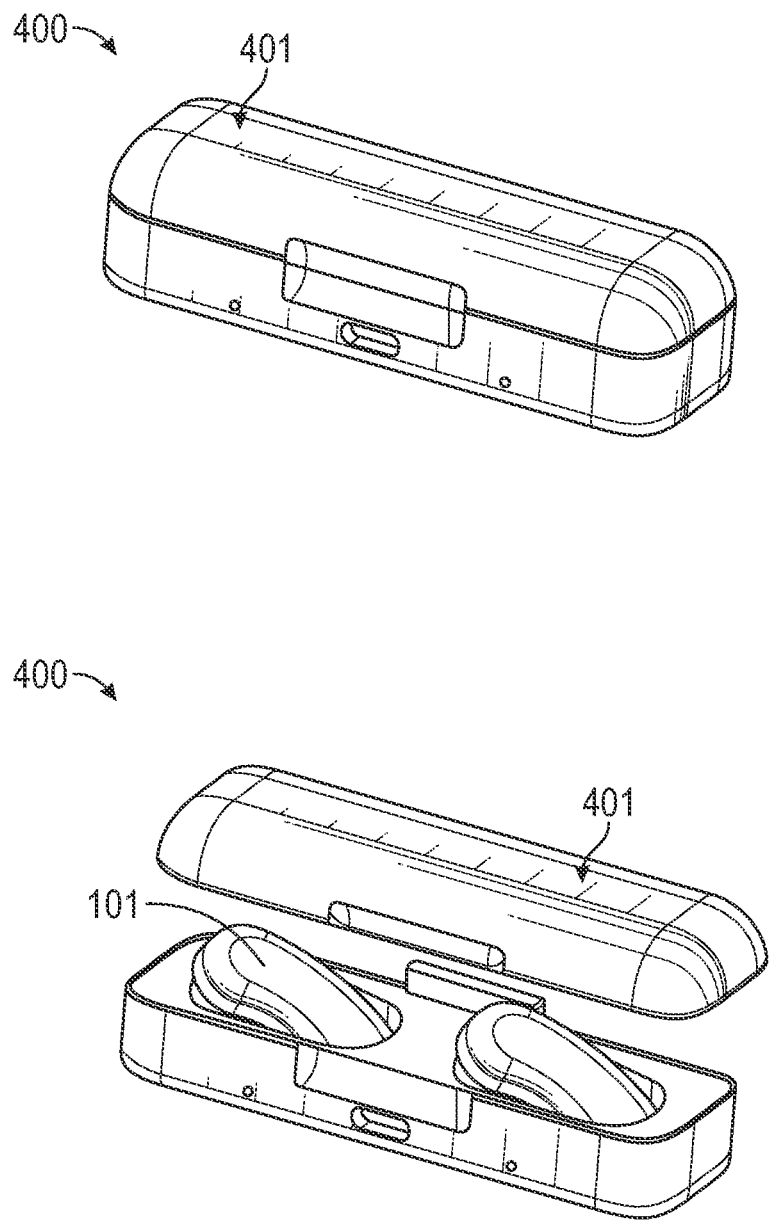
FIG. 4 is a front perspective view illustration of a charger.

FIG. 4 is a front perspective view of a charger 400. FIG. 4 illustrates a charger 400 in a closed configuration (left image) and in an open configuration (right image). The system for monitoring brain activity can include a charger 400 comprising a charger housing 401. The charger housing 401 can be configured to receive and simultaneously charge power sources of at least two wearable sensors 101. For example, the charger 400 may receive and charge power sources for two wearable sensors, or four sensors, or more, 101 at the same time. In some implementations, the charger 400 includes multiple charging stations for wearable sensors 101.

The wearable sensor 101 may be worn continuously for a period of days before it needs to be removed, such as for charging an on-board power source such as a rechargeable battery. To enable continued monitoring, the user may have two (or more) sets of wearable sensors 101 and will use one (or more) while the other(s) is being recharged. Such an arrangement will allow for continuous EEG data capturing and monitoring.

FIG. 5 illustrates a kit or system 500 for monitoring brain activity. In some cases, the kit or system 500 disclosed herein includes a plurality of sensors 101. For example, the kit or system 500 may include 2 sensors, 3 sensors, 4 sensors, 5 sensors, 6 sensors, 7 sensors, 8 sensors, 9 sensors, or 10 sensors, and so on. The kit or system 500 may include two sets of sensors, with a first set for use while a second set is charging. After the first set is used, the first set may be charged while the second set is used. The kit or system 500 disclosed herein can include a plurality of attachments 200.

For example, the kit or system 500 includes 2 attachments, 3 attachments, 4 attachments, 5 attachments, 6 attachments, 7 attachments, 8 attachments, 9 attachments, 10 attachments, 11 attachments, 12 attachments, 13 attachments, 14 attachments, 15 attachments, 16 attachments, 17 attachments, 18 attachments, 19 attachments, or 20 attachments, and so forth. The number of attachments in the plurality of attachments may be greater than a number of wearable sensors included in the plurality of wearable sensors. The number of attachments 200 in the plurality of attachments 200 can include the number of wearable sensors 101 in the plurality of wearable sensors 101 multiplied by a number of days during which the plurality of wearable sensors are configured to record the brain activity of the user. For example, if there are four wearable sensors 101 configured to record the brain activity of the user for 7 days, the kit or system would include at least 28 attachments 200. For example, if there are four wearable sensors 101 configured to record the brain activity of the user for 3 days, the kit or system would include at least 12 attachments 200. The kit or system can include additional attachments 200 beyond the number of wearable sensors 101 in the plurality of wearable sensors 101 multiplied by a number of days during which the plurality of wearable sensors 101 are configured to record the brain activity of the user.

Disclosed herein are methods for monitoring brain activity. The methods can include detaching at least one wearable sensor 101 of a plurality of wearable sensors 101 configured to record a brain activity of a user. In some cases, each wearable sensor 101 includes a housing 102 having an extended, rounded shape. Each wearable sensor 101 can include at least two electrodes 104, 105 positioned on an exterior surface of the housing 102 and configured to detect EEG signals indicative of the brain activity of the user.

The methods can further include replacing a first attachment 200 of a plurality of attachments 200 with a second attachment 200 of the plurality of attachments 200. The first and second attachments 200 can include a first side shaped to substantially match the extended, rounded shape of the housing 102. The first side can be configured to be attached to the exterior surface of the housing 102 of the at least one wearable sensor 101. The first and second attachments 200 can include a second side configured to removably position the at least one wearable sensor 101 on a scalp of the user. In some cases, the number of attachments 200 in the plurality of attachments 200 is greater than a number of wearable sensors 101 in the plurality of wearable sensors 101.

The method can further includes reattaching the at least one wearable sensor 101 to the scalp of the user by adhering the second side of the second attachment 200 to the scalp of the user. The method may further includes resuming recording of EEG signals indicative of the brain activity of the user.

EEG System Setup and Provisioning

The systems and methods provided herein can include software to assist a user in setting up the system. The user may be a healthcare provider or a patient.

FIG. 6 is an illustration of an EEG monitoring system 600. The system of FIG. 6 includes a plurality of wearable sensors 601 configured to record a brain activity of a patient. Each wearable sensor 601 can include at least two electrodes configured to detect signals indicative of the brain activity of the user when the wearable sensor is positioned on a scalp of the user. Each wearable sensor 601 can further includes an electronic circuitry configured to, based on the signals detected by the at least two electrodes, determine data associated with the brain activity of the user and wirelessly transmit the data associated with the brain activity of the user to one or more portable computing devices 602.

In some cases, the system further includes a non-transitory computer readable medium storing instructions that, when executed by at least one processor the one or more portable computing devices 602, cause the at least one processor to facilitate activation of the plurality of wearable sensors 601; instruct the user to position the plurality of wearable sensors 601 on the scalp of the user using a plurality of attachments configured to removable attach the plurality of wearable sensors 601 to the scalp of the user; and record the data associated with the brain activity of the user transmitted by the plurality of wearable sensors 601.

The portable computing device 602 can include communication functionality, such as wireless communication functionality. The portable computing device 602 can be configured for being worn by the user. The portable computing device 602 can include a smartwatch, which may have a display. The portable computing device can 602 can include a smart band, smart jewelry, or the like, which may not have a display. The portable computing device 602 can include a tablet or another computing device, such as medical grade tablet. Such portable computing device 602 may include a display that is larger than the display of a smartwatch. The portable computing device 602 may connect to a remote server or cloud server through connection with a phone application, or may connect to a remote server or cloud server directly (for example, the portable computing device 602 may include a cellular communication chip that enables wireless communication with a remote server or cloud server).

Provided herein are systems for monitoring brain activity. In some implementations, the systems include a plurality of wearable sensors 601 configured to detect EEG signals indicative of a brain activity of a patient. Each wearable sensor of the plurality of wearable sensors 601 can include at least two electrodes configured to monitor the EEG signals when the wearable sensor is positioned on a scalp of the patient. Each wearable sensor of the plurality of wearable sensors 601 can include an electronic circuitry configured to process the EEG signals monitored by the at least two electrodes. In some cases, systems described herein further include a non-transitory computer readable medium storing executable instructions which may be executed by at least one processor of a portable computing device 602.

FIGS. 7A-7L provide example processes and screens (or modals) for wearable sensor 601 set-up, activation, placement, and verification. These can be implemented by or executed on a portable computing device 602, such as at least one processor of the portable computing device. While some illustrations may depict a wearable sensor 601 with a certain shape or configuration, this is meant as an illustrative example and not by way of limitation. For example, the processes and screens described herein may be used to guide a user through set-up, activation, placement, and verification of wearable sensors 601 having a variety of configurations, such as wearable sensors 601 having an extended, rounded shape as described herein. In some cases, through each of the screens, the system displays the next screen in response to user input, for example a user may press a button (such as a button displayed on a touch screen or a physical button on a portable computing device 602) to go to the next screen showing the next instructions.

Figure 7A:
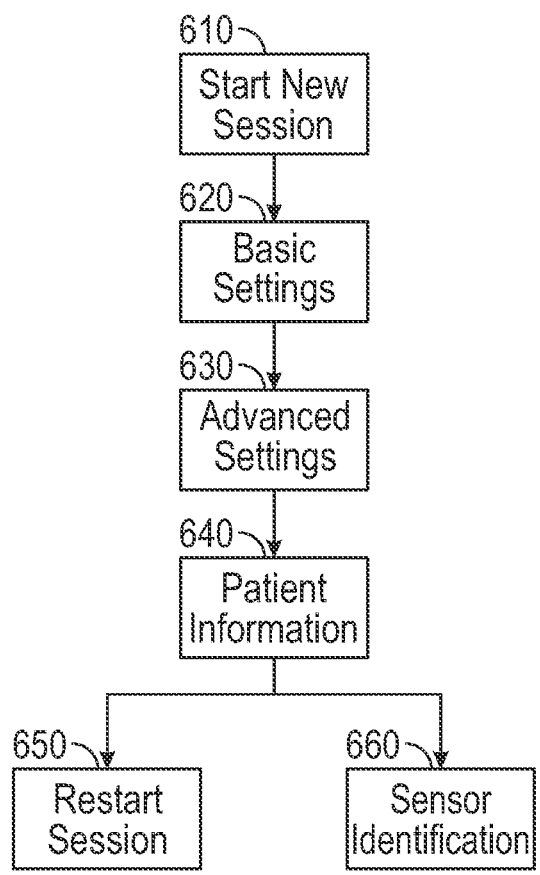
FIG. 7A illustrates a flow diagram of a process for set-up of a session.

FIG. 7A illustrates a flow diagram of a process for set-up of an EEG recording session. The process may include guiding a user through steps which may include starting a new session 610, inputting basic settings 620, inputting advanced settings 630, and inputting patient information 640. The set-up process can continue to sensor identification 660 or can be restarted 650. During set-up, a series of screens may be displayed on the portable computing device 602. In some cases, a start new session screen 610 is displayed. A user may interact with a screen, such as pressing a start button or pressing a settings button, to start set-up of a new session or to open a settings menu. The system can verify whether IT contact information has already been entered, and if it has already been entered, the system bypasses the start new session screen 610 and automatically transitions to basic settings screen 620. When basic settings screen 620 is displayed, a user may enter basic settings such as hospital IT contact information. In some implementations, the system stores the user input. When basic settings screen 620 is displayed, the system may verify that communication (such as, Bluetooth) is enabled on the portable computing device 602 the user is using to perform session set-up. If communication is not enabled, the system may request the operating system of the portable computing device 602 to enable communication or may prompt the user with a native modal informing the user that the app has requested communication be turned on. In response to user input, the system can then displays a start new session screen 610. User input to proceed to a start new session screen 610 may be allowed only if IT contact information has been entered. When a user enters a password, advanced settings screen 630 can be displayed.

When advanced settings screen 630 is displayed, the system may receive and store user input related to advanced settings. Advanced settings may include server URL and server path. Advanced settings may also include toggling on/off a kiosk mode, allowing patient barcode scan, and allowing device barcode scan. Advanced settings may also include a manual entry for a patient barcode and/or a device barcode. In some cases, in response to user input, the system then displays a start new session screen 610. User input to proceed to a start screen may be allowed only if IT contact information has been entered. When patient information screen 640 is displayed, the system may receive and store user inputs related to patient information. A patient barcode may be scanned with a camera of the portable computing device 602 or a patient barcode may be entered manually. Patient information may also include a patient's first and last name. In response to user input, the system can then displays a sensor identification screen 660. User input to proceed to a sensor identification screen 660 may be allowed only if patient information has been entered.

In response to user input, the process can then displays a restart session modal 650. The screen may ask a user to confirm whether the user wants to restart the session set-up. In response to a user input confirming restart, the system can clear all patient and sensor data already saved in a memory and the process may be restarted in 610. In response to user input canceling restart, the restart session modal 650 can be dismissed. In step 660, a user has completed the session set-up process and begins sensor identification, as further described in FIG. 7B.

Figure 7B:
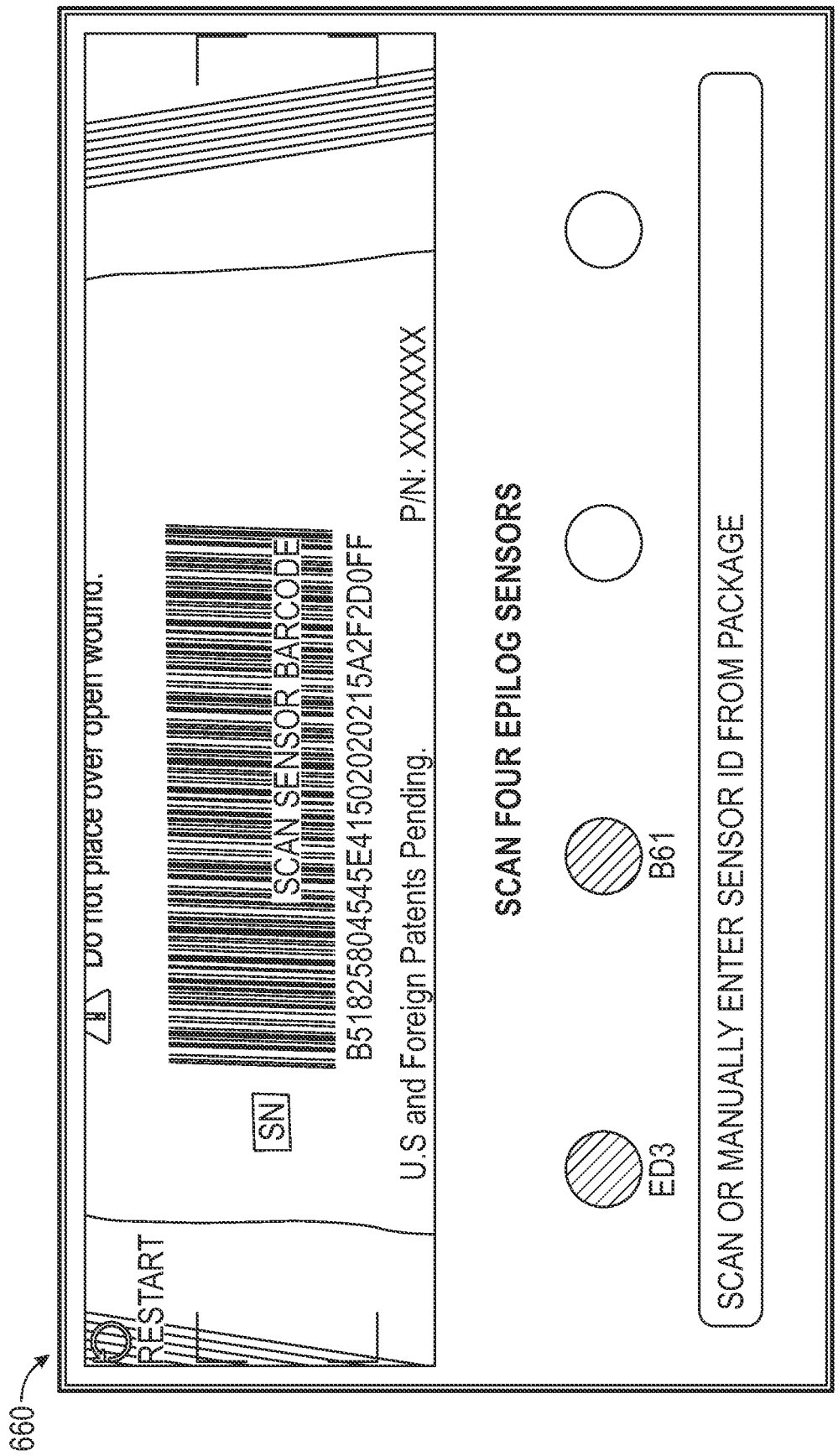

The executable instructions can cause at the least one processor to, prior to providing instructions to position the wearable sensor in the location on the scalp of the user, provide instructions to scan or enter the identification information for the wearable sensor 601. FIG. 7B illustrates an example sensor identification screen 660. The sensor identification screen 660 may include a display of a scan captured with a camera to enable a user to capture a barcode via camera of a portable computing device 602. The system may automatically look for barcode designs in the image captured by the camera. The system may store information related to sensor identification. The sensor identification screen 660 may include a display indicating whether a sensor ID corresponding to each wearable sensor 601 of the plurality of wearable sensors 601 has been entered. In the example of sensor identification screen 660, a circle corresponding to each wearable sensor of the plurality of wearable sensors 601 is filled in once sensor identification information for that wearable sensor 601 has been entered. In response to a user input (for example, selecting an already-entered sensor), the system may overwrite sensor identification information relating to an already-entered wearable sensor 601 with new sensor identification information. The system may receive and store sensor identification information manually entered by a user. In response to user input, the system can then displays a restart session modal 650. The system can automatically display the next screen once sensor identification information for each wearable sensor 601 of the plurality of wearable sensors 601 has been entered/scanned.

Figure 7C:
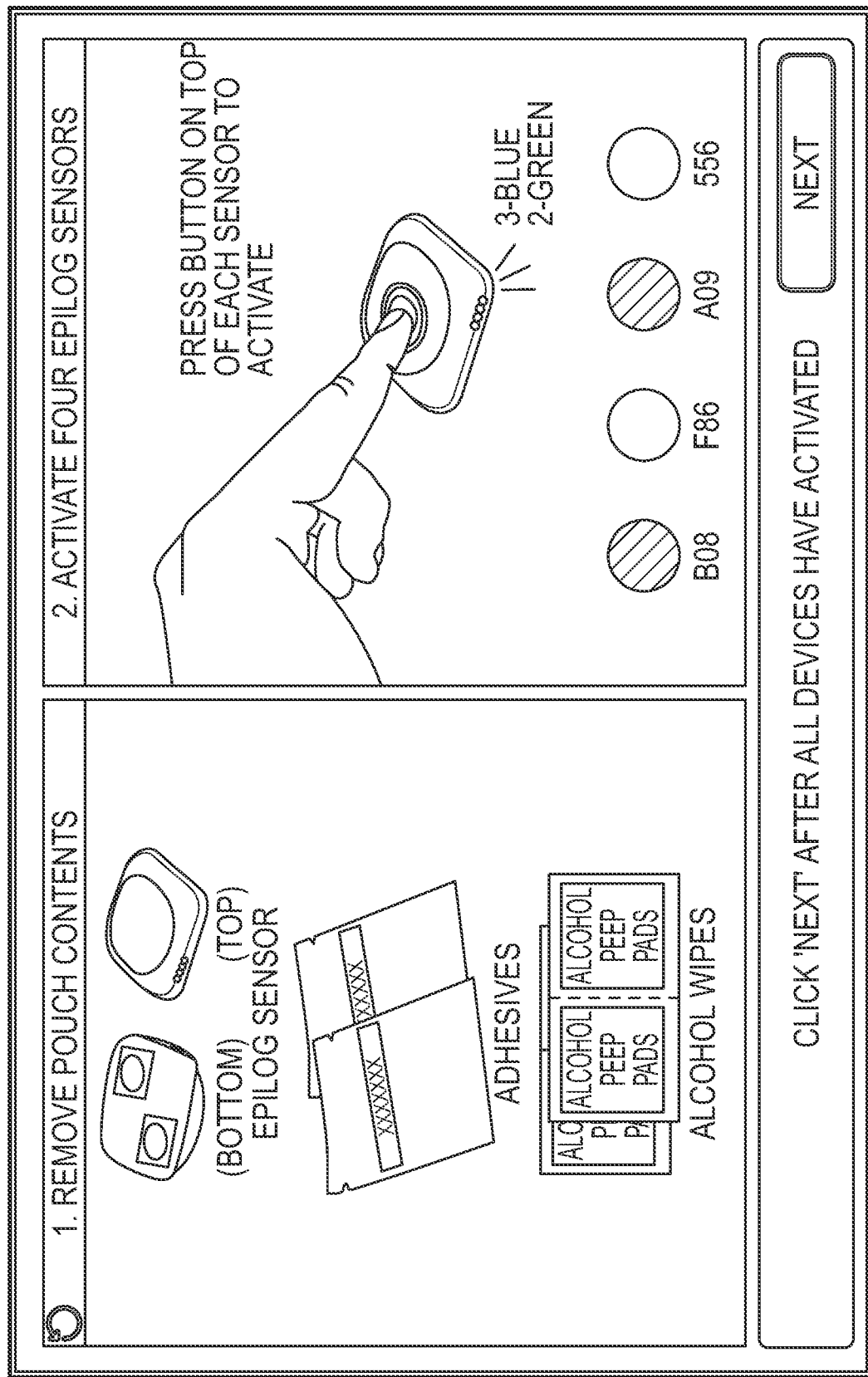

FIG. 7C illustrates an example sensor initialization screen. The screen may guide a user to remove the contents of a pouch in preparation for placement of one or more wearable sensors 601, such as one or more wearable sensors 601, one or more adhesives, and one or more alcohol wipes. The screen may also guide a user to activate one or more wearable sensors 601. A user may activate a wearable sensor 601 by pressing a button on top of the wearable sensor 601. The screen may include a display indicating whether each wearable sensor 601 of the plurality of wearable sensors 601 has been activated. In the example of FIG. 7C, a circle corresponding to each wearable sensor 601 of the plurality of wearable sensors 601 is filled in once that wearable sensor 601 has been activated. In response to a user input (for example, selecting an already-activated wearable sensor 601), the system may overwrite sensor activation information relating to an already-activated wearable sensor 601 with new sensor activation information. In some cases, the system starts a wireless scan (such as via Bluetooth) for the wearable sensors 601. The wireless scan may continue until recording is started or sensor set-up session is ended. When a wearable sensor 601 detected by a wireless scan, a local state can be updated with sensor information if the detected wearable sensor 601 is among the wearable sensors 601 previously identified (such as in the process described in connection with FIG. 7B). The system can wirelessly connect (such as via Bluetooth) with each activated wearable sensor 601, verifies connection capability, and verifies the wearable sensor 601 is working. After each of the plurality of wearable sensors 601 connect to the system, the system can wirelessly command the plurality of wearable sensors 601 to enter a synchronization state and then synchronization information (such as a sync-time-set advertisement) is wirelessly sent to the plurality of wearable sensors 601, as further described in connection with FIG. 10A or 10B. Wireless connection can then be re-established with each wearable sensor 601 of the plurality of sensors 601. The system can command each wearable sensor 601 of the plurality of sensors 601 to enter a sleep state. In the sleep state, a sensor 601 may not monitor EEG signals or transmit data. Once each wearable sensor 601 of the plurality of sensors 601 is activated, a user may enter an input to advance to the next step of the set-up such as FIG. 7E. In response to user input, the system can then display a restart session modal 650. If a set amount of time (such as one minute, two minutes, etc.) passes from beginning of the sensor activation process or from a sensor connection without a new wearable sensor 601 connecting, the system may display a connection time-out modal, such as the connection time-out modal of FIG. 7D.

Figure 7D:
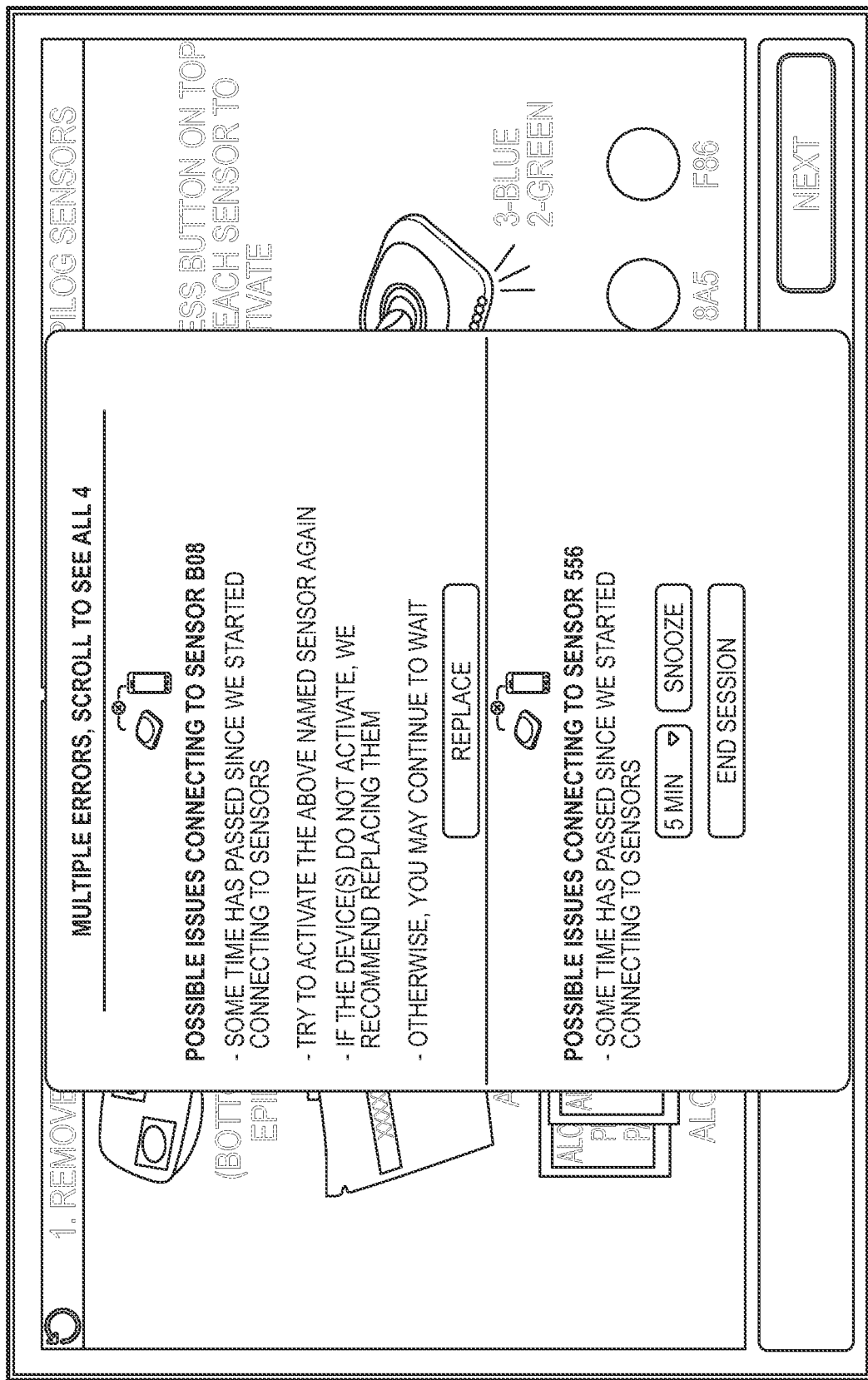

FIG. 7D is an example connection time-out modal. The connection time-out modal may display errors and troubleshooting information related to sensor activation. The system may allow a user to snooze (dismiss for a set amount of time) the connection time-out modal, replace one or more wearable sensors 601, or end the session. If a user selects to end the session, the system may display an end session modal. If a user selects to replace one or more wearable sensors 601, a replace sensor modal may be displayed. If a user selects to snooze, the connection time-out modal may disappear. In some cases, the snooze interval (amount of time) is saved to a memory store. The user may input the snooze interval. The system can display the connection time-out modal again after the snooze interval has elapsed. If a wearable sensor 601 is activated and connects, the system may automatically dismiss the connection time-out modal.

Figure 7E:
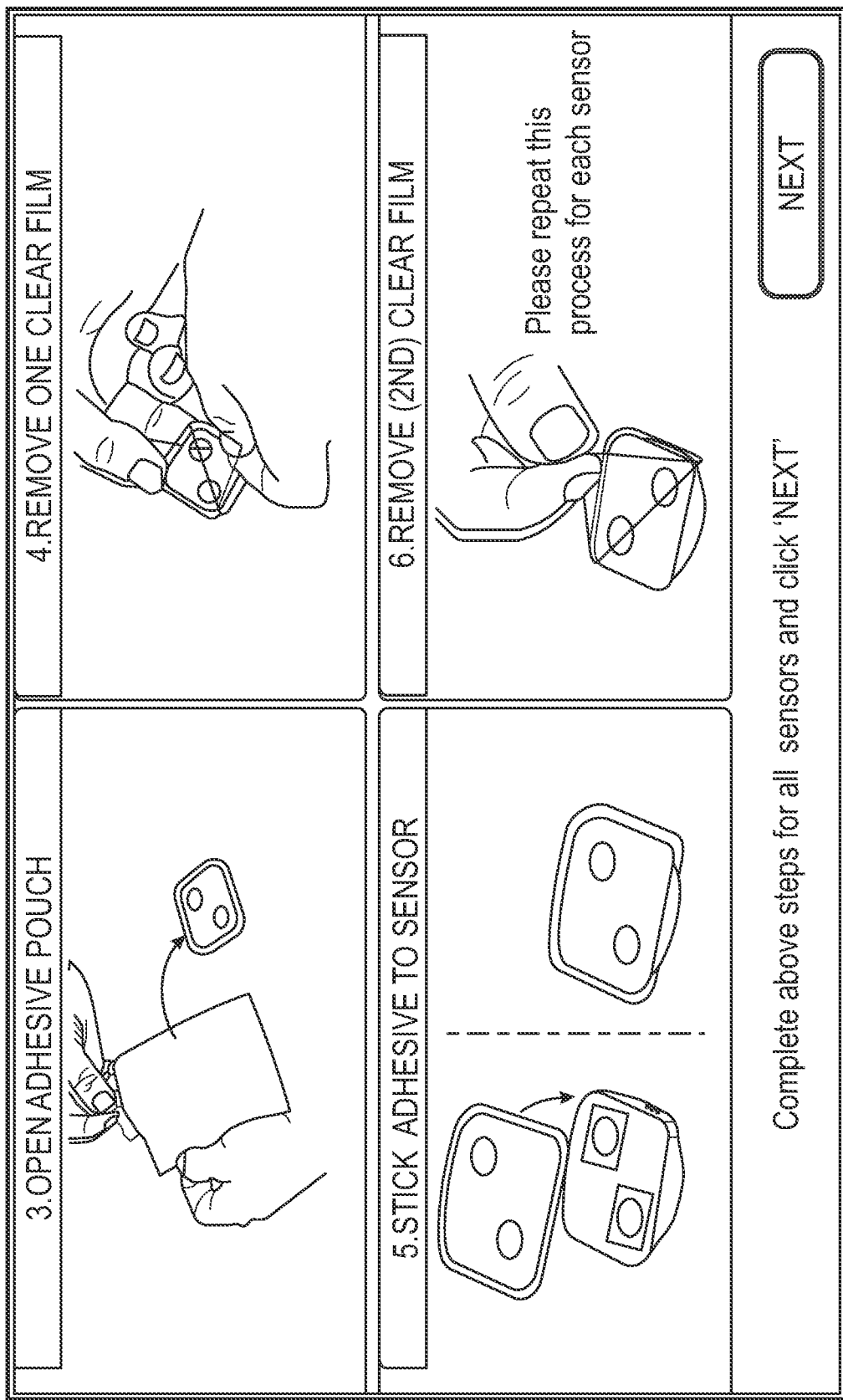

FIG. 7E is an example sticker (or attachment) placement screen. Providing instructions to position the wearable sensor 601 in the location on the scalp of the user can include instructing a use of a plurality of attachments configured to removably attach the wearable sensor 601 to the scalp of the user. For example, a sticker placement screen may guide a user to open an adhesive pouch and remove an adhesive. The sticker placement screen can guide a user to remove a film (also referred to as a liner or backing) from the adhesive. A sticker placement screen may instruct a user to apply the adhesive to the wearable sensor 601 (such as with the correct alignment over the electrodes). A sticker placement screen may guide a user to remove a second film from the adhesive in preparation for sticker placement. In response to user input, the system can then display a restart session modal 650. A user may enter an input to cause the system to advance to the next step of the set-up, such as FIG. 7F.

The executable instructions can cause the at least one processor to: provide instructions to position a wearable sensor 601 of the plurality of wearable sensors 601 in a location of a plurality of locations on the scalp of the user and activate the wearable sensor 601; verify an identification of the wearable sensor 601; responsive to verification of the identification of the wearable sensor 601, verify an impedance of the wearable sensor 601; and responsive to verification of the impedance of the wearable sensor 601, provide instructions to position and activate another wearable sensor 601 of the plurality of wearable sensors 601 and perform verification of an identification and an impedance of the another wearable sensor 601.

Figure 7F:
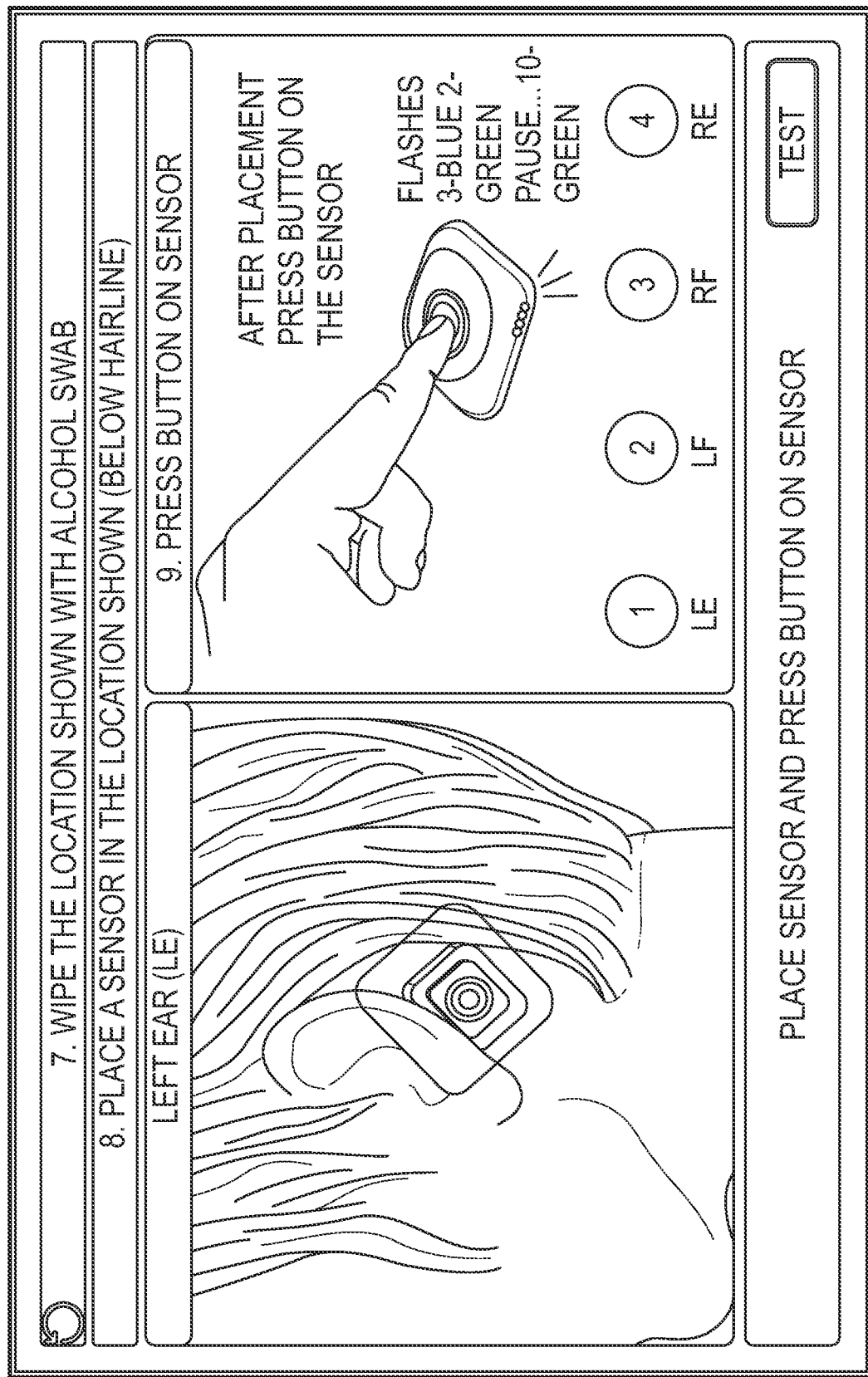

FIG. 7F depicts an example sensor placement and activation screen. Sensor may be placed in four locations on the scalp, such as behind left ear (LE), behind right ear (LE), left front side of the forehead (LF), and right front side of the forehead (RF). A sensor placement and activation screen may guide a user to wipe the location on the user's body with an alcohol swab provided in a kit. For example, the location may be behind an ear or on another location on the scalp. The screen may display a graphic to show the user which location on the user's body to clean with the swab. A sensor placement and activation screen may guide a user to place a wearable sensor 601 on the patient's body in a location (for instance, the scalp). In some cases, providing instructions to position the wearable sensor 601 includes displaying instructions on a screen of the portable computing device 602. For example, the screen may display a graphic to show the user where to place the wearable sensor 601.

In some implementations, providing instructions to position the wearable sensor 601 comprises displaying the location on the screen of the portable computing device 602 and instructions to activate the wearable sensor 601. For example, a sensor placement and activation screen may instruct a user to press a button on the wearable sensor 601 after placement in the directed location to activate the wearable sensor 601. In some cases, wireless connection (such as via Bluetooth) is made with previously connected wearable sensors 601. The system can verify the identity of an activated wearable sensor 601 to confirm that the activated wearable sensor 601 is a wearable sensor 601 that was identified by the user, for example scanned in the process described in connection with FIG. 7B or activated in the process described in connection with FIG. 7C. The screen may include a display indicating whether each wearable sensor 601 of the plurality of wearable sensors 601 has been activated. In the example of FIG. 7F, a circle corresponding to each wearable sensor of the plurality of wearable sensors 601 is filled in once that wearable sensor 601 has been activated. The screen may include a display indicating whether each wearable sensor 601 of the plurality of wearable sensors 601 remains wirelessly connected to the portable computing device 602, and may display a notification, graphic, and/or alert if an activated wearable sensor 601 becomes disconnected. In response to a user input, the system can display a restarts placements modal, such as the restart placement modal of FIG. 7H.

Once a wearable sensor 601 of the plurality of wearable sensors 601 is activated, the system may prompt as user to initiate an impedance test of the wearable sensor(s) 601. In the example of FIG. 7F, a user may press a test button once the wearable sensor 601 is placed and activated. In some cases, when a user initiates the impedance test, a command is wirelessly sent (such as via Bluetooth) to a wearable sensor 601 to run an impedance check. In some implementations, the systems checks whether an impedance measurement from a wearable sensor 601 satisfies a pre-determined threshold, such as 100 kOhm or more or 500 kOhm or more.

In some implementations, if the impedance measurement does not satisfy a pre-determined threshold, the system may provide an indication to the user, such as display an appropriate screen informing of poor electrode contact. In some implementations, the executable instructions further cause the at least one processor to, responsive to not verifying the impedance of the wearable sensor 601, repeat one or more of: providing instructions, verifying the identification, and verifying the impedance for the wearable sensor 601. In some cases, repeating includes providing instructions to reposition the wearable sensor 601 and verifying the impedance of the sensor. In some cases, responsive to not verifying the impedance of the wearable sensor 601 for a second time, the executable instructions cause the processor to restart providing instructions, verify the identification, and verify the impedance for the plurality of wearable sensors 601. In some implementations, when restarted, the system wipes all saved sensor placements data at all locations and begins providing instructions, verifying the identification, and verifying the impedance for the plurality of wearable sensors 601 from the first of the plurality of wearable sensors 601. If the impedance is verified (for example, the impedance measurement satisfies the pre-determined threshold), the system can return to the placement screen with instructions to place, activate, and test the next wearable sensor 601 in the sequence of the plurality of sensors 601.

The executable instructions can further cause the at least one processor to provide an alert in response to detecting that at least two wearable sensors 601 of the plurality of wearable sensors 601 have been positioned in the same location on the scalp of the user or other position or activation in error. This can include responsive to detecting that at least two wearable sensors 601 of the plurality of wearable sensors 601 have been positioned in a particular (i.e., incorrect or unidentified) location of the plurality of locations on the scalp of the user, restart providing instructions, verifying the identification, and verifying the impedance for the plurality of wearable sensors 601. Detecting that the at least two wearable sensors 601 have been positioned in the same location can include detecting that multiple wearable sensors 601 have been activated substantially simultaneously. This can be performed as follows. The executable instructions can cause the at least one processor to sequentially provide instructions to position and activate, verify an identification, and verify an impedance of each wearable sensor 601 of the plurality of wearable sensors. One wearable sensor 601 of the plurality of wearable sensors 601 can be placed, activated, and tested for impedance for one location, one at a time (in other words, in a sequence). For example, the user is instructed to place a first wearable sensor 601 in a first location, activate the first wearable sensor 601, and initiate an impedance test for the first wearable sensor 601; then the user is instructed to place a second wearable sensor 601 in a second location, activate the second wearable sensor 601, and initiate an impedance test for the second wearable sensor 601; and so on. When a user initiates an impedance test, if multiple wearable sensors 601 have been activated before the impedance test, the system can display a multiple sensors activated alert modal, such as the multiple sensors activated alert modal of FIG. 7G. As another example, if multiple wearable sensors 601 have been activated (for instance, in FIG. 7F) before an impedance test is initiated, the system can display the activated alert modal. In some cases, determining whether multiple wearable sensors 601 have been activated substantially simultaneously can be performed based on determining whether at least two sensors have been activated within a threshold time duration (such as, 10 seconds or less, 30 seconds or less or more, or the like).

Figure 7G:
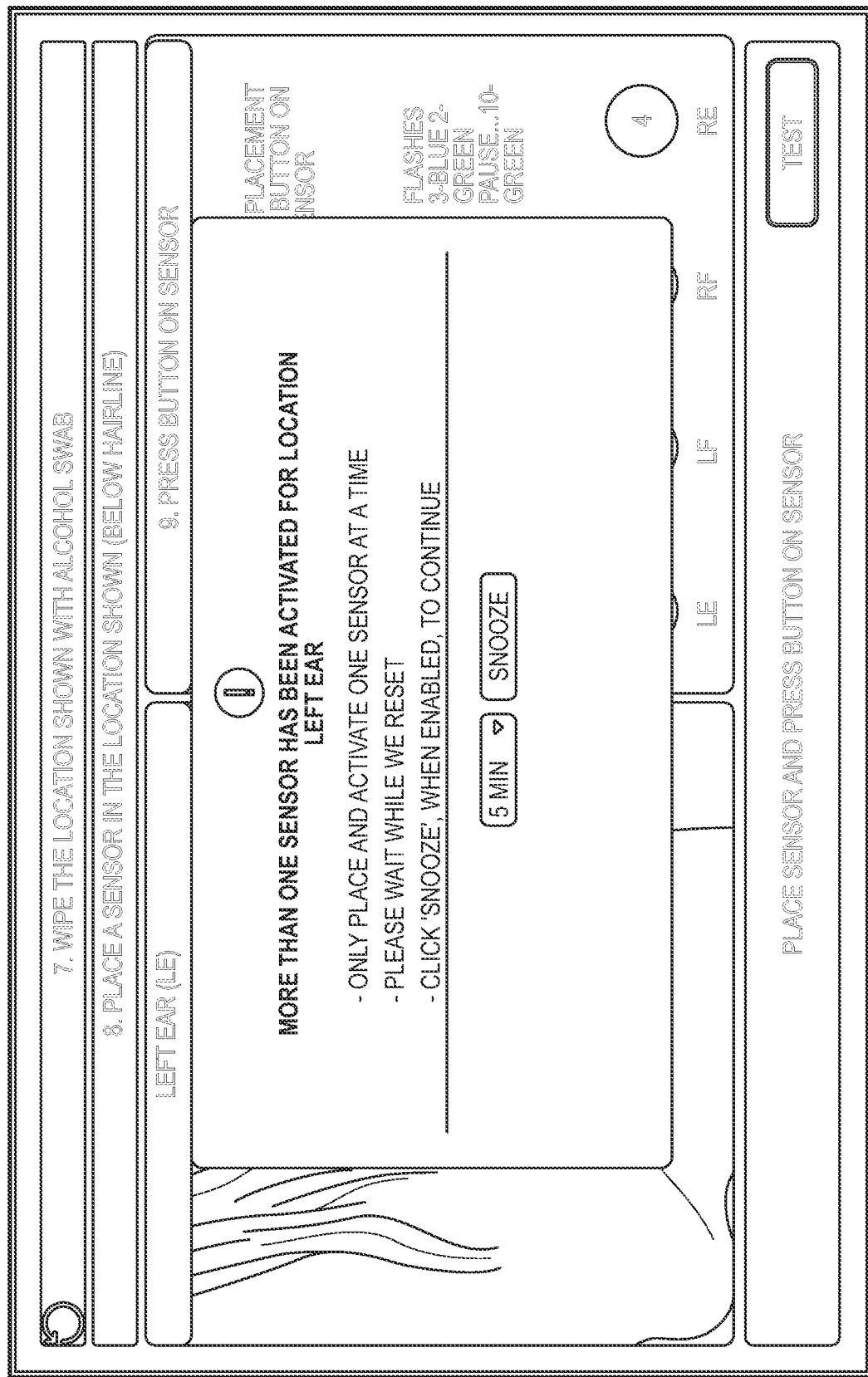

FIG. 7G is an example multiple sensors activated alert modal. In some implementations, the multiple sensors activated alert modal notifies a user that more than one wearable sensor 601 has been activated for a location and instructs the user to only place and activate one wearable sensor 601 at a time. The multiple sensors activated alert modal can instruct a user to wait. When a multiple sensors activated alert modal is displayed, the system can connect to the wearable sensors 601, and commands all connected wearable sensors to enter a sleep state. A user may select to dismiss or snooze the multiple sensors activated alert modal. When a user selects to dismiss or snooze the multiple sensors activated alert modal, the system can command wearable sensors 601 that are connected and that have not been correctly placed to enter an inactive state. When a user selects to dismiss or snooze the multiple sensors activated alert modal, the system once again may display a sensor placement and activation screen.

Figure 7H:
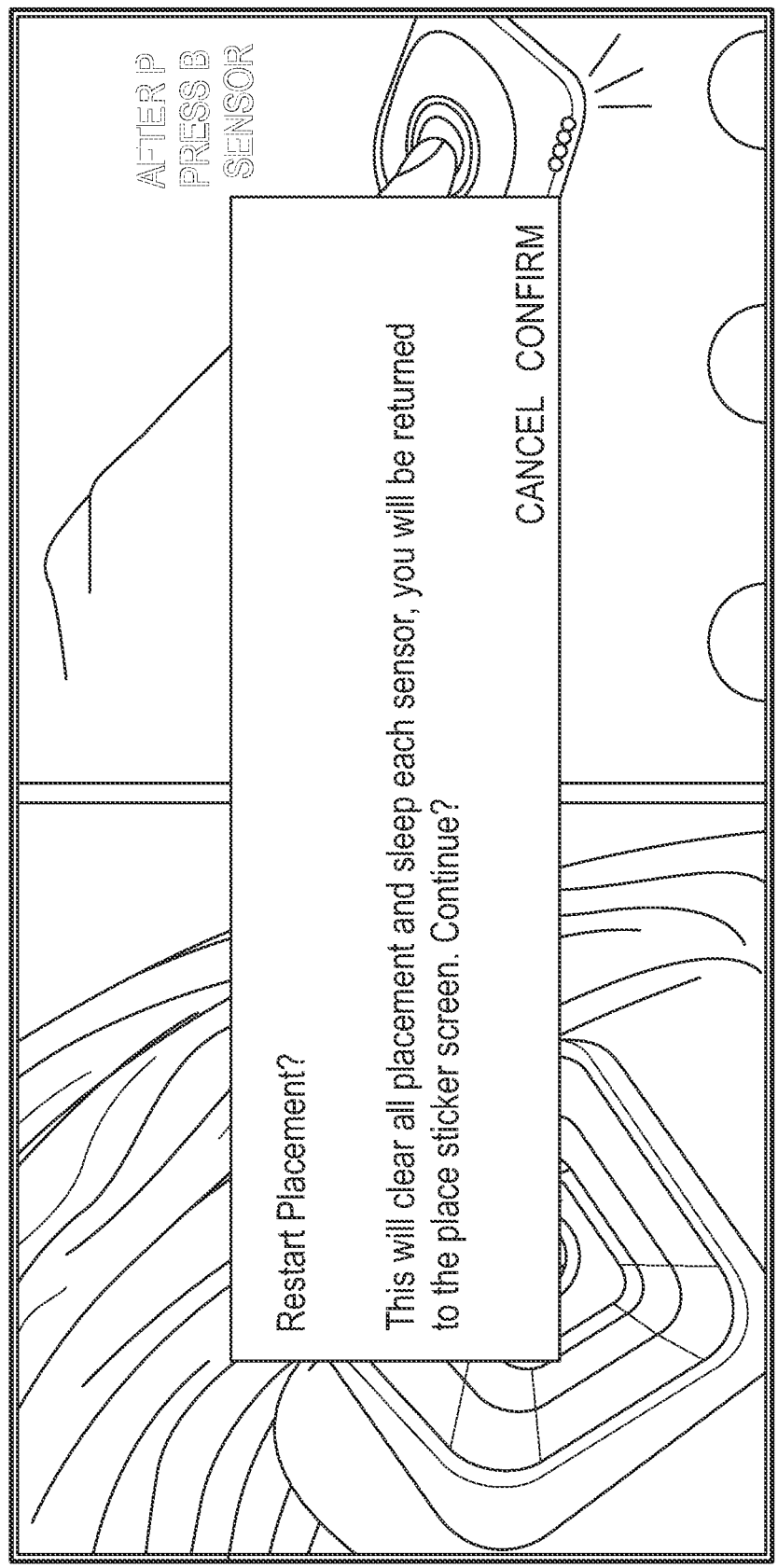

FIG. 7H shows an example restart placement modal. In some cases, the restart placement modal prompts a user to confirm or cancel whether to restart the placement process. When placement is restarted, the system can wipe all saved sensor placements data at all locations. When placement is restarted, the system can command the sensors to enter a sleep state. When placement is restarted, the system can display the sticker placement screen, such as the sticker placement screen of FIG. 7E. When restart is canceled, the restart placement modal can be dismissed.

Figure 7I:
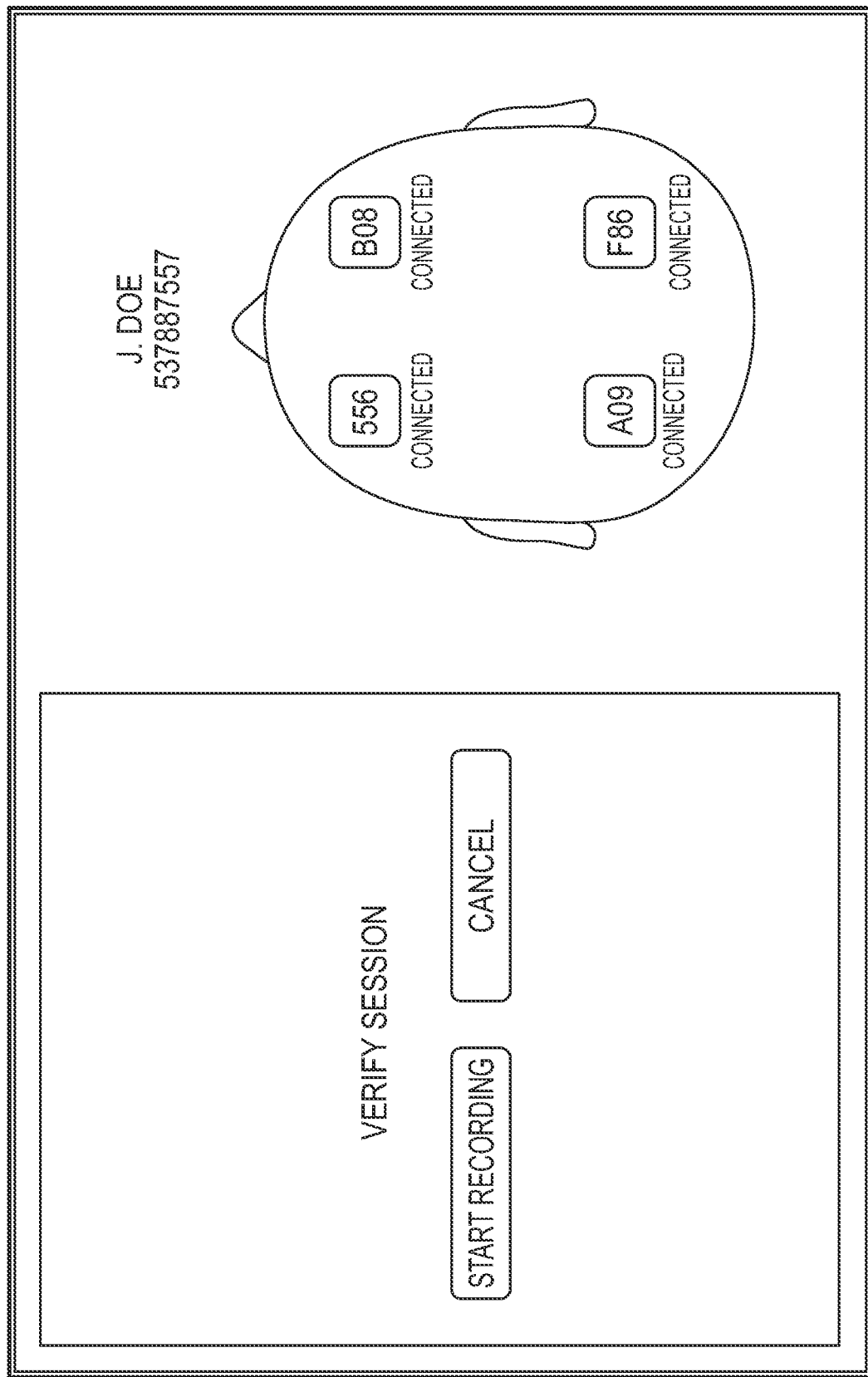

FIG. 7I shows an example verify session screen. This screen may be displayed after all the sensors have been placed and activated. The system can display a screen so that a user can verify each sensor identification matches the sensor identification recorded in the system for each location (for instance, recorded in FIG. 7B). In the example of FIG. 7I, the portable computing device 602 displays a diagram of the head with squares representing sensor placements (such as sensor ID) and sensor state (such as connected). The portable computing device 602 can display a notification if there is an issue, such as an activation, identification, or impedance issue, with one or more of the wearable sensor 601 placements. For example, the graphical representation of a sensor with an issue may flash red/blue, such as an alert modal appeared and was snoozed. In response to user input such as clicking on a representation of a wearable sensor 601 on the screen, the system can display a sensor modal with sensor information. In response to user input (such as selecting to cancel), the system can display an end session modal. In response to user input, the system can initiate the recording session.

Figure 7K:
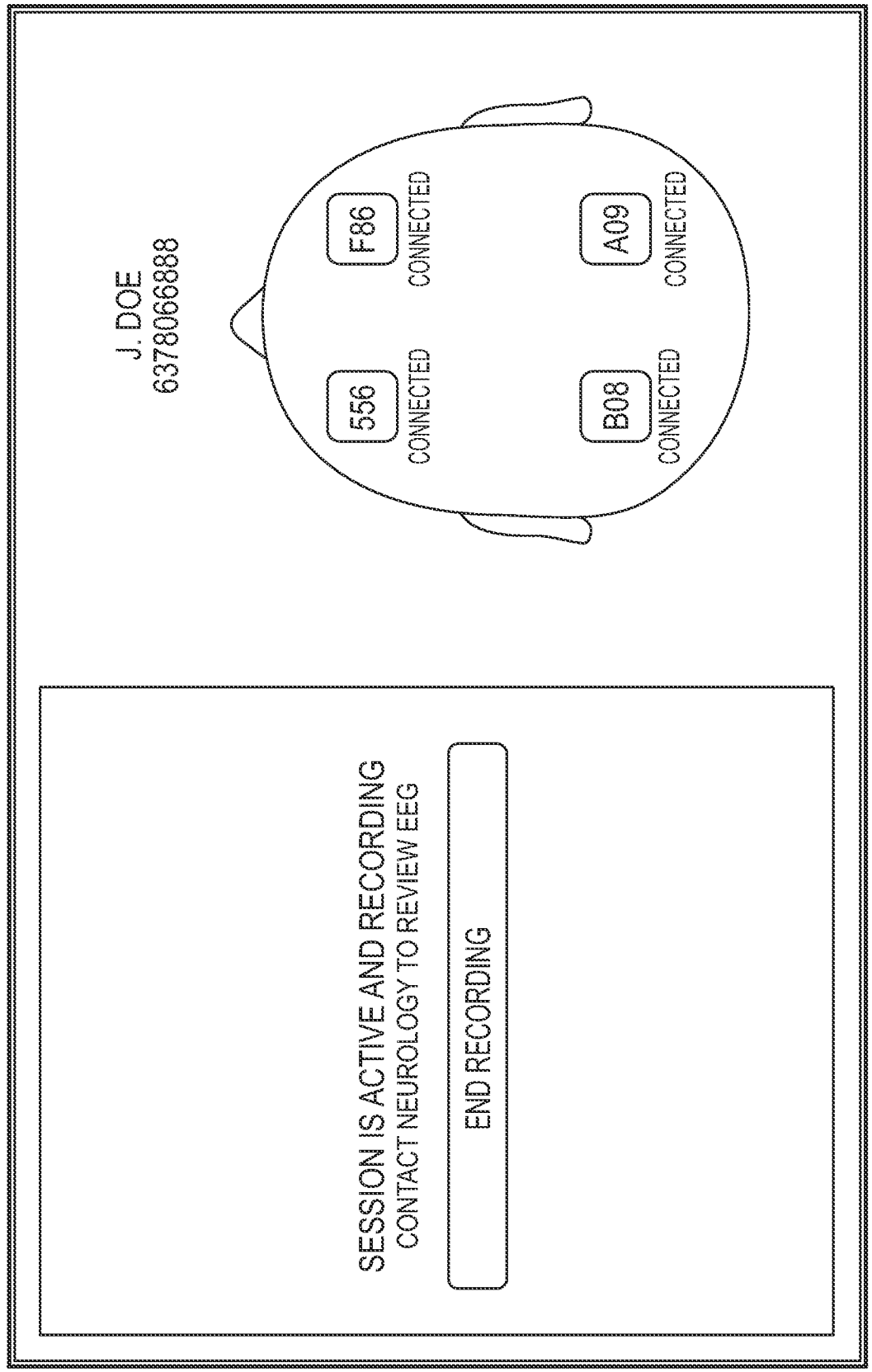

After verification has been completed, EEG recording session may be started. As part of verification of subsequent to the verification, wearable sensors 601 may be synchronized, as further described in connection with FIG. 10A or 10B. FIG. 7J illustrates an example screen that informs the user that synchronization is being performed. The executable instructions can further cause the at least one processor to, responsive to verification of the identity and impedance of each wearable sensor 601 of the plurality of wearable sensors 601, record the processed EEG signals wirelessly transmitted by the plurality of wearable sensors 601. FIG. 7K is an example active recording screen. The system can store the recording started time in the memory. Wireless scans (such as Bluetooth scan) can be stopped. A wireless scan may start again if a wearable sensor 601 disconnects. Real-time data notifications can be enabled for all wearable sensors 601. The portable computing device 602 may display a notification if there is an issue, such as an activation, identification, or impedance issue, with one or more of the wearable sensor 601 placements. For example, the graphical representation of a wearable sensor 601 with an issue may flash red/blue, such as an alert modal appeared and was snoozed. In response to user input such as clicking on a representation of a wearable sensor 601 on the screen of a portable computing device 602, the system can display a sensor modal with sensor information.

The portable computing device 602 can send a message containing information for session events for recording started and recording ended to a remote server or cloud server over the Internet. A recording started or recording ended message can contains information such as patient information, wearable sensor(s) 601 information, recording start time, and/or recording end time. The portable computing device 602 can receive messages containing real-time data/events from the plurality of wearable sensors 601 and communicates messages containing real-time data/events to a remote server or cloud server over the Internet. The portable computing device 602 can display a notification on the active recording screen if there is an issue, such as an activation, identification, or impedance issue, with one or more of the wearable sensor 601 placements. In the example of FIG. 7K, the portable computing device 602 displays a diagram of the head with squares representing wearable sensor 601 placements (such as sensor ID) and sensor state (such as connected). A user may interact with the display to end the recording session. The portable computing device 602 can display diagnostic information as well as session ID and portable computing device 602 ID.

In response to user input (such as clicking "end recording"), the system can display an end recording modal. After a predefined amount of time has elapsed (for example 48 hours) after beginning of recording, the system can automatically end the recording session and displays a finalizing session screen (not shown).

Figure 7L:
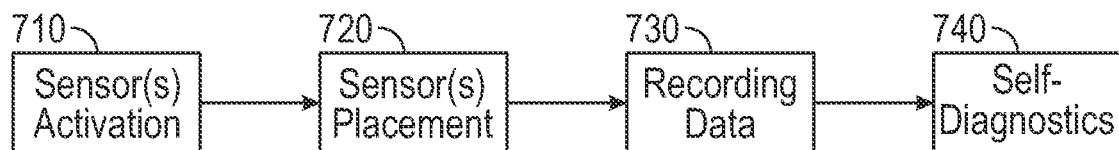
FIG. 7L is a flow diagram of a process for sensor set-up and provisioning.

FIG. 7L illustrates a flow diagram of a process for guiding a user through sensor set-up and provisioning. As described herein, the process may include guiding a user through the steps of sensor(s) activation 710, sensor(s) placement 720, recording data 730, and self-diagnostics 740.

In some cases, sensor(s) activation 710 includes using the application to guide a user to scan a barcode associated with a wearable sensor 601 with the camera feature of a portable computing device 602. Sensor(s) activation 710 can include using an application to guide a user to manually enter a barcode associated with a wearable sensor 601 using a portable computing device 602. The application can create a passcode for each sensor based on the scanned or entered barcode. The passcode may be unique and ensure that only 4 provisioned wearable sensors 601 set up in a session can communicate with the portable computing device 602. The application can guide a user to press and/or hold a button on each wearable sensor 601 to activate the wearable sensor 601.

The application can display information related to sensor activation on a display of a portable computing device 602. Information related to sensor activation may include whether each wearable sensor 601 has been activated. FIG. 7F illustrates an example screen associated with sensor(s) activation 710 and sensor placement 720 displayed on a portable computing device 602. In some cases, sensor(s) placement 720 includes using the application to guide a user to place wearable sensors 601 on the scalp of a patient. The application can walk the user through multiple images, one for each wearable sensor 601, and shows the user the location that the user should place each sensor.

Placement of multiple wearable sensors 601 can follow a pattern, such as left to right. A display may provide a graphical instruction such as that illustrated in FIG. 7F. An emergent care screening may be conducted on a patient using four wearable sensors 601, two on the forehead and two behind the ears. With this four-sensor arrangement, a desired montage may be created, for example via subtracting the EEG signal from one sensor relative to another to create a 10-channel longitudinal-transverse montage, as described in U.S. Pat. No. 11,020,035 and U.S. Patent Publication No. 2021/0307672, each of which is incorporated by reference in its entirety.

The instructions can further cause the processor to activate a wearable sensor 601 to run an impedance test to ensure the wearable sensor 601 is attached to the skin and has adequate electrode contact. The impedance test may include pushing a current and measuring a voltage.

Recording data 730 can include recording EEG data. Recording data 730 may be initiated in response to user input (such as pressing a button) on an application running on a portable computing device 602. The application on the portable computing device 602 can display a screen indicating that recording is in session, such as recording screen of FIG. 7K.

In some cases, recording data 730 includes determining the state of the wearable sensor 601. States may include a waiting state (on but not recording), a recording state, a charging state, a communicating state, etc. State information may include whether and when the internal clock of the sensor has been set, a number of recordings/pages of recordings, battery charging status (fully charged, partially charged, etc.).

In some implementations, the instructions further cause the at least one processor to cause a display of a portable computing device 602 to display push notifications. The push notifications may be based on state information. The push notifications may be based on change in state.

The instructions can further cause the at least one processor to run self-diagnostics 740 on the system, including on the plurality of wearable sensors 601. Self-diagnostics 740 can include identifying a problem associated with one or more wearable sensors 601, sensor data, and/or communication to or from the wearable sensors 601. Self-diagnostics 740 can include diagnosing a problem. In some cases, the problem includes system issues. System issues may include a battery issue, a wearable sensor 601 being disconnected, connection time-out, poor electrode contact, cellular signal error, Bluetooth error, portable computing device 602 Wi-Fi failure, remote server or cloud server issues, or that the recording had not started. The problem may include sensor/data issues. Sensor/data issues may include in-phase cancellation of electrographic activity (due to close spacing of electrodes), muscle artifacts, or saturation.

Provided herein are methods for monitoring brain activity of a patient. The methods include, by at least one processor of a portable computing device 602, providing instructions to position a plurality of wearable sensors 601 in a plurality of locations on the scalp of the user. The plurality of wearable sensors 601 can be configured to detect EEG signals indicative of a brain activity of the patient, each wearable sensor 601 including at least two electrodes configured to monitor the EEG signals when the wearable sensor 601 is positioned on the scalp of the user and an electronic circuitry configured to process the EEG signals monitored by the at least two electrodes. The method can further include providing an alert in response to detecting that at least two wearable sensors 601 have been positioned in a particular location of the plurality of locations on the scalp of the user. The method can further includes, in response to verifying that the plurality of wearable sensors 601 has been correctly positioned in the plurality of locations on the scalp of the user, recording the processed EEG signals wirelessly transmitted by the plurality of wearable sensors 601.

Advantageously, guiding a user using a portable computing device 602 can allow EEG setup and monitoring by non-experts, such as clinicians in a local or rural hospital unaccustomed to EEG monitoring.

Handing Off Control

It can be advantageous to hand off control of EEG sensors between portable computing devices. For example, EEG sensor setup can be performed on a first portable computing device (such as, a tablet) and subsequently transferred to a second computing device (such as, a watch, smart band, smart jewelry, or the like). The second portable computing device can be a wearable computing device without a screen or with a screen that is smaller than that of the first computing device. The first portable computing device can be configured to facilitate activating and positioning the EEG sensors on the scalp of the patient and the second portable computing device can be configured to facilitate monitoring of the brain activity of the patient and detecting one or more disorders. Transfer of control to the second device may advantageously allow EEG monitoring with a smaller and cheaper user-worn computing device.

The second portable computing device and one or more EEG sensors can communicate directly or through another computing device, such as a phone. The second portable computing device can communicate with a remote server or cloud server through another computing device or directly (such as, with a cellular communication chip).

The first portable computing device can have a prescriptive function to train, prescribe, provision or otherwise determine how the EEG system will be used during ambulatory wear. This could include parental controls, duration and location of wear, and other prescriptive functions. The second portable computing device can have an endemic function and its interaction with the patient differs depending on the prescription and provisioning by the first portable computing device.

Figure 8:
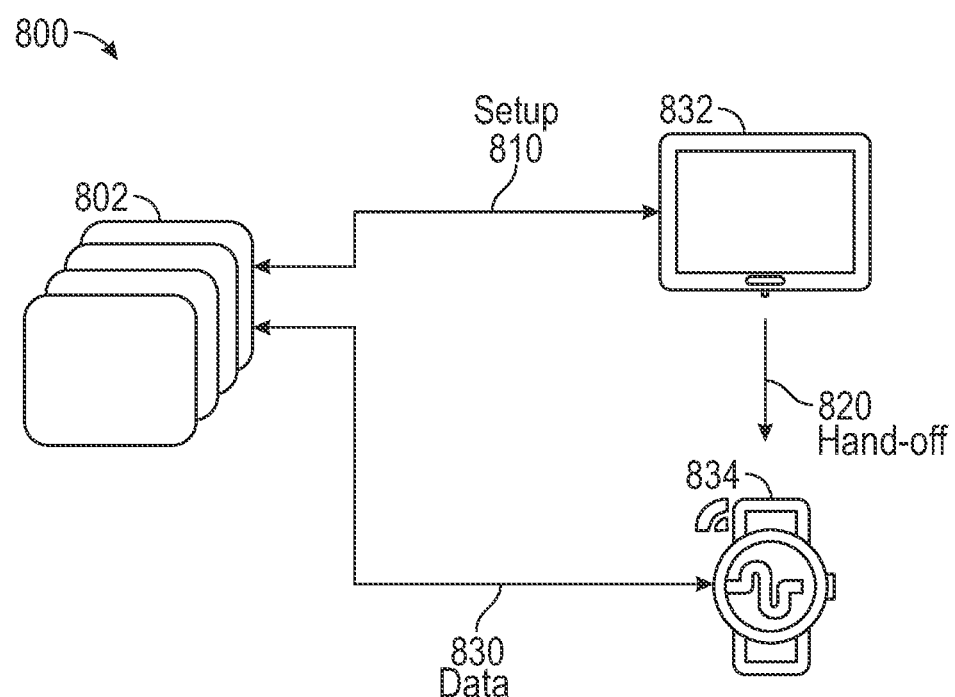
FIG. 8 is an illustration of a sensor control transfer environment.

FIG. 8 is an illustration of an EEG sensor control transfer environment 800. The sensor control transfer environment 800 includes a plurality of wearable sensors 802 (which can be similar to the sensors 101), a first portable computing device 832, and a second portable computing device 834, which can be configured to be worn by a patient. In the example of FIG. 8, the plurality of wearable sensors 802 and the first portable computing device 832 communicate to facilitate setup 810 of the plurality of wearable sensors 802. The first portable computing device 832 and the second portable computing device 834 communicate to facilitate hand-off 820 of control of the plurality of sensors 802 from the first portable computing device 832 to the second portable computing device 834. After hand-off 820, the second portable computing device 834 communicates with the plurality of wearable sensors 802 to receive and send data 830. Data 830 may include sensor data such as EEG measurements or sensor status, and also may include commands to the plurality of sensors 802 from the second portable computing device 834 such as to begin recording data.

Provided herein are methods for monitoring of brain activity. In some cases, the method includes activating (for example, setup 810) a plurality of wearable sensors 802 configured to detect EEG signals indicative of a brain activity of a patient and positioned in a plurality of locations on a scalp of the patient. Each wearable sensor 802 can have at least two electrodes configured to monitor the EEG signals when the wearable sensor 802 is positioned on the scalp of the patient, and an electronic circuitry configured to process the EEG signals monitored by the at least two electrodes and wirelessly transmit processed EEG signals to a first portable computing device 832. Activating can include following instructions displayed on a display of the first portable computing device 832 (for example, setup 810).

The method can further includes, subsequent to the activation of the plurality of wearable sensors 802, transferring control (for example, hand-off 820) of the plurality of wearable sensors 802 to a second portable computing device 834. The second portable computing device 834 can be configured to be worn by the patient to permit the second portable computing device 834 to wirelessly receive the processed EEG signals (for example, data 830). The second portable computing device may not include a display or may include a display that is smaller than the display of the first portable computing device 832.

The first portable computing device 832 can be configured to facilitate activating and positioning the plurality of wearable sensors 802 on the scalp of the patient (for example, setup 810) and the second portable computing device 834 is configured to facilitate monitoring of the brain activity of the patient (for example, receiving data 830) and detecting one or more disorders. Transferring control can cause the first portable computing device 832 to cease wirelessly receiving the processed EEG signals. The first portable computing device 832 can be a tablet and the second portable computing device 834 can be a smartwatch.

The method can further include, prior to transferring control to the second portable computing device 834, authenticating the second portable computing device 834. Authenticating the second portable computing device 834 can include scanning a QR code of the second portable computing device 834. For example, a first portable computing device 832 may instruct a user to scan a QR code displayed on a second portable computing device 834 using a camera of the first portable computing device 832. A first portable computing device 832 may instruct a user to manually enter a code associated with a second portable computing device 834 (such as a code displayed on a second portable computing device 834).

The method can further includes, responsive to an alert displayed on the display of the second portable computing device 834, causing the second portable computing device 834 to display instructions for resolving the alert and following the instructions to resolve the alert.

Figure 9A:
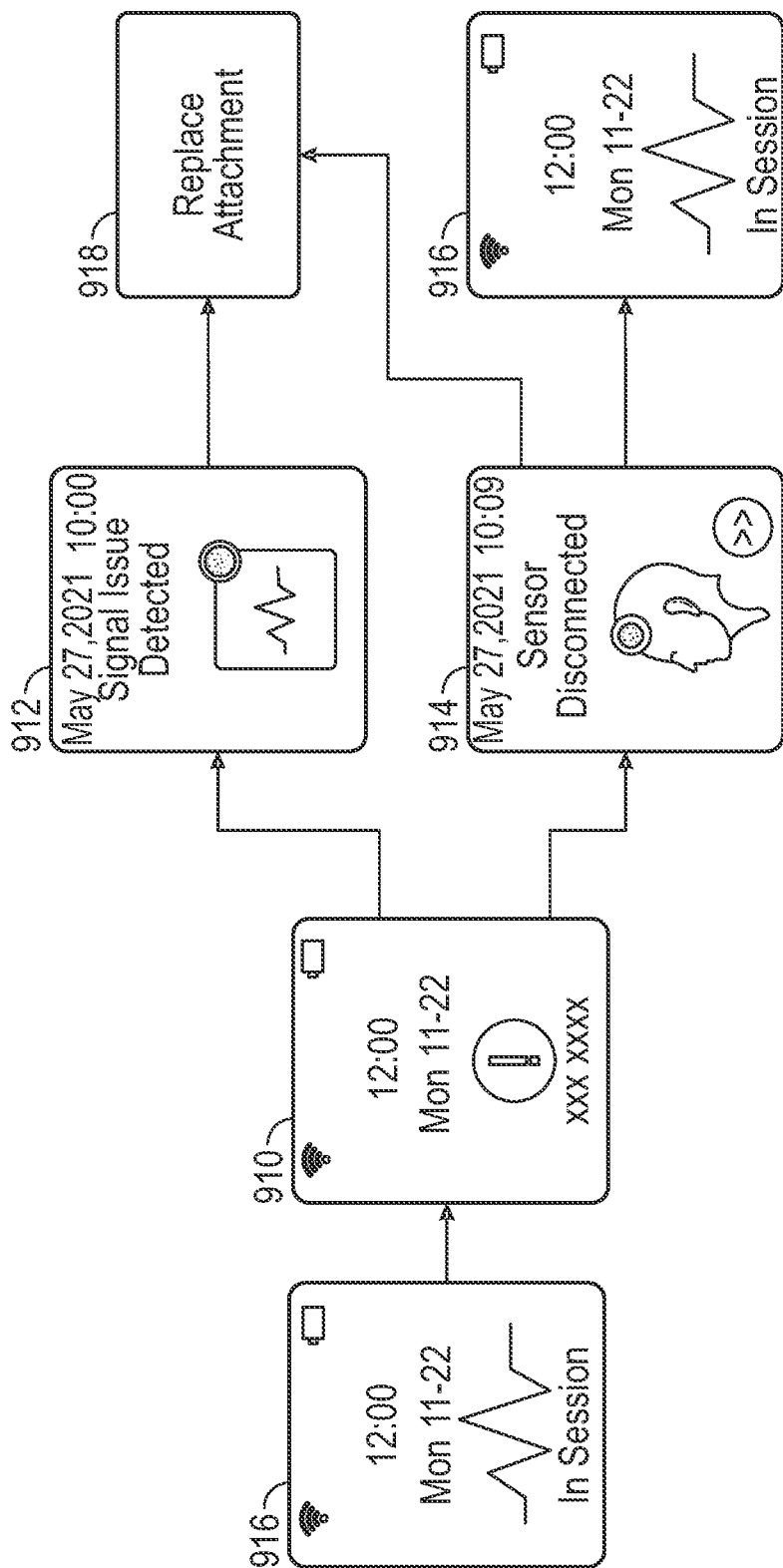
FIGS. 9A to 9E illustrates examples screens associated with data recording and sensor management displayed on a portable computing device.

FIG. 9A illustrates a process for data recording and sensor management, which can be executed by a second portable computing device 834. The process is illustrated as a sequence of screens that can be displayed on the second portable computing device 834 (or otherwise reproduced, for instance, auditorily reproduced by the second portable computing device). Through each of the screens, the system can display the next screen in response to user input, for example a user may press a button (for instance, a virtual control on the screen or a physical button on the second portable computing device 834) to go to the next screen showing the next instructions. The user can be a patient. The second portable computing device 834 can display a screen 916 showing that recording of EEG data by the wearable sensors is in session. The second portable computing device 834 can display an alert, for example an action required screen 910. The action required screen 910 can indicate that one or more actions are required, for example due to one or more detected issues. If multiple actions are required, the action required screen 910 may display a number representing the number of actions required based on a number of detected alerts. In some cases, auditory, visual, or haptic feedback by the second portable computing device 834 alerts a user that an action is required. Auditory, visual, or haptic feedback on one or more wearable sensors 802 can alert a user that an action is required.

The application display on the second portable computing device 834 can display specific information about one or more detected alerts. Specific information about the alert can be displayed in response to user input (such as a tap) on the action required screen 910. For example, the display may indicate that a signal issue is detected (such as a signal issue alert 912) or that a sensor is disconnected (such as a sensor disconnected alert 914). Signal issue alert 912 can indicate that poor electrode contact by one or more wearable sensors has been detected. This can be determined based impedance, as described herein. The number of times that a signal check has been attempted may be tracked (such as, stored in a memory), and an alert is generated responsive to the number of times reaching a threshold (such as, 1 time, 2 times, 3 times, 4 times, 5 times, or more). Signal issue alert 912 can indicate which wearable sensor(s) 802 has a signal issue. Sensor disconnected alert 914 can indicate that one or more wearable sensor(s) 802 have stopped wireless communication with the second portable computing device 834. The system can wirelessly scan (such as, with Bluetooth) for wearable sensors 802. Current sensor state and disconnection count can be tracked (such as, are stored to the memory), and an alert is generated responsive to the number of times reaching a threshold (such as, 1 time, 2 times, 3 times, 4 times, 5 times, or more).

In response to user input, the system can display instructions for how to troubleshoot or reconnect one or more wearable sensors 802. In response to user input, a screen can be displayed, which may instruct a user to confirm whether or not the wearable sensor 802 is attached. In response to user input, signal issue alert 912 or sensor disconnected alert 914 can be snoozed or dismissed. Dismissing or snoozing signal issue alert 912 or sensor disconnected alert 914 may be disabled. After a predefined amount of time has elapsed, signal issue alert 912 or sensor disconnected alert 914 can be automatically timed out and dismissed. In response to user input, a replace attachment screen 918 can be displayed to provide instructions on troubleshooting signal issue alert 912 and sensor disconnected alert 914, as further described herein. After detecting an alert, the second portable computing device 834 can pause recording of EEG data when an alert is detected.

The instructions can further cause the at least one processor to cause a display of a first computing device 832 or a second portable computing device 834 to display an instruction corresponding to a self-diagnosed problem. For example, an instruction may include moving a wearable sensor 802, replacing an attachment (for example, screen 918 instructing a user to replace an attachment), charging the battery of a wearable sensor 802, charging the battery of a first portable computing device 832 or a second portable computing device 834, rebooting a wearable sensor 802 or a first or second portable computing device 832, 834, etc.

Once a user completes the instructed steps, the alert can be dismissed and recording of EEG data can be resumed. The second portable computing device 834 can display the recording in session screen 916 once an alert has been resolved. Recorded EEG data can be sent to a remote server or cloud device. The remote server or cloud device can combine and/or processes the recorded data to determine presence of one or more physiological conditions.

Figure 9B:
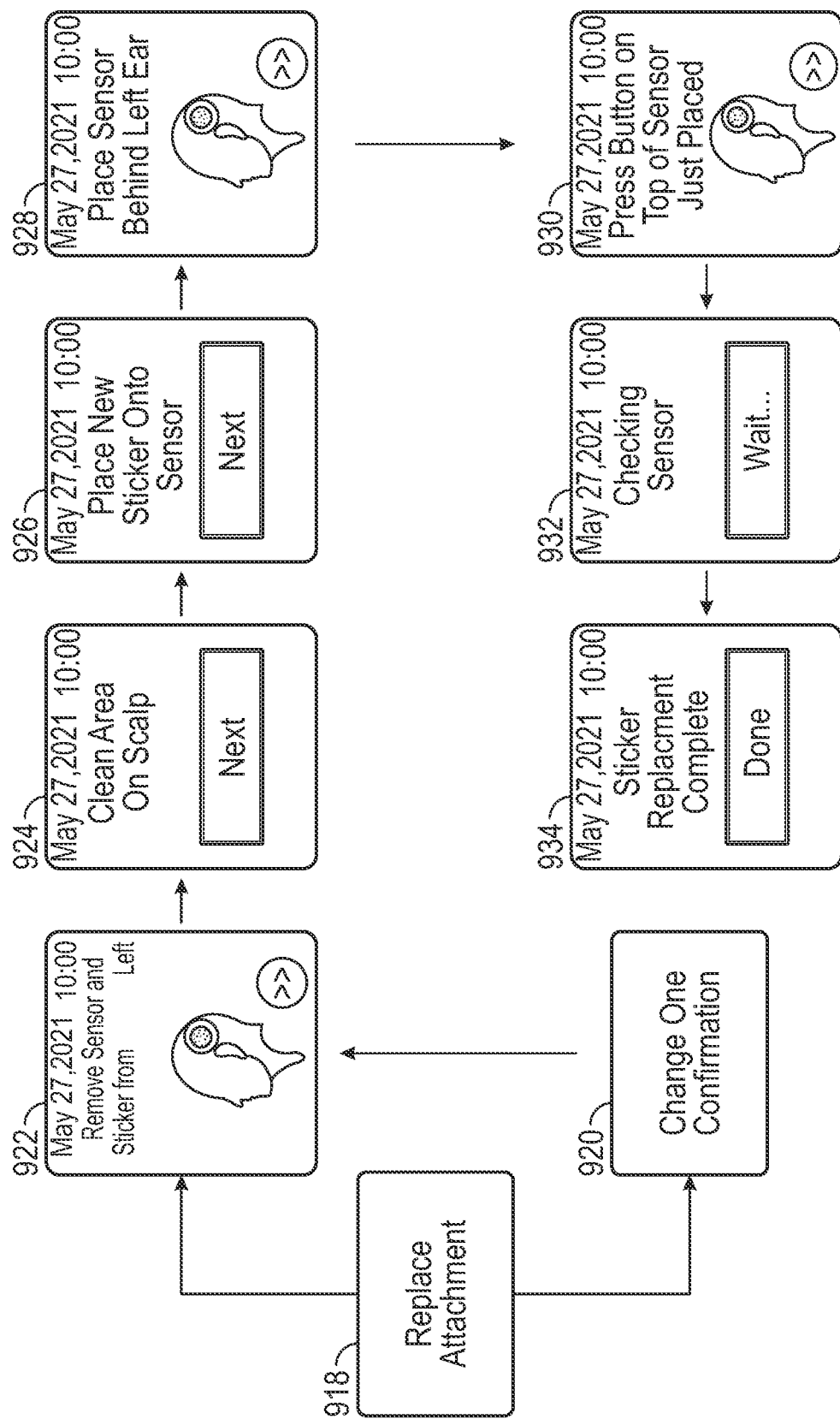

The instructions can be associated with replacing an attachment configured to removably attach a wearable sensor 802 of the plurality of wearable sensors 802 to the scalp of the user. FIG. 9B illustrates example screens illustrating a process for instructing a user to replace an attachment. Through each of the screens, the system can display the next screen in response to user input, for example a user may press a button (as described in connection with FIG. 9A)) to go to the next screen showing the next instructions. An alert screen 918 can instruct a user that an attachment should be replaced. If there has been a sensor failure, the system can display screen 922 and instruct a user to remove a wearable sensor 802 from a location on the scalp.

The second portable computing device 834 can display a screen 920 instructing a user to confirm whether to proceed with attachment replacement. A user may confirm by pressing a button (as described in connection with FIG. 9A). In response to user input canceling replacement of the attachment (such as selecting a cancel user interface option) or in response to the passing of a predefined amount of time, screen 920 may be dismissed. In response to user input confirming proceeding with replacement, the system can display screen 922 and instructs a user to remove a wearable sensor 802 from a location on the scalp. The second portable computing device 834 can command a wearable sensor 802 to enter a sleep state.

Responsive to the instructions to replace attachment, the user can remove the wearable sensor 802, replaces the attachment with another attachment, and repositions the wearable sensor 802 on the scalp of the user. The second portable computing device 834 can instruct a user to remove a wearable sensor 802 from a location on a scalp. In screen 922, for example, the screen of the second portable computing device 834 displays a graphical representation of the location of the wearable sensor. The system can use the known sensor location (determined during set-up, as described herein) to set a screen showing a specific location. Information for the sensor location can be stored in the memory.

The second portable computing device 834 can instruct a user to clean the area of the indicated location on the scalp, for example, by displaying a screen 924. The second portable computing device 834 can instruct a user to place a new attachment onto the wearable sensor 802, for example, by displaying a screen 926. The second portable computing device 834 can instruct a user to place the wearable sensor 802 on a location on the scalp, for example, by displaying screen 928. Screen 928 can include instructions to remove a second liner to expose a second adhesive side of an attachment. The system can use a known sensor/location from the memory to set a screen showing a specific location. The second portable computing device 834 can instruct a user to activate the placed wearable sensor 802 by pressing a button on the placed wearable sensor 802, for example, by displaying screen 930. The second portable computing device 834 can instruct a user to wait, for example, by displaying screen 932, while the wearable sensor 802 is tested for impedance, such as with impedance tests described herein. In some cases, impedance is verified, and the memory is updated on impedance level. If an impedance test fails on a first or a subsequent try (such as, a second try), a Poor Electrode Contact Alert screen (not shown) may be displayed. If an impedance test fails on yet another subsequent try (such as, a third try), a Sensor Failure—No Retry screen (not shown) may be displayed. If impedance is verified (impedance test succeeds), the process may be repeated if attachments for additional wearable sensors 802 need replacement. If attachment replacement completes for one or more wearable sensors 802, the second portable computing device 834 can inform the user that replacement is complete, for example, by displaying screen 934.

Figure 9C:
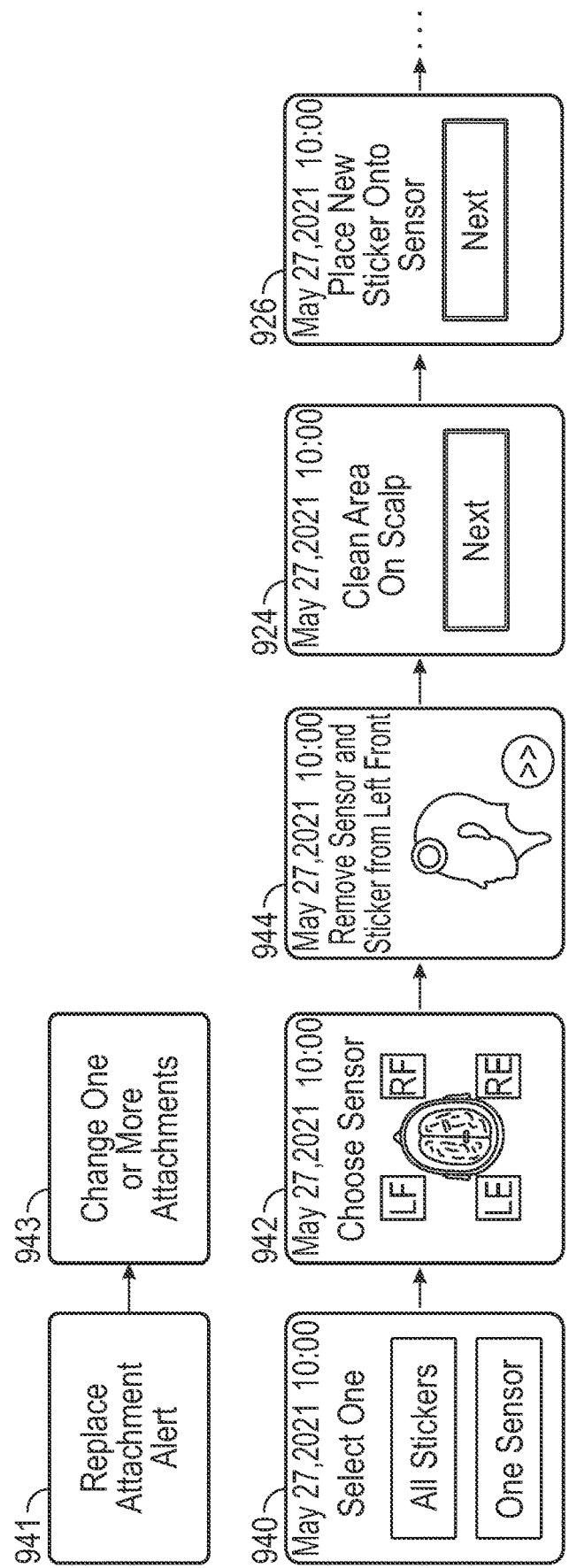

Attachments may need to be periodically replaced, as described herein. The second portable computing device 834 can periodically instruct the user to replace one or more attachments, which can be performed by displaying instructions. FIG. 9C is an illustration of a process for guiding a user through replacing one or more attachments. In some cases, through each of the screens, the system displays the next screen in response to user input, for example a user may press a button (on a screen display or a physical button on the second portable computing device 834) to go to the next screen showing the next instructions. In step 941, an application running on a second portable computing device 834 alerts a user to replace one or more attachments. The alert can be provided periodically, such as every 6 hours or less, 12 hours, 18 hours, 24 hours, 30 hours, 36 hours, 42 hours, 48 hours, 54 hours, 60 hours, 66 hours, or 72 hours, 4 days, 5 days, 6 days, or 7 days or more, or the like or a value therebetween, or a range constructed from any of the aforementioned values or values therebetween. In step 943, the user changes (replaces) one or more attachments (including, for example, all attachments). The application may display several screens on a second portable computing device 834 to guide a user through replacement of an attachment. In screen 940 (which may be displayed responsive the alert in step 941), the application can request user input as to whether one or all attachments would be replaced. In some implementations, the option of replacing more than one but less than all attachments may be provided. In some cases, in response to user input, a process for instructing replacement of only one attachment is initiated. In screen 942, a diagram of wearable sensor 802 locations can be displayed so that a user can input a selection of which wearable sensor 802 attachment should be replaced. Only some wearable sensors 802 may be displayed or allowed to be selected by the user, for example only wearable sensors 802 that are currently active and/or in use. A display (not shown) can ask a user to confirm the selection of the wearable sensor 802 whose attachment that is being replaced. The second portable computing device 834 can command the selected wearable sensor 802 to enter a sleep state.

In screen 944, a user is instructed to remove the selected wearable sensor 802 from its location on the scalp. In the example of screen 944, the screen of the second portable computing device 834 displays a graphical representation of the wearable sensor 802 location. In screen 924, a user is instructed to clean the area where the sticker is placed on the scalp. In screen 926, a user is instructed to place a new attachment (adhesive sticker) onto the wearable sensor 802. Subsequently, additional screens described in connection with FIG. 9B can be displayed. The process may be repeated in sequence to replace attachments for one or more additional wearable sensors 802. For instance, the process may repeat screens 942, 944, 924, 926, etc. for each of the additional wearable sensors 802. As another example, the user can select multiple wearable sensor 802 attachments for replacement in screen 942, and the process can repeat screens 944, 924, 926, etc. for each of the selected wearable sensors.

Figures 9D, 9E:
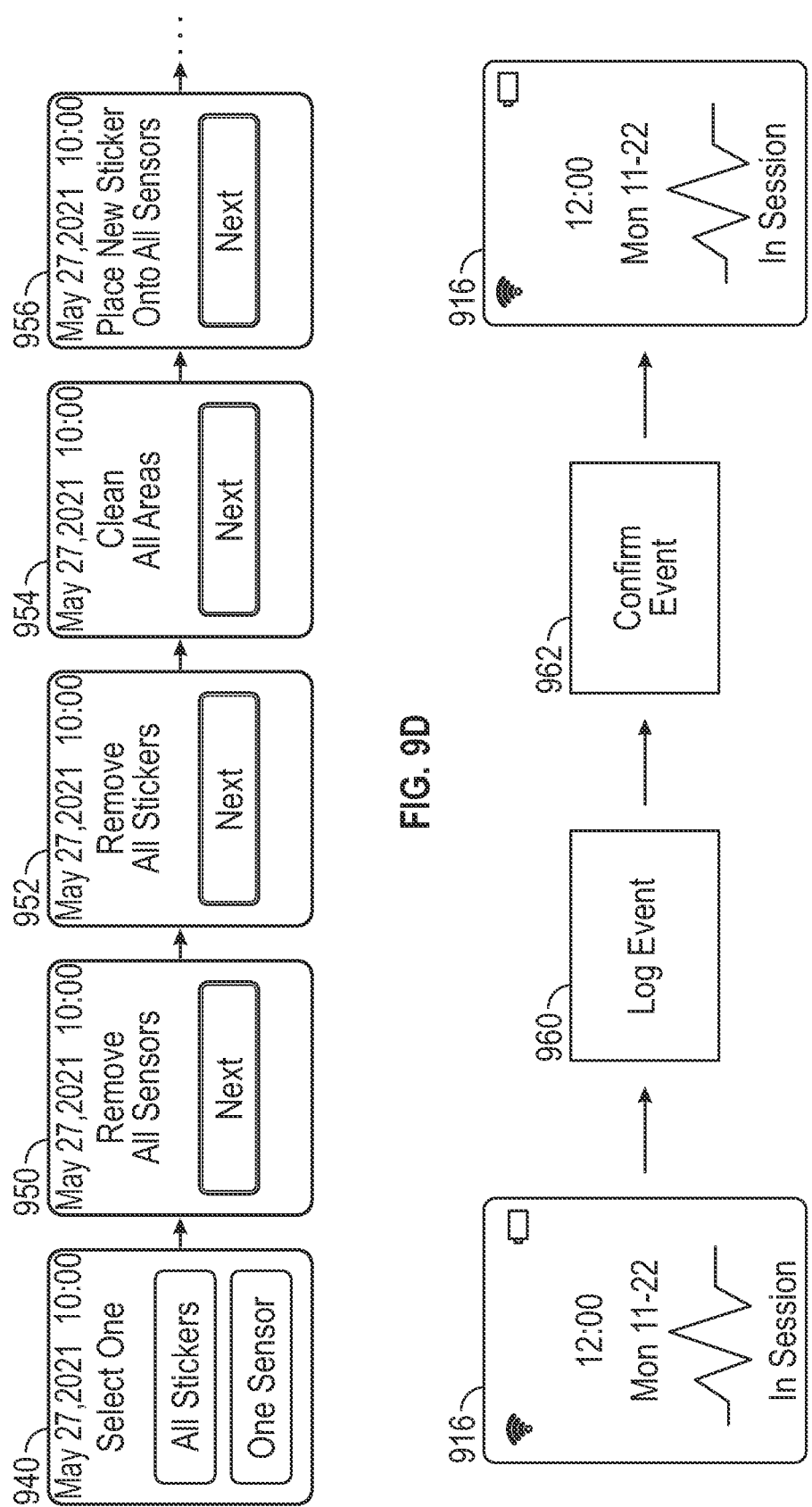

FIG. 9D is an illustration of a process for guiding a user through changing all attachments. In some cases, by all attachments, it is meant all adhesive attachments for all wearable sensors 802 currently in use. In screen 940, the user can select the option for replacing "all stickers." In display 950, the user can be instructed to remove each of the plurality of wearable sensors 802 from each location on the scalp. In display 952, the user can be instructed to remove all attachments from each of the plurality of wearable sensors 802. In display 954, the user can be instructed to clean all areas on the scalp for placement of each of the plurality of wearable sensors 802. In display 956, a user can be instructed to place a new attachment onto each of the plurality of wearable sensors 802. Subsequently, additional screens similar to those described in connection with FIG. 9B can be displayed (such as screens 928, 930, 932, 934).

Provided herein are systems for monitoring of brain activity. The systems can include a plurality of wearable sensors 802 configured to detect EEG signals indicative of a brain activity of a user. Each wearable sensor 802 can include at least two electrodes configured to monitor the EEG signals when the wearable sensor 802 is positioned on a scalp of the user, and an electronic circuitry configured to process the EEG signals monitored by the at least two electrodes and wirelessly transmit processed EEG signals to a first portable computing device 832.

The systems can further include a first non-transitory computer readable medium storing executable instructions that, when executed by at least one processor of the first portable computing device 832, cause the at least one processor of the first portable computing device 832 to facilitate an activation of the plurality of wearable sensors 802 by displaying instructions for the on a display of the first portable computing device 832. The executable instructions can further cause the at least one processor of the first portable computing device 832 to, subsequent to the activation of the plurality of wearable sensors 802, transfer control of the plurality of wearable sensors 802 to a second portable computing device 834 to permit the second portable computing device 834 configured to be worn by the user to wirelessly receive processed EEG signals. The second portable computing device 834 may not include a display or may include a display that is smaller than the display of the first portable computing device 834. The first portable computing device 834 can be configured to facilitate activating and positioning the plurality of wearable sensors 802 on the scalp of the user and the second portable computing device 834 is configured to facilitate monitoring of the brain activity of the user and detecting one or more disorders.

The first portable computing device 832 can be a tablet and the second portable computing device 834 can be a smartwatch. The executable instructions can further cause the at least one processor to of the first portable computing device 832 to, prior to transferring control to the second portable computing device 834, authenticate the second portable computing device 834. Authenticating the second portable computing device 834 can include scanning a QR code of the second portable computing device 834.

The systems can further include a second non-transitory computer readable medium storing executable instructions that, when executed by at least one processor of the second portable computing device 834, cause the at least one processor of the second portable computing device 834 to cause display of an alert on the display of the second portable computing device 834. The executable instructions can further cause the at least one processor of the second portable computing device 834 to cause display of instructions for resolving the alert on the display of the second portable computing device 834. The executable instructions can further cause the at least one processor of the second portable computing device 834 to pause collection of the processed EEG signals.

The executable instructions can cause the at least one processor of the second portable computing device 834 to detect and display the alert responsive to determining that an impedance of at least one wearable sensor of the plurality of wearable sensors does not satisfy an impedance threshold. For example, the signal issue alert 912 of FIG. 9A is a display of an alert on the display of the second portable computing device 834 related to an impedance issue. The instructions can be associated with replacing an attachment configured to removably attach the at least one wearable sensor 802 to the scalp of the user. The instructions can include causing removal of the at least one wearable sensor 802, replacement of the attachment with another attachment, and repositioning the at least one wearable sensor 802 on the scalp of the user. The executable instructions can further cause the at least one processor of the second portable computing device 834 to, responsive to verifying the impedance of the at least one wearable sensor 802 after it has been repositioned on the scalp of the user, resume collection of the processed EEG signals. Verifying the impedance of the at least one wearable sensor 802 can include determining that the impedance of the at least one wearable sensor 802 satisfies the impedance threshold. The executable instructions can facilitate selection of the at least one wearable sensor 802 from the plurality of wearable sensors 802. The (user) instructions can display a position of the at least one wearable sensor 802 on the scalp of the user.

The executable instructions can cause the at least one processor of the second portable computing device 834 to cause display of the alert responsive to passage of a duration of time since replacement of a plurality of attachments configured to removably attach the plurality of wearable sensors 802 to the scalp of the user. The duration of time may be 6 hours or less, 12 hours, 18 hours, 24 hours, 30 hours, 36 hours, 42 hours, 48 hours, 54 hours, 60 hours, 66 hours, or 72 hours, 4 days, 5 days, 6 days, or 7 days or more, or the like or a value therebetween, or a range constructed from any of the aforementioned values or values therebetween.

The systems can further include a second non-transitory computer readable medium storing executable instructions that, when executed by at least one processor of the second portable computing device 834, cause the at least one processor of the second portable computing device 834 to, responsive to a detection of a possible seizure, cause display of instructions for confirming occurrence of a seizure.

As described herein, the wearable sensors 802 can monitor EEG signals for detection of one or more physiological conditions, such as a seizure. EEG data can be processed by one or more recognition techniques, such as machine learning techniques, to detect a seizure. To improve the detection (such as, to train one or more recognition techniques), it may be advantageous to have the user confirm occurrence oft whether a possible seizure has been detected correctly. FIG. 9E displays a process for confirming with a user the occurrence of a seizure. Recording in session screen 916 shows that EEG recording is in session.

In response to user input (such as, a press of a button as described in connection with FIG. 9A), the second portable computing device 834 can display a log event screen 960. The second portable computing device 834 can display a screen (such as log event screen 960) instructing a user to indicate whether or not a seizure just occurred. A user may select yes or no (that a seizure has or has not just occurred) by, for example, pressing a button (as described in connection with FIG. 9A).

If a user inputs that a seizure has occurred, the second portable computing device 834 can add a record of an event to the memory. If a user inputs that no seizure has occurred, the second portable computing device 834 may not add a record of an event to the memory. If a user inputs that a seizure has occurred, the second portable computing device 834 can display a confirm event screen 962. The second portable computing device 834 can display a confirm event screen 962 automatically after a predetermined amount of time (such as 30 seconds or the like) has elapsed since the log event screen 960 was opened. The confirm event screen 962 can indicate to a user that an event indicating occurrence of a seizure has been logged. In response to user input or after the lapse of another predetermined amount of time since displaying confirm event screen 962, recording in session screen 916 can be displayed again.

In some cases, wireless scans (such as Bluetooth scan) are stopped during recording sessions. A wireless scan may start again if a wearable sensor 802 disconnects. Real-time data notifications can be enabled for all wearable sensors 802. When EEG recording is in session, the second portable computing device 834 can receive messages containing real-time data/events from the plurality of wearable sensors 802 and communicates messages containing real-time data/events to a remote server or cloud server over the Internet. Session end messages can be communicated to a remote server or cloud server. In response to user input, the second portable computing device 834 can display an options screen (not shown) or a parental lockout screen (not shown).

Synchronizing Independent Wireless EEG Sensors

Each EEG sensor of a plurality of EEG sensors can independently monitor and collect EEG signals without communicating with the other EEG sensors. Collected EEG signals can be wirelessly transmitted to one or more portable computing device for processing, which can include collating (or unifying, aligning, or synchronizing) and analyzing EEG signals to determine occurrence of one or more physiological conditions. At least some of the processing can be performed by a remote computing device. It can be advantageous to synchronize one or more of collection or transmission of EEG signals by the plurality of sensors so that processing is performed correctly.

Provided herein are methods and systems for synchronized monitoring of brain activity by a plurality of independent EEG sensors configured to detect EEG signals indicative of a brain activity of a user (such as, a patient). Each sensor can be configured to detect EEG signals independent of the other sensors and may not communicate with the other sensors.

Each EEG sensor can include at least two electrodes configured to monitor the EEG signals when the EEG sensor is positioned on a scalp of the user. Each EEG sensor can further include an electronic circuitry configured to, based on the signals detected by the at least two electrodes process the EEG signals monitored by the at least two electrodes and wirelessly transmit the data associated with the brain activity of the user to one or more portable computing devices.

The system can further includes a non-transitory computer readable medium storing executable instructions that, when executed by at least one processor of the one or more portable computing devices, cause the at least one processor to wirelessly transmit a first message to the plurality of EEG sensors to listen to a second message. The executable instructions can cause the at least one processor to, subsequent to transmitting the first message, wirelessly transmit a second message to the plurality of EEG sensors, the second message comprising timing information. Transmission of the second message can cause the electronic circuitry of each EEG sensor to set an internal clock to substantially match internal clocks of the other EEG sensors, the internal clock being used for time stamping recorded signals indicative of the brain activity of the user. Data determined by each EEG wearable sensor can be correlated with data determined by the EEG wearable sensors to within approximately 10 ms or less, 20 ms, 30 ms, 40 ms, 50 ms or more, or the like, or within a range constructed from any of the aforementioned values.

In some cases, no EEG sensor communicates with another EEG sensor. The executable instructions can further cause the at least one processor to, subsequent to wirelessly transmitting the second message, confirm that the EEG sensors have set their internal clocks. The executable instructions can further cause the at least one processor to verify that the processed EEG signals received from each EEG sensor are correlated with the processed EEG signals determined by the other EEG sensors of the plurality of wearable sensors (for example, to within approximately 10 ms or less, 20 ms, 30 ms, 40 ms, 50 ms or more, or the like, or within a range constructed from any of the aforementioned values). The executable instructions can further cause the at least one processor to, responsive to the verification, transmit the processed EEG signals received from the plurality of EEG sensors to a remote computing device.

The executable instructions can further cause the at least one processor to poll the plurality of EEG sensors for their internal clocks. The executable instructions can further cause the at least one processor to, in response to detecting that a difference between an internal clock of at least one EEG sensor and an expected internal clock satisfies a threshold, repeat wireless transmission of the first and second messages to cause the electronic circuitry of the at least one EEG sensor to set the internal clock. The threshold can be no more than about 10 ms, 20 ms, 50 ms, 75 ms, 90 ms, 100 ms, or 200 ms, or within a range constructed from any of the aforementioned values and may be dependent on the specification for the clock synchronization. For instance, a threshold with a higher value would be used for monitoring a physiological signal that varies less frequently. Monitoring such a signal may be performed even when the internal clocks are less accurately synchronized. As another example, a threshold with a lower value would be used for monitoring a physiological signal that varies more frequently. Monitoring such a signal may be necessitate a greater accuracy of synchronization of the internal clocks.

Provided herein are methods for synchronized monitoring of brain activity. The methods can include wirelessly transmitting a first message to a plurality of EEG sensors configured to detect EEG signals indicative of a brain activity of a user (such as, a patient). Each EEG sensor can include at least two electrodes configured to monitor the EEG signals when the EEG sensor is positioned on a scalp of the user. Each EEG sensor can include an electronic circuitry configured to, based on the signals detected by the at least two electrodes, determine data associated with the brain activity of the user.

The methods can further include, subsequent to transmitting the first message, wirelessly transmitting a second message to the plurality of EEG sensors. The second message can include timing information. Transmission of the second message can cause the electronic circuitry of each EEG sensor to set an internal clock to substantially match internal clocks of the other EEG sensors, for example, within a set of activated sensors for a sensor session. The internal clock can be used for time stamping recorded signals indicative of the brain activity of the user.

The methods can further include wirelessly receiving the processed EEG signals from the plurality of EEG sensors and verifying that the processed EEG signals received from each EEG sensor are correlated with the processed EEG signals determined by the other EEG sensors (for example, to within approximately 10 ms or less, 20 ms, 30 ms, 40 ms, 50 ms or more, or the like, or within a range constructed from any of the aforementioned values).

The methods can further include, responsive to the verification, transmitting the processed EEG signals received from the EEG sensors to a remote computing device. The remote computing device can be a portable computing device as described herein. In some cases, no EEG sensor communicates with another EEG sensor. The methods can include verifying that the processed EEG signals received from each EEG sensor is correlated with the processed EEG signals determined by the other EEG sensors (for example, to within approximately 10 ms or less, 20 ms, 30 ms, 40 ms, 50 ms or more, or the like, or within a range constructed from any of the aforementioned values).

The methods can further include confirming that that the plurality of EEG sensors have set their internal clocks. The methods can further include polling the plurality of EEG sensors for their internal clocks. The methods can further include in response to detecting that a difference between an internal clock of at least one EEG sensor and an expected internal clock satisfies a threshold, repeating wireless transmission of the first and second messages to cause the electronic circuitry of the at least one EEG sensor to set the internal clock. This way, any unacceptable clock drift can be detected and corrected.

Figure 10A:
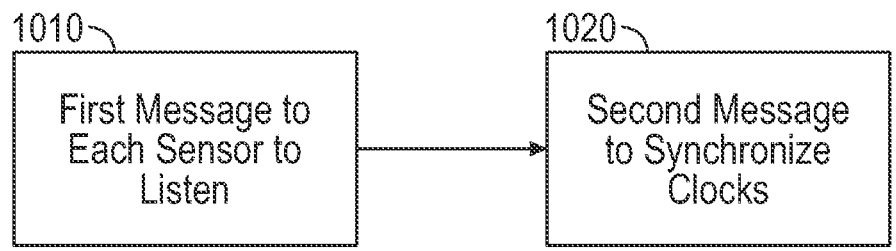
FIG. 10A illustrates a method of synchronizing sensor data for a plurality of independent wireless EEG sensors.

FIG. 10A illustrates a method of synchronizing sensor data for a plurality of independent EEG sensors. The method can be executed by a portable computing device. In step 1010, a first message is sent to each EEG sensor cause the EEG sensor to listen (or transition to a listening state). The first message can be a command sent from the portable computing device. The first message can be a directed message sent individually to each EEG sensor. In some cases, listening is a state of scanning and waiting for a second command (or second message) that includes clock information (such as, a time stamp). The second message can be sent, for instance, as an advertising message using the BLE protocol. BLE mesh capability may be used. The second message can be a single message broadcast to all EEG sensors (as compared to the first message that is directly sent to each EEG sensor). The reason for sending first and second messages can be that the first message causes the EEG sensors to enter into the listening state in which the EEG sensors look for a broadcast message that is received by the EEG sensors simultaneously.

In some cases, a different wireless communication protocol can be used, such as the WiFi protocol, NFC protocol, RFID protocol, or the like. For protocols that support direct broadcast to the EEG sensors (such as, WiFi which supports directs broadcast to all devices on a subnet), it would be sufficient to send a single broadcast message to all EEG devices. The broadcast message can include clock information, which can be a time stamp.

In step 1020, the second message can be sent to each EEG sensor to synchronize the internal clocks of the EEG sensors. The second message can be a command to set the clock of the EEG sensor to the portable device clock (or some other clock value). Thus, the second message can include a clock information (or clock value). As described herein, each of the plurality of individual sensors can receive the second message simultaneously. This way, the internal clocks of EEG sensors will be set to approximately the same clock value (which can be the clock value included in the second message) resulting in synchronous processing of EEG data received from the EEG sensors since the EEG data can transmitted by the EEG sensors along with internal clock values, as described herein.

After all EEG sensors receive and process the second message, each EEG sensor can set the internal clock to the same time setting to a desired tolerance (for example, approximately 10 ms or less, 20 ms, 30 ms, 40 ms, 50 ms or more, or the like, or within a range constructed from any of the aforementioned values). Each individual EEG sensor can record EEG data with a time stamp derived from the internal clock. EEG data packets from sensors can be sent to a portable computing device independently and possibly at different times. The portable computing device may combine data from the plurality of EEG sensors based on time stamps from the individual sensors.

In some cases, if an EEG sensor does not receive the first or second command and does not set its internal clock as described here, when the EEG sensor tries to reconnect with the portable computing device, the portable computing device will recognize that the sensor has not synchronized its internal clock. The portable computing device may then restart the synchronization process of FIG. 10A.

Figure 10B:
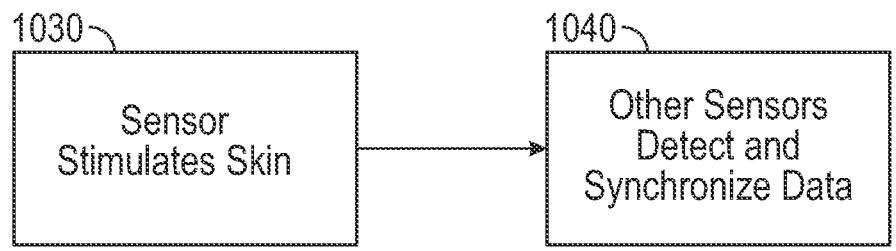
FIG. 10B illustrates an alternative method of synchronizing sensor data for a plurality of independent wireless EEG sensors.

In some implementations, synchronization can be performed as follows. Each EEG sensor can be caused to process an electrical stimulation generated by another EEG sensor and sensed by at least two electrodes and record the electrical stimulation along with data associated with the brain activity of the user. Recording of the electrical stimulation facilitates combining and processing data associated with the brain activity of the user collected by the plurality of EEG sensors. As shown in FIG. 10B, in step 1030, an EEG sensor can stimulate the skin by applying an electrical signal with the electrodes. For example, the EEG sensor can sends a signal (such as railing power through one of the electrodes), which stimulates the skin to create an electrical tap. In step 1040, the other EEG sensors can sense the tap through the skin to synchronize the sensors. Rather than synchronizing the clocks, EEG data can be synchronized by including in the data information indicating that the tap was applied (for the EEG sensor applying the tap) and sensed (for the other EEG sensors). Accordingly, EEG data from different EEG sensors can be combined and aligned by using the information related to tap. Synchronization can be initiated by a portable computing device which receives data packets containing tap information.

In some cases, synchronization can be performed as follows. A recordable event (such as a ping or an instruction to generate stimulation) can be provided via a portable computing device to one of the EEG sensors. The recordable event can be relayed by the EEG sensor to the other EEG sensors, and can be recorded by each of the EEG sensors. Data can be later synchronized using the techniques described in connection with FIG. 10B.

ADDITIONAL EXAMPLES

Example 1: A system for monitoring brain activity comprising:
- a plurality of wearable sensors configured to record a brain activity of a user, each wearable sensor comprising a housing, at least two electrodes positioned on an exterior surface of the housing and configured to detect electroencephalogram (EEG) signals indicative of the brain activity of the user when the wearable sensor is positioned on a scalp of the user, an electronic circuitry supported by the housing and configured to process the EEG signals detected by the at least two electrodes, and a power source supported by the housing and configured to provide power to the electronic circuitry, the housing having an extended, rounded shape; and
- a plurality of attachments, each attachment including a first side shaped to substantially match the extended, rounded shape and configured to be attached to the exterior surface of the housing of a wearable sensor and a second side configured to removably position the wearable sensor on the scalp of the user, a number of attachments in the plurality of attachments being greater than a number of wearable sensors in the plurality of wearable sensors.

Example 2: The system of any of the preceding examples, further comprising a charger comprising a charger housing configured to receive and simultaneously charge power sources of at least two wearable sensors of the plurality of wearable sensors.

Example 3: The system of any of the preceding examples, wherein the extended, rounded shape of the housing is configured to fit around a hairline of the user such that the extended, rounded shape of the housing facilitates unobtrusive wear of the wearable sensor on the scalp of the user while facilitating collection of the EEG signals.

Example 4: The system of example 3, wherein the housing comprises a first portion having a first thickness and a second portion having a second thickness greater than the first thickness.

Example 5: The system of any of the preceding examples, wherein a surface area of the housing is between 16.0 $cm^2$ and 10 $cm^2$.

Example 6: The system of any of the preceding examples, wherein a volume of the housing is between 5.0 $cm^3$ and 3.0 $cm^3$.

Example 7: The system of any of the preceding examples, wherein the number of attachments in the plurality of attachments comprises the number of wearable sensors in the plurality of wearable sensors multiplied by a number of days during which the plurality of wearable sensors are configured to record the brain activity of the user.

Example 8: The system of any of the preceding examples, wherein the first side of each attachment is configured to be attached to a bottom surface of the housing.

Example 9: The system of any of the preceding examples, wherein each attachment of the plurality of attachments comprises hydrocolloid material on the second side of the attachment, the hydrocolloid material facilitating repositioning a wearable sensor on the scalp of the user.

Example 10: The system of any of the preceding examples, wherein each attachment comprises a plurality of layers including one or more of:
- a first layer comprising a thermoplastic resin;
- a second layer comprising a cured hydrogel;
- a third layer comprising an adhesive;
- a fourth layer comprising a non-woven fabric;
- a fifth layer comprising an adhesive; or
- a sixth layer comprising a thermoplastic resin.

Example 11: The system of example 10, wherein the thermoplastic resin comprises PET.

Example 12: The system of any of examples 10 to 11, wherein two or more of the first, second, third, fourth, fifth, or sixth layers are laminated to one another such that the cured hydrogel is disposed between the first layer and the third layer.

Example 13: The system of any of examples 10 to 12, wherein the third and fifth layers form apertures and one or more of the third layer, fourth layer, or the fifth layer includes the cured hydrogel.

Example 14: The system of example 13, wherein the apertures align with the at least two electrodes of a wearable sensor.

Example 15: A unitary, wireless, and wearable sensor configured for monitoring brain activity comprising:
- a housing with an extended, rounded shape configured to fit around a hairline of a user;
- at least two electrodes positioned on an exterior surface of the housing and configured to detect electroencephalogram (EEG) signals indicative of a brain activity of the user when the housing is positioned on a scalp of the user; and
- an electronic circuitry supported by the housing and configured to process the EEG signals detected by the at least two electrodes and wirelessly communicate processed EEG signal to a remote computing device, wherein the extended, rounded shape of the housing facilitates unobtrusive wear of the housing on the scalp of the user while facilitating collection of the EEG signals.

Example 16: The sensor of example 15, wherein the housing comprises a first portion having a first thickness and a second portion having a second thickness greater than the first thickness.

Example 17: The sensor of any of examples 15 to 16, wherein a surface area of the housing is between 16.0 cm$^2$ and 10 cm$^2$.

Example 18: The sensor of any of examples 15 to 17, wherein a volume of the housing is between 5.0 cm$^3$ and 3.0 cm$^3$.

Example 19: A kit comprising a plurality of sensors of any of examples 15 to 18, wherein each sensor is configured to detect electroencephalogram (EEG) signals independent of the other sensors.

Example 20: The kit of example 19, further comprising a plurality of attachments, each attachment including a first side shaped to substantially match the extended, rounded shape and configured to be attached to the exterior surface of the housing of a sensor of the plurality of sensors and a second side configured to removably position the sensor on the scalp of the user, a number of attachments in the plurality of attachments being greater than a number of sensors in the plurality of sensors.

Example 21: The kit of example 20, wherein the number of attachments in the plurality of attachments comprises the number of sensors in the plurality of sensors multiplied by a number of days during which the plurality of sensors are configured to record the brain activity of the user.

Example 22: A system for monitoring brain activity comprising: a plurality of unitary, wireless, and wearable sensors configured to record a brain activity of a user, each sensor comprising:
  a housing with an extended, rounded shape configured to fit around a hairline of a user;
  at least two electrodes positioned on an exterior surface of the housing and configured to detect electroencephalogram (EEG) signals indicative of a brain activity of the user when the housing is positioned on a scalp of the user; and
  an electronic circuitry supported by the housing and configured to process the EEG signals detected by the at least two electrodes and wirelessly communicate processed EEG signal to a remote computing device,
  wherein the extended, rounded shape of the housing facilitates unobtrusive wear of the housing on the scalp of the user while facilitating collection of the EEG signals; and
a plurality of attachments, each attachment including a first side shaped to substantially match the extended, rounded shape and configured to be attached to the exterior surface of the housing of a sensor and a second side configured to removably position the sensor on the scalp of the user, a number of attachments in the plurality of attachments being greater than a number of sensors in the plurality of sensors.

Example 23: A method for monitoring brain activity comprising:
  detaching at least one wearable sensor of a plurality of wearable sensors configured to record a brain activity of a user, each wearable sensor comprising a housing having an extended, rounded shape and at least two electrodes positioned on an exterior surface of the housing and configured to detect electroencephalogram (EEG) signals indicative of the brain activity of the user;
  replacing a first attachment of a plurality of attachments with a second attachment of the plurality of attachments, the first and second attachments including a first side shaped to substantially match the extended, rounded shape and configured to be attached to the exterior surface of the housing of the at least one wearable sensor and a second side configured to removably position the at least one wearable sensor on a scalp of the user, a number of attachments in the plurality of attachments being greater than a number of wearable sensors in the plurality of wearable sensors;
  reattaching the at least one sensor to the scalp of the user by adhering the second side of the second attachment to the scalp of the user; and
  resuming recording of EEG signals indicative of the brain activity of the user.

Example 24: A system for monitoring brain activity comprising:
  a plurality of wearable sensors configured to detect electroencephalogram (EEG) signals indicative of a brain activity of a user, each wearable sensor comprising at least two electrodes configured to monitor the EEG signals when the wearable sensor is positioned on a scalp of the user and an electronic circuitry configured to process the EEG signals monitored by the at least two electrodes; and
  a non-transitory computer readable medium storing executable instructions that, when executed by at least one processor of a portable computing device, cause the at least one processor to:
  provide instructions to position a wearable sensor of the plurality of wearable sensors in a location of a plurality of locations on the scalp of the user and activate the wearable sensor;
  verify an identification of the wearable sensor;
  responsive to verification of the identification of the wearable sensor, verify an impedance of the wearable sensor; and
  responsive to verification of the impedance of the wearable sensor, provide instructions to position and activate another wearable sensor of the plurality of wearable sensors and perform verification of an identification and an impedance of the another wearable sensor.

Example 25: The system of example 24, wherein the executable instruction further cause the at least one processor to sequentially provide instructions to position and activate, verify an identification, and verify an impedance of each wearable sensor of the plurality of wearable sensors.

Example 26: The system of example 25, wherein the executable instruction further cause the at least one processor to, responsive to verification of the identification and impedance of each wearable sensor of the plurality of wearable sensors, record the processed EEG signals wirelessly transmitted by the plurality of wearable sensors.

Example 27: The system of any of examples 24 to 26, wherein the executable instructions further cause the at least one processor to, responsive to not verifying that the impedance of the wearable sensor satisfies an impedance threshold, repeat providing instructions, verifying the identification, and verifying the impedance for the wearable sensor.

Example 28: The system of example 27, wherein the executable instructions further cause the at least one processor to, responsive to not verifying the impedance of the wearable sensor for a second time, restart providing instructions, verifying the identification, and verifying the impedance for the wearable sensor.

Example 29: The system of any of examples 24 to 28, wherein the executable instruction further cause the at least one processor to provide an alert in response to detecting that at least two wearable sensors of the plurality of wearable sensors have been activated for positioning in a location of the plurality of locations on the scalp of the user.

Example 30: The system of example 29, wherein the executable instructions further cause the processor to, responsive to detecting that at least two wearable sensors of the plurality of wearable sensors have been activated for positioning in a particular location of the plurality of locations on the scalp of the user, restart providing instructions, verifying the identification, and verifying the impedance for the plurality of wearable sensors.

Example 31: The system of example 30, wherein detecting that the at least two wearable sensors have been activated for positioning in the particular location comprises detecting that multiple sensors have been activated substantially simultaneously.

Example 32: The system of any of examples 24 to 31, wherein providing instructions to position the wearable sensor comprises displaying instructions on a screen of the portable computing device.

Example 33: The system of example 32, wherein providing instructions to position the wearable sensor comprises displaying the location on the screen of the portable computing device and instructions to activate the wearable sensor.

Example 34: The system of any of examples 24 to 33, wherein the executable instructions further cause the at least one processor to, prior to providing instructions to position the wearable sensor in the location on the scalp of the user, provide instructions to scan or enter the identification for the wearable sensor.

Example 35: The system of any of examples 24 to 34, wherein providing instructions to position the wearable sensor in the location on the scalp of the user comprises instructing a use of a plurality of attachments configured to removably attach the wearable sensor to the scalp of the user.

Example 36: A method for monitoring brain activity comprising:
by at least one processor of a portable computing device:
providing instructions to position a wearable sensor of a plurality of wearable sensors in a location of a plurality of locations on a scalp of a user and activate the wearable sensor, the plurality of wearable sensors configured to detect electroencephalogram (EEG) signals indicative of a brain activity of the user, each wearable sensor comprising at least two electrodes configured to monitor the EEG signals when the wearable sensor is positioned on the scalp of the user and an electronic circuitry configured to process the EEG signals monitored by the at least two electrodes;
verifying an identification of the wearable sensor;
responsive to verifying the identification of the wearable sensor, verifying an impedance of the wearable sensor; and
responsive to verifying the impedance of the wearable sensor, providing instructions to position and activate another wearable sensor of the plurality of wearable sensors and perform verification of an identification and an impedance of the another wearable sensor.

Example 37: The method of example 36, further comprising sequentially providing instructions to position and activate, verify an identification, and verify an impedance of each wearable sensor of the plurality of wearable sensors.

Example 38: The method of example 37, further comprising, responsive to verifying the identification and impedance of each wearable sensor of the plurality of wearable sensors, recording the processed EEG signals wirelessly transmitted by the plurality of wearable sensors.

Example 39: The method of any of examples 36 to 37, further comprising, responsive to not verifying that the impedance of the wearable sensor satisfies an impedance threshold, repeating providing instructions, verifying the identification, and verifying the impedance for the wearable sensor.

Example 40: The method of example 39, further comprising, responsive to not verifying the impedance of the wearable sensor for a second time, restarting providing instructions, verifying the identification, and verifying the impedance for the wearable sensor.

Example 41: The method of any of examples 36 to 40, further comprising providing an alert in response to detecting that at least two wearable sensors of the plurality of wearable sensors have been activated for positioning in a location of the plurality of locations on the scalp of the user.

Example 42: The method of example 41, further comprising, responsive to detecting that at least two wearable sensors of the plurality of wearable sensors have been activated for positioning in a particular location of the plurality of locations on the scalp of the user, restarting providing instructions, verifying the identification, and verifying the impedance for the plurality of wearable sensors.

Example 43: The method of example 42, wherein detecting that the at least two wearable sensors have been activated for positioning in the particular location comprises detecting that multiple sensors have been activated substantially simultaneously.

Example 44: The method of any of examples 36 to 43, wherein providing instructions to position the wearable sensor comprises displaying instructions on a screen of the portable computing device.

Example 45: The method of example 44, wherein providing instructions to position the wearable sensor comprises displaying the location on the screen of the portable computing device and instructions to activate the wearable sensor.

Example 46: The method of any of examples 36 to 45, further comprising, prior to providing instructions to position the wearable sensor in the location on the scalp of the user, providing instructions to scan or enter the identification for the wearable sensor.

Example 47: The method of any of examples 36 to 46, wherein providing instructions to position the wearable sensor in the location on the scalp of the user comprises instructing a use of a plurality of attachments configured to removably attach the wearable sensor to the scalp of the user.

Example 48: A method for monitoring of brain activity comprising:
activating a plurality of wearable sensors configured to detect electroencephalogram (EEG) signals indicative of a brain activity of a user and positioned in a plurality of locations on a scalp of the user, each wearable sensor comprising at least two electrodes configured to monitor the EEG signals when the wearable sensor is positioned on the scalp of the user and an electronic circuitry configured to process the EEG signals monitored by the at least two electrodes and wirelessly transmit processed EEG signals to a first portable computing device, the activating comprising following instructions displayed on a display of the first portable computing device; and subsequent to the activation of the plurality of wearable sensors, transferring control of the plurality of wearable sensors to a second portable computing device configured to be worn by the user to permit the second portable computing device to wirelessly receive the processed EEG signals, the second portable computing device not including a display or including a display that is smaller than the display of the first portable computing device, wherein the first portable computing device is configured to facilitate activating and positioning the plurality of wearable sensors on the scalp of the user and the second portable computing device is configured to facilitate monitoring of the brain activity of the user and detecting one or more disorders.

Example 49: The method of example 48, wherein transferring control causes the first portable computing device to cease wirelessly receiving the processed EEG signals.

Example 50: The method of any of examples 48 to 49, wherein the first portable computing device comprises a tablet and the second portable computing device comprises a smartwatch.

Example 51: The method of any of examples 48 to 50, further comprising, prior to transferring control to the second portable computing device, authenticating the second portable computing device.

Example 52: The method of example 51, wherein authenticating the second portable computing device comprises scanning a QR code of the second portable computing device.

Example 53: The method of any of examples 48 to 52, further comprising, responsive to an alert displayed on the display of the second portable computing device, causing the second portable computing device to display instructions for resolving the alert and following the instructions to resolve the alert.

Example 54: The method of example 53, wherein the instructions are associated with replacing an attachment configured to removably attach a wearable sensor of the plurality of wearable sensors to the scalp of the user, and wherein the method further comprises, responsive to the instructions, removing the wearable sensor, replacing the attachment with another attachment, and repositioning the wearable sensor on the scalp of the user.

Example 55: The method of any of examples 53 to 54, wherein the instructions are associated with replacing a plurality of attachments configured to removably attach the plurality of wearable sensors to the scalp of the user, and wherein the method further comprises, responsive to the instructions, removing the plurality of wearable sensors, replacing the plurality of attachments with another plurality of attachments, and repositioning the plurality of wearable sensors on the scalp of the user.

Example 56: A system for monitoring of brain activity comprising:
 a plurality of wearable sensors configured to detect electroencephalogram (EEG) signals indicative of a brain activity of a user, each wearable sensor comprising at least two electrodes configured to monitor the EEG signals when the wearable sensor is positioned on a scalp of the user and an electronic circuitry configured to process the EEG signals monitored by the at least two electrodes and wirelessly transmit processed EEG signals to a first portable computing device;
 a first non-transitory computer readable medium storing executable instructions that, when executed by at least one processor of the first portable computing device, cause the at least one processor of the first portable computing device to:
 facilitate an activation of the plurality of wearable sensors by displaying instructions on a display of the first portable computing device; and
 subsequent to the activation of the plurality of wearable sensors, transfer control of the plurality of wearable sensors to a second portable computing device to permit the second portable computing device configured to be worn by the user to wirelessly receive processed EEG signals, the second portable computing device not including a display or including a display that is smaller than the display of the first portable computing device,
 wherein the first portable computing device is configured to facilitate activating and positioning the plurality of wearable sensors on the scalp of the user and the second portable computing device is configured to facilitate monitoring of the brain activity of the user and detecting one or more disorders.

Example 57: The system of example 56, wherein the first portable computing device comprises a tablet and the second portable computing device comprises a smartwatch.

Example 58: The system of any of examples 56 to 57, wherein the executable instructions further cause the at least one processor to of the first portable computing device to, prior to transferring control to the second portable computing device, authenticate the second portable computing device.

Example 59: The system of example 58, wherein authenticating the second portable computing device comprises scanning a QR code of the second portable computing device.

Example 60: The system of any of examples 56 to 59 further comprising a second non-transitory computer readable medium storing executable instructions that, when executed by at least one processor of the second portable computing device, cause the at least one processor of the second portable computing device to:
 cause display of an alert on the display of the second portable computing device;
 cause display of user instructions for resolving the alert on the display of the second portable computing device; and
 pause collection of the processed EEG signals.

Example 61: The system of example 60, wherein the executable instructions cause the at least one processor of the second portable computing device to detect the alert responsive to determining that an impedance of at least one wearable sensor of the plurality of wearable sensors does not satisfy an impedance threshold.

Example 62: The system of example 61, wherein:
 the user instructions are associated with replacing an attachment configured to removably attach the at least one wearable sensor to the scalp of the user, the instructions comprising causing removal of the at least one wearable sensor, replacement of the attachment with another attachment, and repositioning the at least one wearable sensor on the scalp of the user; and
 the executable instructions further cause the at least one processor of the second portable computing device to, responsive to verifying the impedance of the at least one wearable sensor after it has been repositioned on the scalp of the user, resume collection of the processed EEG signals.

Example 63: The system of example 62, wherein verifying the impedance of the at least one wearable sensor comprises determining that the impedance of the at least one wearable sensor satisfies the impedance threshold.

Example 64: The system of any of examples 62 to 63, wherein the executable instructions facilitate selection of the at least one wearable sensor from the plurality of wearable sensors, and wherein the instructions display a position of the at least one wearable sensor on the scalp of the user.

Example 65: The system of any of examples 60 to 64, wherein the executable instructions cause the at least one processor of the second portable computing device to cause display of the alert responsive to passage of a duration of time since replacement of a plurality of attachments configured to removably attach the plurality of wearable sensors to the scalp of the user.

Example 66: The system of example 65, wherein the duration of time comprises 24 hours.

Example 67: The system of any of examples 56 to 66 further comprising a second non-transitory computer readable medium storing executable instructions that, when executed by at least one processor of the second portable computing device, cause the at least one processor of the second portable computing device to:
responsive to a detection of a possible seizure, cause display of instructions for confirming occurrence of a seizure.

Example 68: A system for synchronized monitoring of brain activity comprising:
a plurality of wearable sensors configured to detect electroencephalogram (EEG) signals indicative of a brain activity of a user, each wearable sensor comprising at least two electrodes configured to configured to monitor the EEG signals when the wearable sensor is positioned on a scalp of the user and an electronic circuitry configured to process the EEG signals monitored by the at least two electrodes and wirelessly transmit processed EEG signals to a portable computing device; and
a non-transitory computer readable medium storing executable instructions that, when executed by at least one processor of the portable computing device, cause the at least one processor to:
wirelessly transmit a message including a clock information to the plurality of wearable sensors; and
cause the electronic circuitry of each wearable sensor of the plurality of wearable sensors to set an internal clock to the clock information so that the internal clock substantially matches internal clocks of the other wearable sensors of the plurality of wearable sensors, the internal clock being used for time stamping recorded signals indicative of the brain activity of the user, wherein data determined by each wearable sensor of the plurality of wearable sensors is correlated with data determined by the other wearable sensors of the plurality of wearable sensors to no more than 200 ms.

Example 69: The system of example 68, wherein no wearable sensor of the plurality of wearable sensors communicates with another wearable sensor of the plurality of wearable sensors.

Example 70: The system of any of examples 68 to 69, wherein data determined by each wearable sensor of the plurality of wearable sensors is correlated with data determined by the other wearable sensors of the plurality of wearable sensors to no more than 50 ms.

Example 71: The system of any of examples 66 to 68, wherein the executable instructions further cause the at least one processor to, subsequent to wirelessly transmitting the message, confirm that the plurality of wearable sensors have set their internal clocks.

Example 72: The system of any of examples 68 to 71, wherein the executable instructions further cause the at least one processor to verify that the processed EEG signals received from each wearable sensor of the plurality of wearable sensors are correlated with the processed EEG signals determined by the other wearable sensors of the plurality of wearable sensors to no more than 200 ms.

Example 73: The system of example 72, wherein the executable instructions further cause the at least one processor to, responsive to the verifying, transmit the processed EEG signals received from the plurality of wearable sensors to a remote computing device.

Example 74: The system of any of examples 68 to 73, wherein the executable instructions further cause the at least one processor to:
poll the plurality of wearable sensors for their internal clocks; and
in response to detecting that a difference between an internal clock of at least one wearable sensor of the plurality of wearable sensors and an expected internal clock satisfies a threshold, repeat wireless transmission of the message to cause the electronic circuitry of the at least one wearable sensor to set the internal clock.

Example 75: The system of any of examples 68 to 74, wherein the executable instructions cause the at least one processor to wirelessly transmitting the message by:
wirelessly transmitting a first message to each wearable sensor of the plurality of wearable sensors and cause the electronic circuitry of the plurality of wearable sensors to listen to a second message; and
subsequent to transmitting the first message, wirelessly broadcasting a second message to the plurality of wearable sensors, the second message comprising the clock information.

Example 76: The system of example 75, wherein the first and second messages are transmitted using Bluetooth low energy (BLE) protocol.

Example 77: A method for synchronized monitoring of brain activity comprising:
wirelessly transmitting a message including a clock information to a plurality of wearable sensors, the plurality of wearable sensors configured to detect electroencephalogram (EEG) signals indicative of a brain activity of a user, each wearable sensor comprising at least two electrodes configured to configured to monitor the EEG signals when the wearable sensor is positioned on a scalp of the user and an electronic circuitry configured to process the EEG signals monitored by the at least two electrodes and wirelessly transmit processed EEG signals to a portable computing device;
cause the electronic circuitry of each wearable sensor of the plurality of wearable sensors to set an internal clock to the clock information so that the internal clock substantially matches internal clocks of the other wearable sensors of the plurality of wearable sensors, the internal clock being used for time stamping recorded signals indicative of the brain activity of the user;
wirelessly receiving the processed EEG signals from the plurality of wearable sensors and verifying that the processed EEG signals received from each wearable sensor of the plurality of wearable sensors are correlated with the processed EEG signals determined by the other wearable sensors of the plurality of wearable sensors to no more than 200 ms; and responsive to the verifying, transmitting the processed EEG signals received from the plurality of wearable sensors to a remote computing device.

Example 78: The method of example 77, wherein no wearable sensor of the plurality of wearable sensors communicates with another wearable sensor of the plurality of wearable sensors.

Example 79: The method of any of examples 77 to 78, wherein verifying comprises verifying that the processed EEG signals received from each wearable sensor of the plurality of wearable sensors are correlated with the processed EEG signals determined by the other wearable sensors of the plurality of wearable sensors to no more than 50 ms.

Example 80: The method of any of examples 77 to 79, further comprising confirming that that the plurality of wearable sensors have set their internal clocks.

Example 81: The method of example 80, further comprising: polling the plurality of wearable sensors for their internal clocks; and in response to detecting that a difference between an internal clock of at least one wearable sensor of the plurality of wearable sensors and an expected internal clock satisfies a threshold, repeating wireless transmission of the message to cause the electronic circuitry of the at least one wearable sensor to set the internal clock.

Example 82: The method of any of examples 77 to 81, wherein wirelessly transmitting the message comprises:
wirelessly transmitting a first message to each wearable sensor of the plurality of wearable sensors and cause the electronic circuitry of the plurality of wearable sensors to listen to a second message; and
subsequent to transmitting the first message, wirelessly broadcasting a second message to the plurality of wearable sensors, the second message comprising the clock information.

Example 83: The method of example 82, wherein the first and second messages are transmitted using Bluetooth low energy (BLE) protocol.

Example 84: A system for synchronized monitoring of brain activity comprising:
a plurality of wearable sensors configured to record a brain activity of a user, each wearable sensor comprising at least two electrodes configured to detect signals indicative of the brain activity of the user when the wearable sensor is positioned on a scalp of the user and an electronic circuitry configured to, based on the signals detected by the at least two electrodes, determine data associated with the brain activity of the user; and
a non-transitory computer readable medium storing instructions that, when executed by at least one processor of the electronic circuitry of a wearable sensor of a plurality of wearable sensors, cause the at least one processor to:
cause at least one two electrodes of the wearable sensor to apply an electrical stimulation configured to be sensed by other wearable sensors of the plurality of wearable sensors; and
cause an electronic circuitry of each wearable sensor of the other wearable sensors to process the electrical stimulation sensed by at least two electrodes and record the electrical stimulation along with data associated with the brain activity of the user, wherein recording of the electrical stimulation facilitates combining and processing data associated with the brain activity of the user collected by the plurality of wearable sensors.

One or more features of any one of the foregoing examples can be used with one or more features of any other example.

OTHER VARIATIONS

The general principles described herein may be extended to other scenarios. For example, for intensive care in pediatric and adults two sensors, four sensors, eight sensors, or various combination of sensors may be used.

Various other configurations are may also be used, with particular elements that are depicted as being implemented in hardware may instead be implemented in software, firmware, or a combination thereof. One of ordinary skill in the art will recognize various alternatives to the specific embodiments described herein.

The specification and figures describe particular embodiments which are provided for ease of description and illustration and are not intended to be restrictive. Embodiments may be implemented to be used in various environments without departing from the spirit and scope of the disclosure.

At least some elements of a device of the present application can be controlled and at least some steps of a method of the invention can be effectuated, in operation with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (for example read-only memory devices within a computer, such as ROM, or devices readable by a computer I/O attachment, such as CD-ROM or DVD disks), information alterably stored on writable storage media (for example floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

In various embodiments, input from a user may be requested. Examples of methods for receiving user input, such as receiving a button press from a user, are illustrative and not by means of limitation. Alternative methods of receiving user input may be used, including receiving a button press on a touch screen, a physical button press on a device, a swipe, a tap, any other touch gestures, a spoken (audio) input, etc.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Depending on the embodiment, certain acts, events, or functions of any of the processes or algorithms described herein can be performed in a different sequence, can be added, merged, or left out altogether. Moreover, in certain embodiments, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a machine learning service server, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A machine learning service server can be or include a microprocessor, but in the alternative, the machine learning service server can be or include a controller, microcontroller, or state machine, combinations of the same, or the like configured to generate and publish machine learning services backed by a machine learning model. A machine learning service server can include electrical circuitry configured to process computer-executable instructions. Although described herein primarily with respect to digital technology, a machine learning service server may also include primarily analog components. For example, some or all of the modeling, simulation, or service algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a machine learning service server, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An illustrative storage medium can be coupled to the machine learning service server such that the machine learning service server can read information from, and write information to, the storage medium. In the alternative, the storage medium can be integral to the machine learning service server. The machine learning service server and the storage medium can reside in an ASIC. The ASIC can reside in a user terminal. In the alternative, the machine learning service server and the storage medium can reside as discrete components in a user terminal (for example, access device or network service client device).

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system for synchronized monitoring of brain activity comprising:
   a plurality of wearable sensors configured to detect electroencephalogram (EEG) signals indicative of a brain activity of a user, each wearable sensor comprising at least two electrodes configured to monitor the EEG signals when the wearable sensor is positioned on a scalp of the user and an electronic circuitry configured to process the EEG signals monitored by the at least two electrodes and wirelessly transmit processed EEG signals to a computing device; and
   a non-transitory computer readable medium storing executable instructions that, when executed by at least one processor of the computing device, cause the at least one processor to:
   wirelessly transmit a message including a clock information to the plurality of wearable sensors;
   cause the electronic circuitry of each wearable sensor of the plurality of wearable sensors to, in response to receiving the message, set, without communicating with any other wearable sensor of the plurality of wearable sensors, its internal clock value to the clock information so that the internal clock value substantially matches internal clock values of the other wearable sensors of the plurality of wearable sensors, the internal clock value being used for time stamping recorded EEG signals indicative of the brain activity of the user, wherein recorded EEG signals determined by each wearable sensor of the plurality of wearable sensors are temporally correlated with recorded EEG signals determined by the other wearable sensors of the plurality of wearable sensors;
   check the plurality of wearable sensors for their internal clock values; and
   in response to a detection that an internal clock value of at least one first wearable sensor of the plurality of wearable sensors is different from an expected first internal clock value associated with the clock information, repeat wireless transmission of the message to cause the electronic circuitry of the at least one first wearable sensor to set the internal clock value so that the internal clock value substantially matches internal clock values of the other wearable sensors of the plurality of wearable sensors.

2. The system of claim 1, wherein recorded EEG signals determined by each wearable sensor of the plurality of wearable sensors are temporally correlated with recorded EEG signals determined by the other wearable sensors of the plurality of wearable sensors to within no more than 200 ms.

3. The system of claim 1, wherein recorded EEG signals determined by each wearable sensor of the plurality of wearable sensors are temporally correlated with recorded EEG signals determined by the other wearable sensors of the plurality of wearable sensors to within no more than 50 ms.

4. The system of claim 1, wherein the executable instructions further cause the at least one processor to, subsequent to wirelessly transmitting the message, confirm that the plurality of wearable sensors have set their internal clock values.

5. The system of claim 1, wherein the executable instructions further cause the at least one processor to verify that the processed EEG signals received from each wearable sensor of the plurality of wearable sensors are temporally correlated with the processed EEG signals determined by the other wearable sensors of the plurality of wearable sensors to within no more than 200 ms.

6. The system of claim 5, wherein the executable instructions further cause the at least one processor to, responsive to verifying, transmit the processed EEG signals received from the plurality of wearable sensors to a remote computing device.

7. The system of claim 1, wherein the executable instructions further cause the at least one processor to:
   poll the plurality of wearable sensors for their internal clock values; and
   in response to detecting that a difference between the internal clock value of at least one second wearable sensor of the plurality of wearable sensors and an expected second internal clock value satisfies a threshold, repeat wireless transmission of the message to cause the electronic circuitry of the at least one second wearable sensor to set the internal clock value.

8. The system of claim 1, wherein the executable instructions cause the at least one processor to wirelessly transmit the message by:
   wirelessly transmitting a first message to each wearable sensor of the plurality of wearable sensors and cause electronic circuitries of the plurality of wearable sensors to, in response to receiving the first message, listen to a second message; and
   subsequent to transmitting the first message, wirelessly broadcasting the second message to the plurality of wearable sensors, the second message comprising the clock information.

9. The system of claim 8, wherein the first and second messages are transmitted using Bluetooth Low Energy (BLE) protocol.

10. A method for synchronized monitoring of brain activity comprising:
   wirelessly transmitting a message including a clock information to a plurality of wearable sensors, the plurality of wearable sensors configured to detect electroencephalogram (EEG) signals indicative of a brain activity of a user, each wearable sensor comprising at least two electrodes configured to monitor the EEG signals when the wearable sensor is positioned on a scalp of the user and an electronic circuitry configured to process the EEG signals monitored by the at least two electrodes and wirelessly transmit processed EEG signals to a computing device;
   causing the electronic circuitry of each wearable sensor of the plurality of wearable sensors to, in response to receiving the message, set, without communicating with any other wearable sensor of the plurality of wearable sensors, its internal clock value to the clock information so that the internal clock value substantially matches internal clock values of the other wearable sensors of the plurality of wearable sensors, the internal clock value being used for time stamping recorded EEG signals indicative of the brain activity of the user;
   wirelessly receiving the processed EEG signals from the plurality of wearable sensors and verifying that the processed EEG signals received from each wearable sensor of the plurality of wearable sensors are temporally correlated with the processed EEG signals determined by the other wearable sensors of the plurality of wearable sensors;

responsive to verifying, transmitting the processed EEG signals received from the plurality of wearable sensors to a remote computing device; and responsive to not verifying, repeating wireless transmission of the message to cause the electronic circuitry of at least one first wearable sensor whose internal clock value is different from an expected first internal clock value associated with the clock information, to set the internal clock value so that the internal clock value substantially matches internal clock values of the other wearable sensors of the plurality of wearable sensors.

11. The method of claim 10, wherein verifying comprises verifying that the processed EEG signals received from each wearable sensor of the plurality of wearable sensors are temporally correlated with the processed EEG signals determined by the other wearable sensors of the plurality of wearable sensors to within no more than 200 ms.

12. The method of claim 10, wherein verifying comprises verifying that the processed EEG signals received from each wearable sensor of the plurality of wearable sensors are temporally correlated with the processed EEG signals determined by the other wearable sensors of the plurality of wearable sensors to within no more than 50 ms.

13. The method of claim 10, further comprising confirming that the plurality of wearable sensors have set their internal clock values.

14. The method of claim 10, further comprising:
polling the plurality of wearable sensors for their internal clock values; and
in response to detecting that a difference between the internal clock value of at least one second wearable sensor of the plurality of wearable sensors and an expected second internal clock value satisfies a threshold, repeating wireless transmission of the message to cause the electronic circuitry of the at least one second wearable sensor to set the internal clock value.

15. The method of claim 10, wherein wirelessly transmitting the message comprises:
wirelessly transmitting a first message to each wearable sensor of the plurality of wearable sensors and cause electronic circuitries of the plurality of wearable sensors to, in response to receiving the first message, listen to a second message; and
subsequent to transmitting the first message, wirelessly broadcasting the second message to the plurality of wearable sensors, the second message comprising the clock information.

16. The method of claim 15, wherein the first and second messages are transmitted using Bluetooth Low Energy (BLE) protocol.

17. A system for synchronized monitoring of brain activity comprising:
a plurality of wearable sensors configured to detect electroencephalogram (EEG) signals indicative of a brain activity of a user, each wearable sensor comprising at least two electrodes configured to monitor the EEG signals when the wearable sensor is positioned on a scalp of the user and an electronic circuitry configured to process the EEG signals monitored by the at least two electrodes and wirelessly transmit processed EEG signals to a computing device; and a non-transitory computer readable medium storing executable instructions that, when executed by at least one processor of the computing device, cause the at least one processor to:
wirelessly transmit a message including a clock information to the plurality of wearable sensors;
cause the electronic circuitry of each wearable sensor of the plurality of wearable sensors, in response to receiving the message, to set, without communicating with any other wearable sensor of the plurality of wearable sensors, its internal clock value to the clock information so that the internal clock value substantially matches internal clock values of the other wearable sensors of the plurality of wearable sensors, the internal clock value being used for time stamping recorded EEG signals indicative of the brain activity of the user, wherein recorded EEG signals determined by each wearable sensor of the plurality of wearable sensors are temporally correlated with recorded EEG signals determined by the other wearable sensors of the plurality of wearable sensors;
poll the plurality of wearable sensors for their internal clock values; and
in response to detecting that a difference between the internal clock value of at least one wearable sensor of the plurality of wearable sensors and an expected internal clock value satisfies a threshold, repeat wireless transmission of the message to cause the electronic circuitry of the at least one wearable sensor to set the internal clock value.

18. The system of claim 17, wherein recorded EEG signals determined by each wearable sensor of the plurality of wearable sensors are temporally correlated with recorded EEG signals determined by the other wearable sensors of the plurality of wearable sensors to within no more than 200 ms.

19. A method for synchronized monitoring of brain activity comprising:
wirelessly transmitting a message including a clock information to a plurality of wearable sensors, the plurality of wearable sensors configured to detect electroencephalogram (EEG) signals indicative of a brain activity of a user, each wearable sensor comprising at least two electrodes configured to monitor the EEG signals when the wearable sensor is positioned on a scalp of the user and an electronic circuitry configured to process the EEG signals monitored by the at least two electrodes and wirelessly transmit processed EEG signals to a computing device;
causing the electronic circuitry of each wearable sensor of the plurality of wearable sensors to, in response to receiving the message, set, without communicating with any other wearable sensor of the plurality of wearable sensors, its internal clock value to the clock information so that the internal clock value substantially matches internal clock values of the other wearable sensors of the plurality of wearable sensors, the internal clock value being used for time stamping recorded EEG signals indicative of the brain activity of the user;
wirelessly receiving the processed EEG signals from the plurality of wearable sensors and verifying that the processed EEG signals received from each wearable sensor of the plurality of wearable sensors are temporally correlated with the processed EEG signals determined by the other wearable sensors of the plurality of wearable sensors;

responsive to verifying, transmitting the processed EEG signals received from the plurality of wearable sensors to a remote computing device;

polling the plurality of wearable sensors for their internal clock values; and in response to detecting that a difference between the internal clock value of at least one wearable sensor of the plurality of wearable sensors and an expected internal clock value satisfies a threshold, repeating wireless transmission of the message to cause the electronic circuitry of the at least one wearable sensor to set the internal clock value.

20. The method of claim 19, wherein verifying comprises verifying that the processed EEG signals received from each wearable sensor of the plurality of wearable sensors are temporally correlated with the processed EEG signals determined by the other wearable sensors of the plurality of wearable sensors to within no more than 200 ms.

* * * * *